(12) United States Patent
Sappenfield

(10) Patent No.: US 8,152,679 B2
(45) Date of Patent: Apr. 10, 2012

(54) ROTARY UNITS, ROTARY MECHANISMS, AND RELATED APPLICATIONS

(76) Inventor: Christopher C. Sappenfield, San Diego, CA (US)

(*) Notice: Subject to any disclaimer, the term of this patent is extended or adjusted under 35 U.S.C. 154(b) by 344 days.

(21) Appl. No.: 12/577,326

(22) Filed: Oct. 12, 2009

(65) Prior Publication Data

US 2010/0089200 A1 Apr. 15, 2010

Related U.S. Application Data

(60) Provisional application No. 61/104,748, filed on Oct. 12, 2008.

(51) Int. Cl.
*F16H 48/06* (2006.01)
(52) U.S. Cl. .................................................. 475/221
(58) Field of Classification Search .................. None
See application file for complete search history.

(56) References Cited

U.S. PATENT DOCUMENTS

| | | | |
|---|---|---|---|
| 845,103 A * | 2/1907 | Ljungstrom | 475/335 |
| 3,892,278 A | 7/1975 | Smith et al. | |
| 4,044,841 A | 8/1977 | Smith et al. | |
| 4,132,131 A | 1/1979 | DeBruyne | |
| 4,159,624 A | 7/1979 | Gruner | |
| 4,611,504 A | 9/1986 | Rundle | |
| 4,683,897 A | 8/1987 | McBride | |
| 4,763,031 A | 8/1988 | Wang | |
| 4,896,567 A | 1/1990 | Zhou et al. | |
| 4,926,715 A | 5/1990 | Hirt et al. | |
| 5,014,428 A | 5/1991 | Yamashita | |
| 5,426,806 A | 6/1995 | Johnson et al. | |
| 5,595,147 A | 1/1997 | Feuling | |
| 5,724,867 A | 3/1998 | Jordan | |
| 6,032,313 A | 3/2000 | Tsang | |
| 6,176,804 B1 | 1/2001 | Kekki et al. | |
| 6,222,293 B1 | 4/2001 | Ikeda et al. | |
| 6,357,118 B1 | 3/2002 | Eichhorn et al. | |
| 6,418,810 B1 | 7/2002 | Kerr | |
| 6,492,743 B1 | 12/2002 | Appa | |
| 6,626,792 B2 | 9/2003 | Vranish | |
| 6,669,594 B2 | 12/2003 | Kerr | |
| 6,672,538 B2 | 1/2004 | Millea et al. | |
| 6,732,603 B1 | 5/2004 | Hsu et al. | |
| 6,799,579 B2 | 10/2004 | Joseph | |
| 6,829,457 B2 | 12/2004 | Ryuzaki et al. | |
| 7,022,042 B2 | 4/2006 | Fleytman | |
| 7,108,629 B2 | 9/2006 | Hiraiwa | |
| 7,118,340 B2 | 10/2006 | D'Anna | |

(Continued)

OTHER PUBLICATIONS

International Preliminary Report on Patentability for International (PCT) Patent Application No. PCT/US2009/060386, mailed Apr. 21, 2011.

(Continued)

*Primary Examiner* — Dirk Wright
(74) *Attorney, Agent, or Firm* — Christopher C. Sappenfield

(57) ABSTRACT

The invention relates to rotary units and rotary mechanisms that are suitable for use in numerous applications. Rotary units typically include rotational components that are configured to rotate. In some embodiments, for example, multiple rotary units are assembled in rotary mechanisms such that neighboring pairs of rotational components counter-rotate or contra-rotate relative to one another during operation of the rotary mechanisms. Rotational components generally include one or more implements that are structured to perform or effect one or more types of work as the rotational components rotate relative to one another in a given rotary mechanism. In certain embodiments, implements are configured to rotate and/or to effect the movement of other components as rotational components rotate.

22 Claims, 35 Drawing Sheets

U.S. PATENT DOCUMENTS

| | | | |
|---|---|---|---|
| 7,153,004 | B2 | 12/2006 | Galli |
| 7,182,708 | B2 * | 2/2007 | Winzeler ........................ 475/337 |
| 7,296,495 | B2 * | 11/2007 | Quinn ............................. 74/640 |
| 2007/0249460 | A1 | 10/2007 | Schulz et al. |
| 2008/0070739 | A1 | 3/2008 | Nakamura et al. |
| 2008/0134513 | A1 | 6/2008 | Oh |
| 2008/0233815 | A1 | 9/2008 | Nakamura et al. |

OTHER PUBLICATIONS

International Search Report for International (PCT) Patent Application No. PCT/US2009/060386, mailed Nov. 25, 2009.

Written Oppinion for International (PCT) Patent Application No. PCT/US2009/060386, mailed Nov. 25, 2009.

* cited by examiner

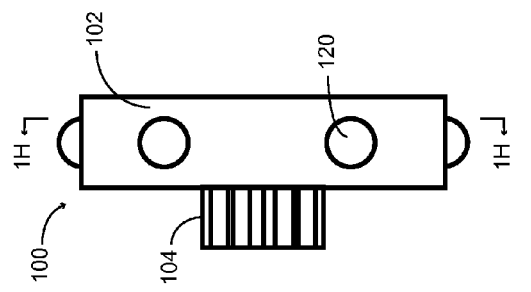
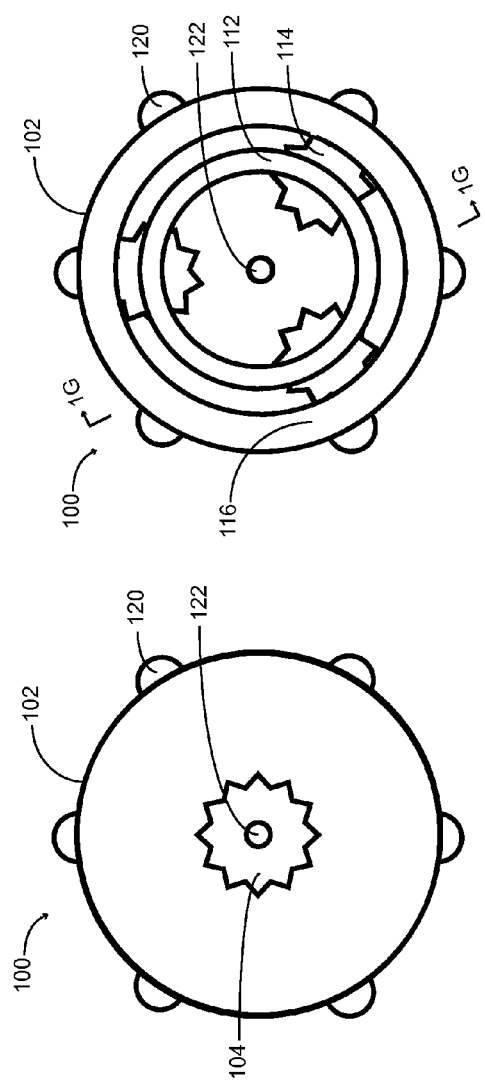
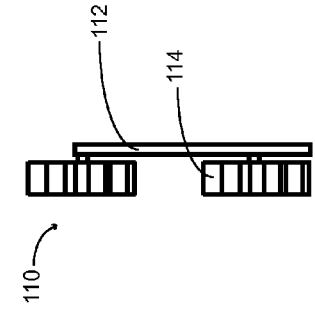
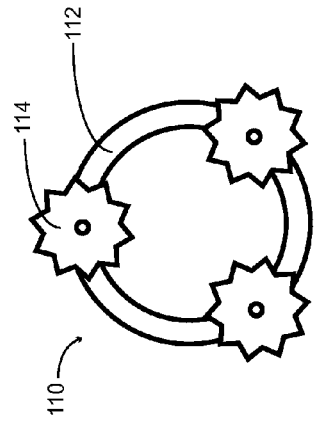
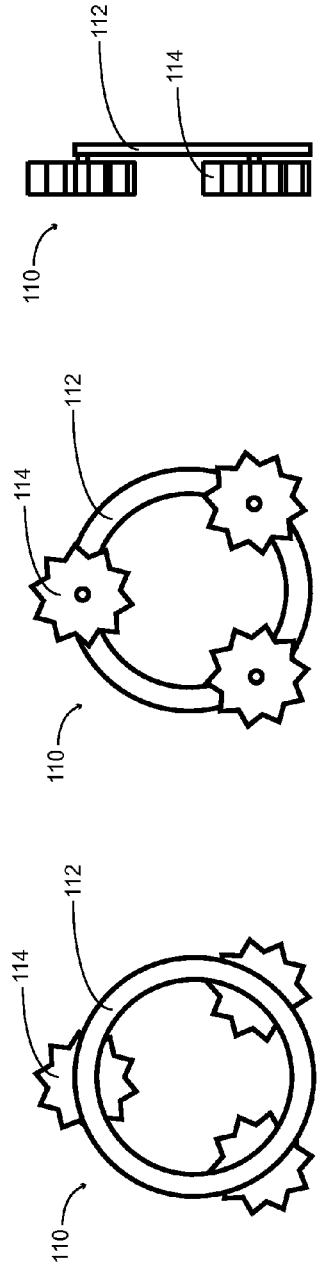

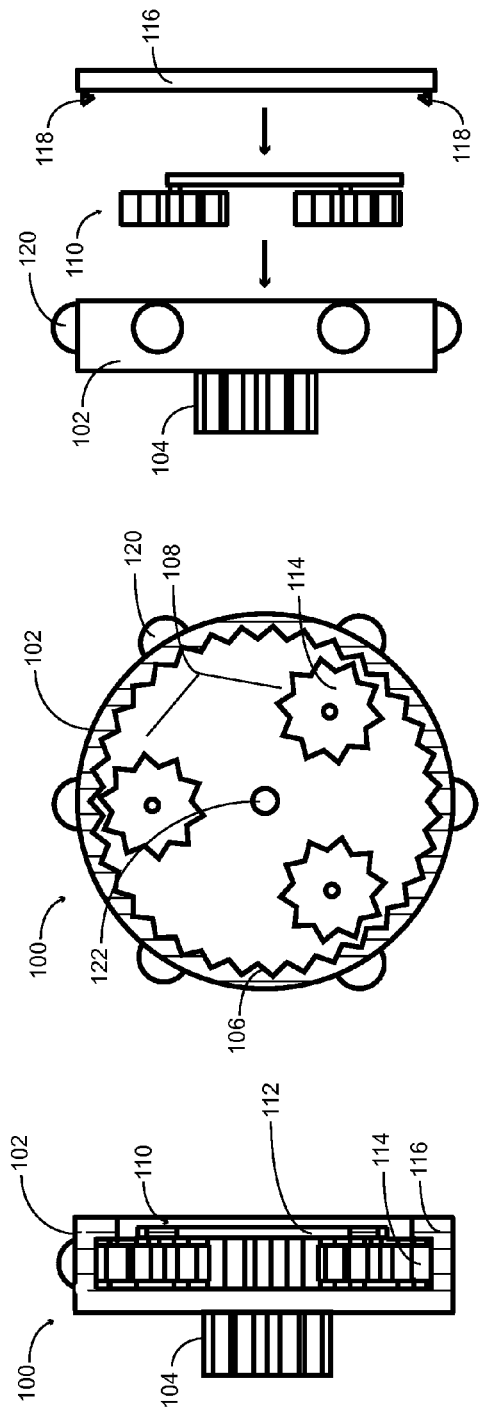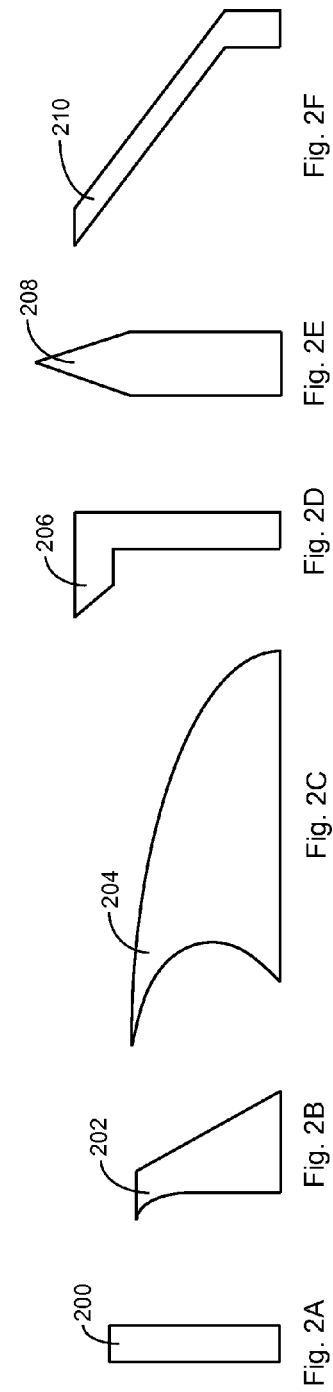

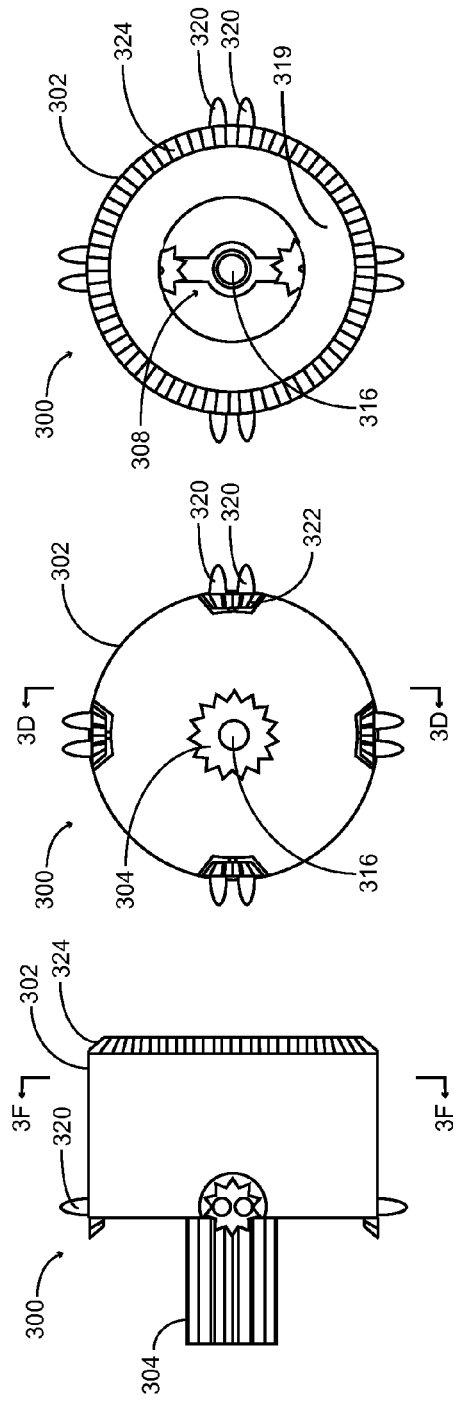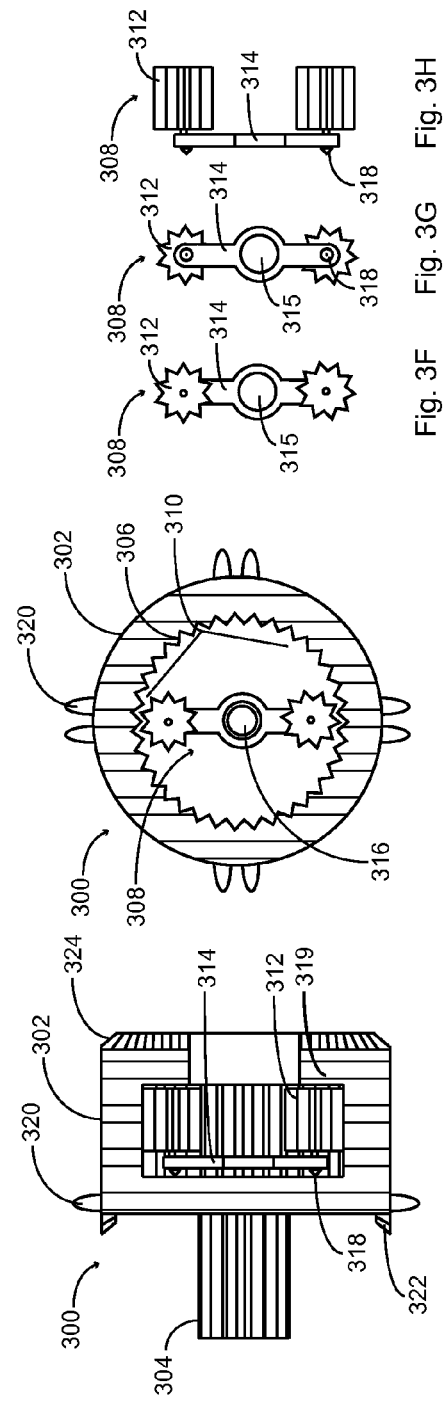

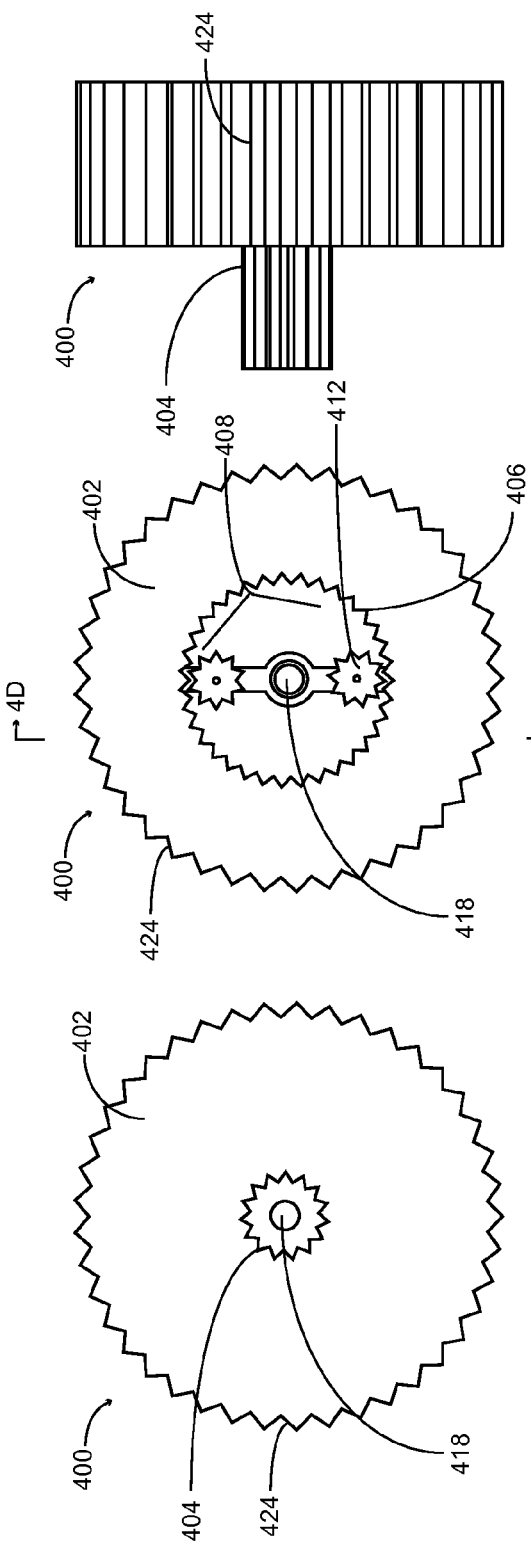

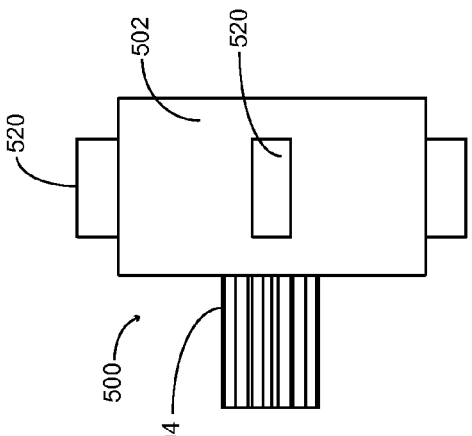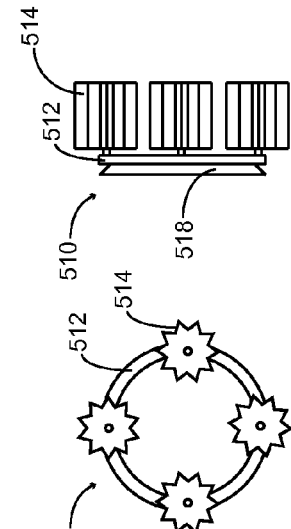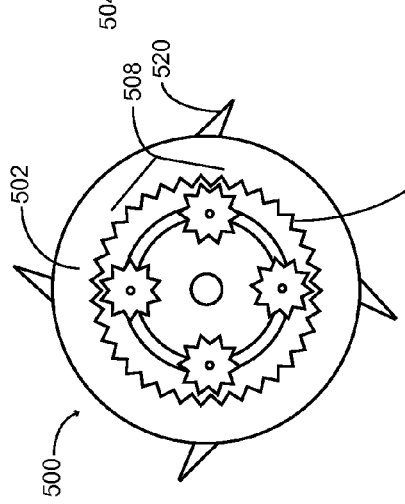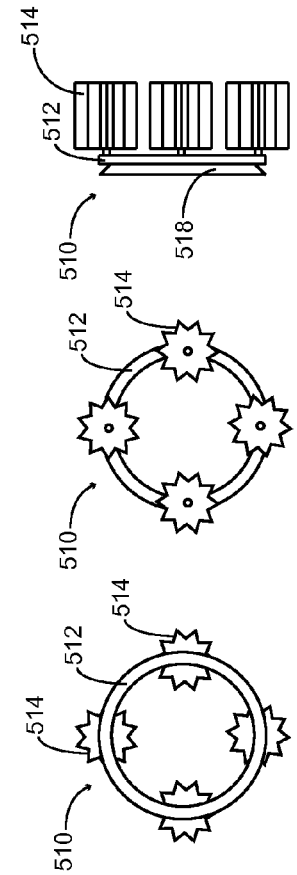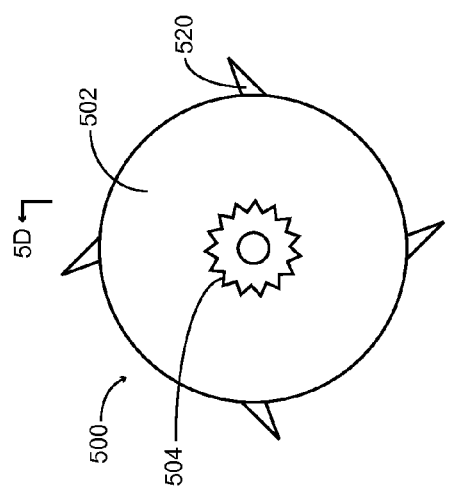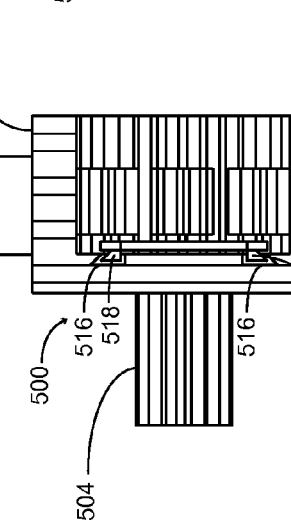

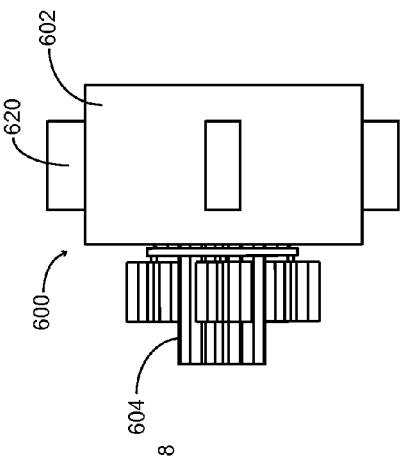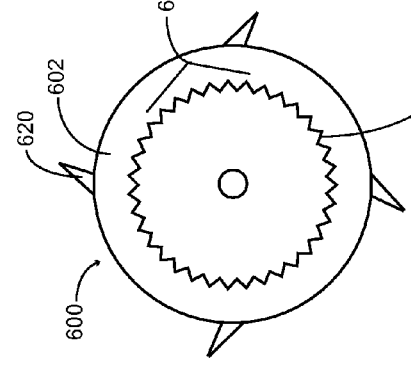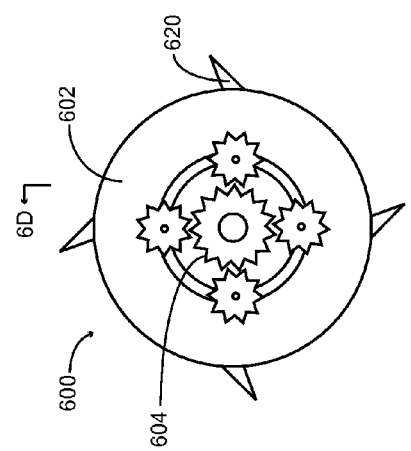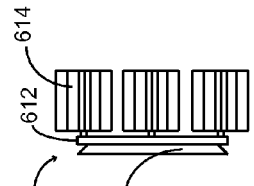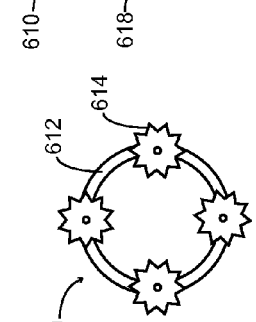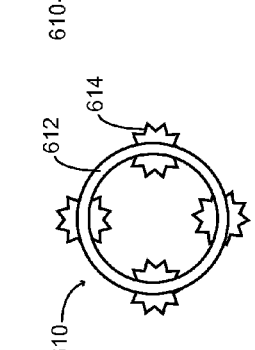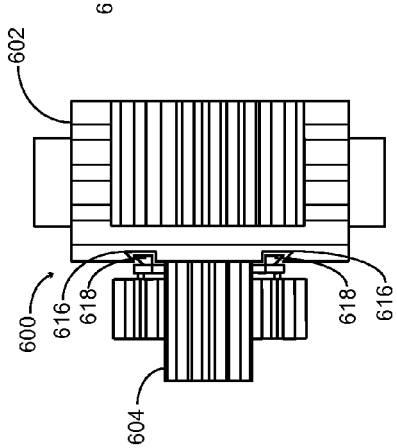

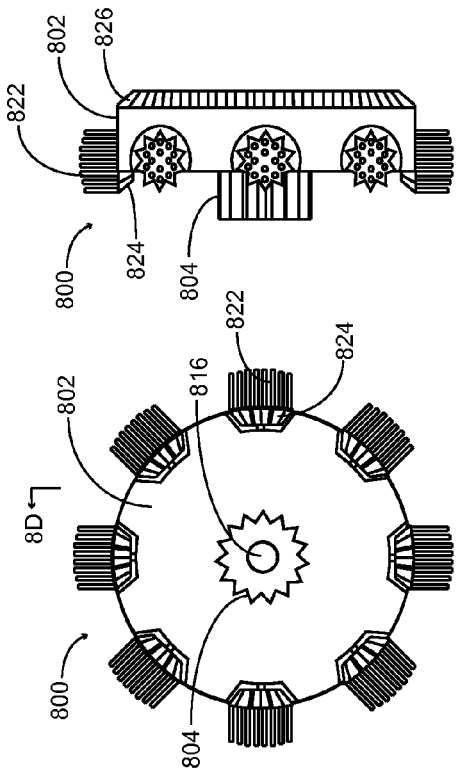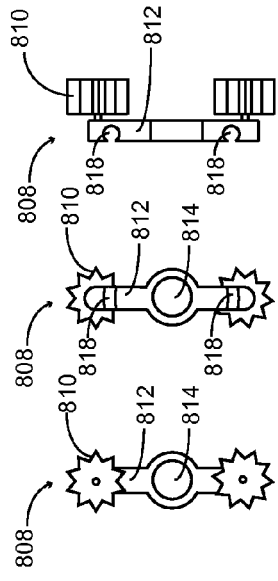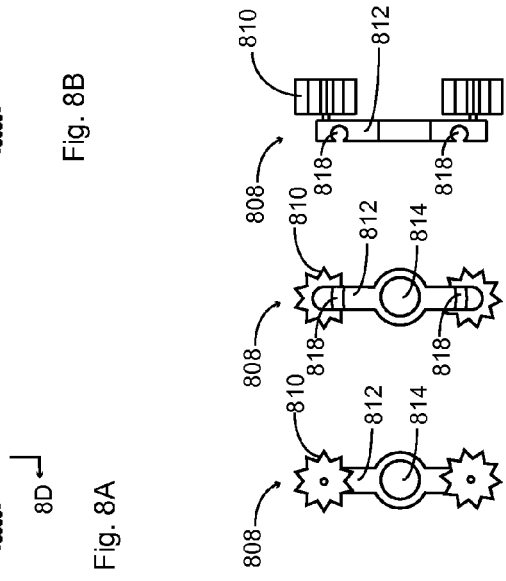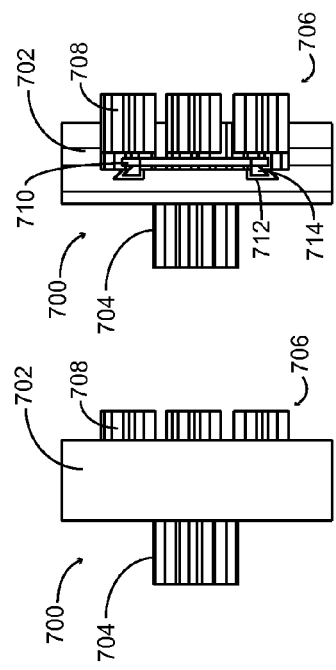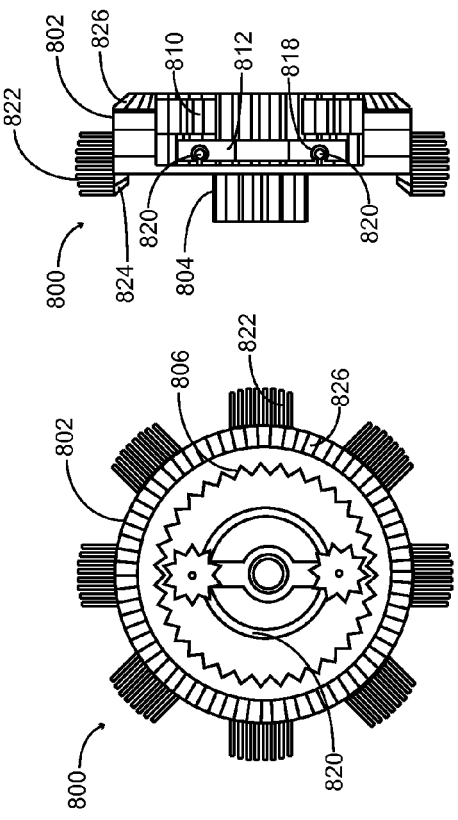

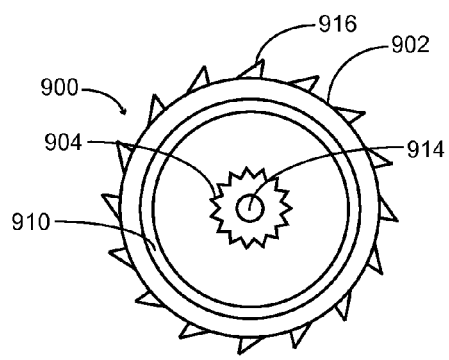
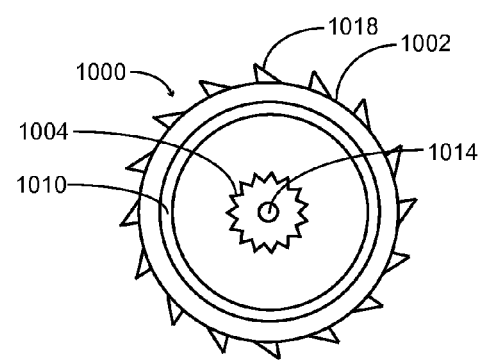
Fig. 9A
Fig. 10A
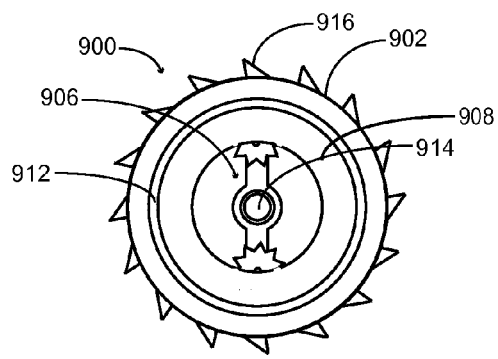
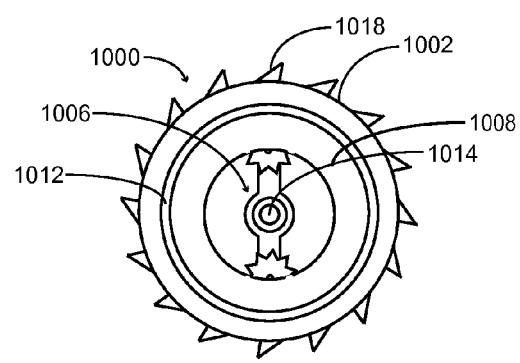
Fig. 9B
Fig. 10B
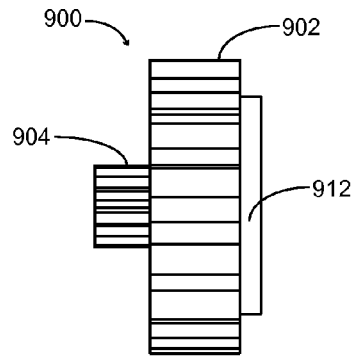
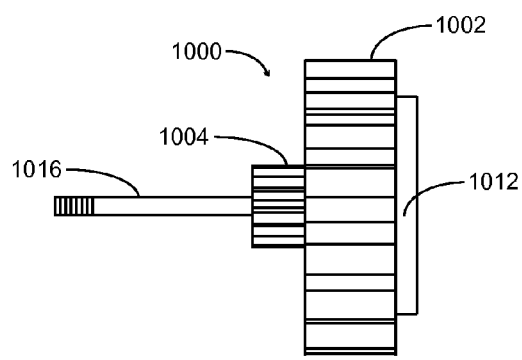
Fig. 9C
Fig. 10C

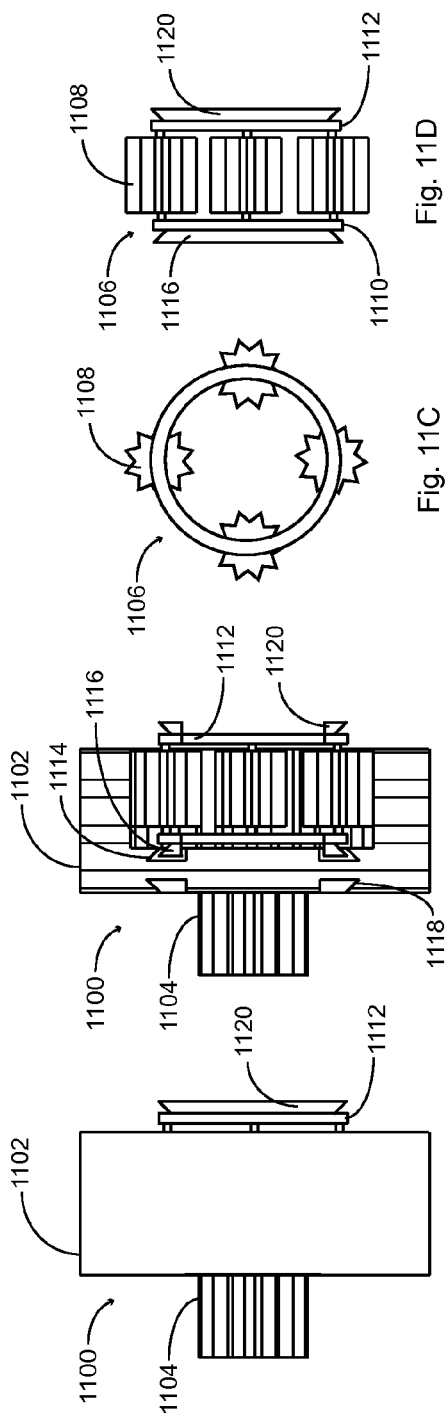

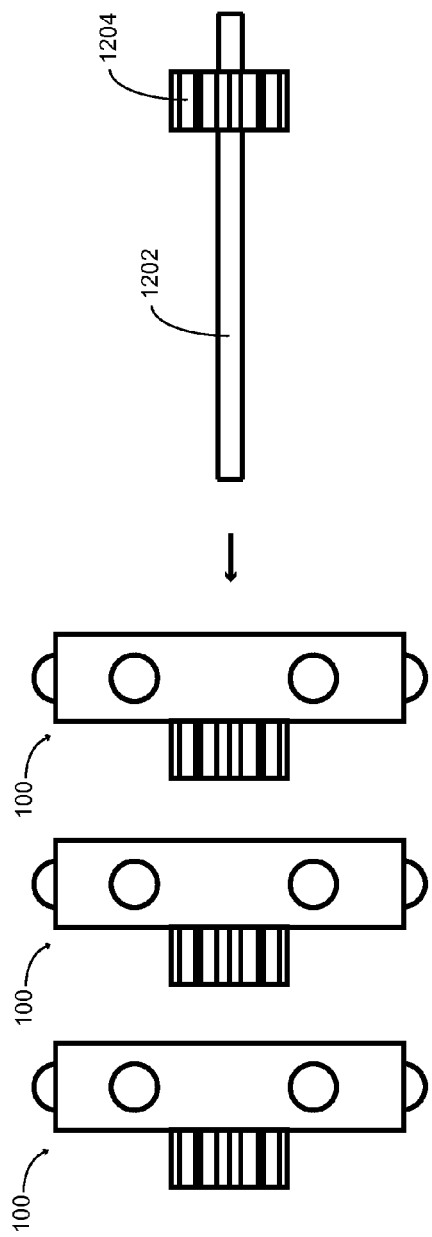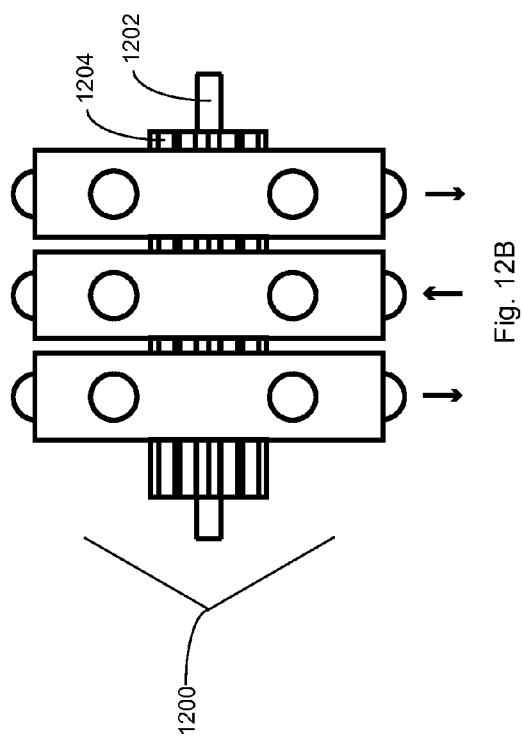
Fig. 12A
Fig. 12B

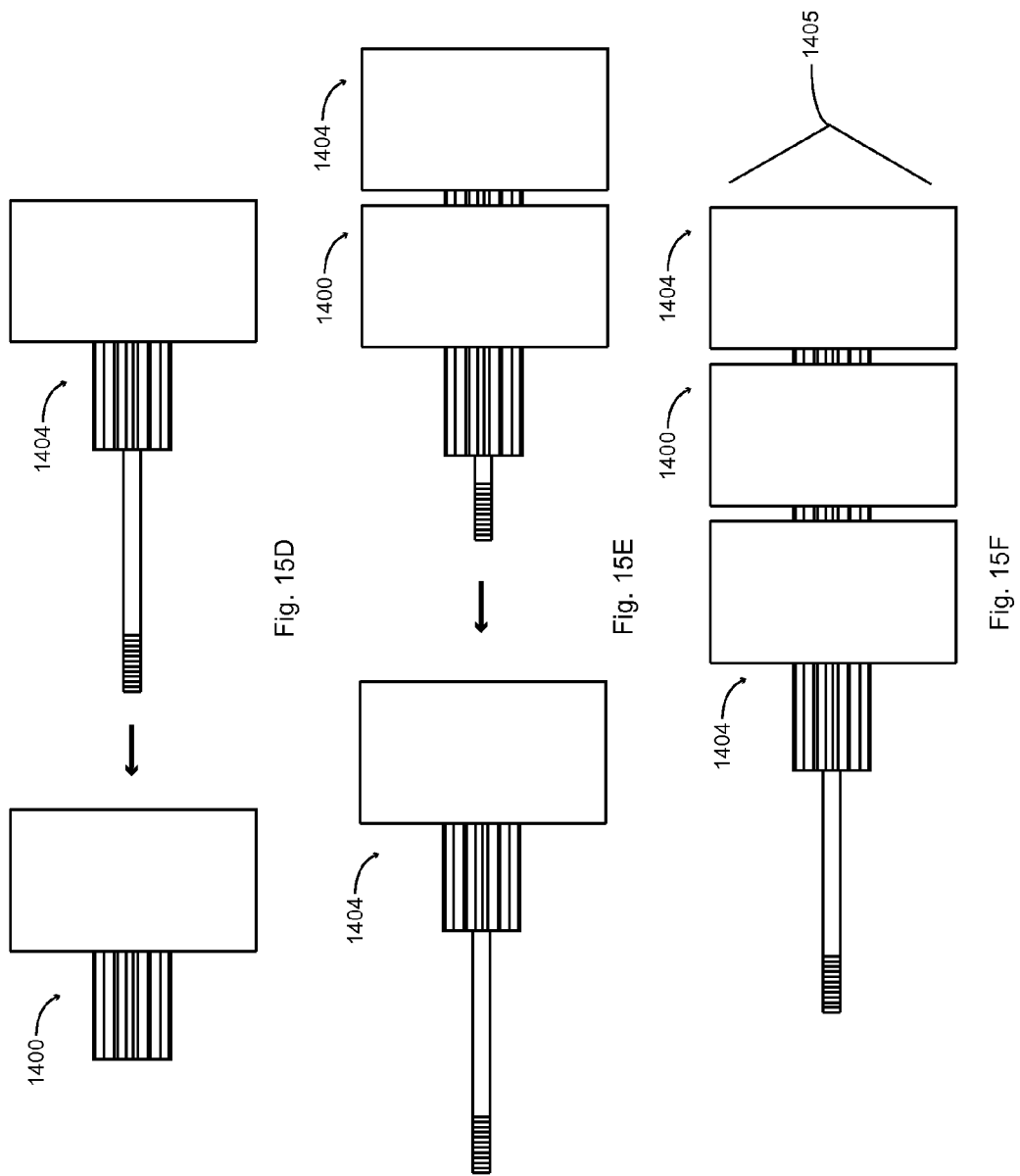

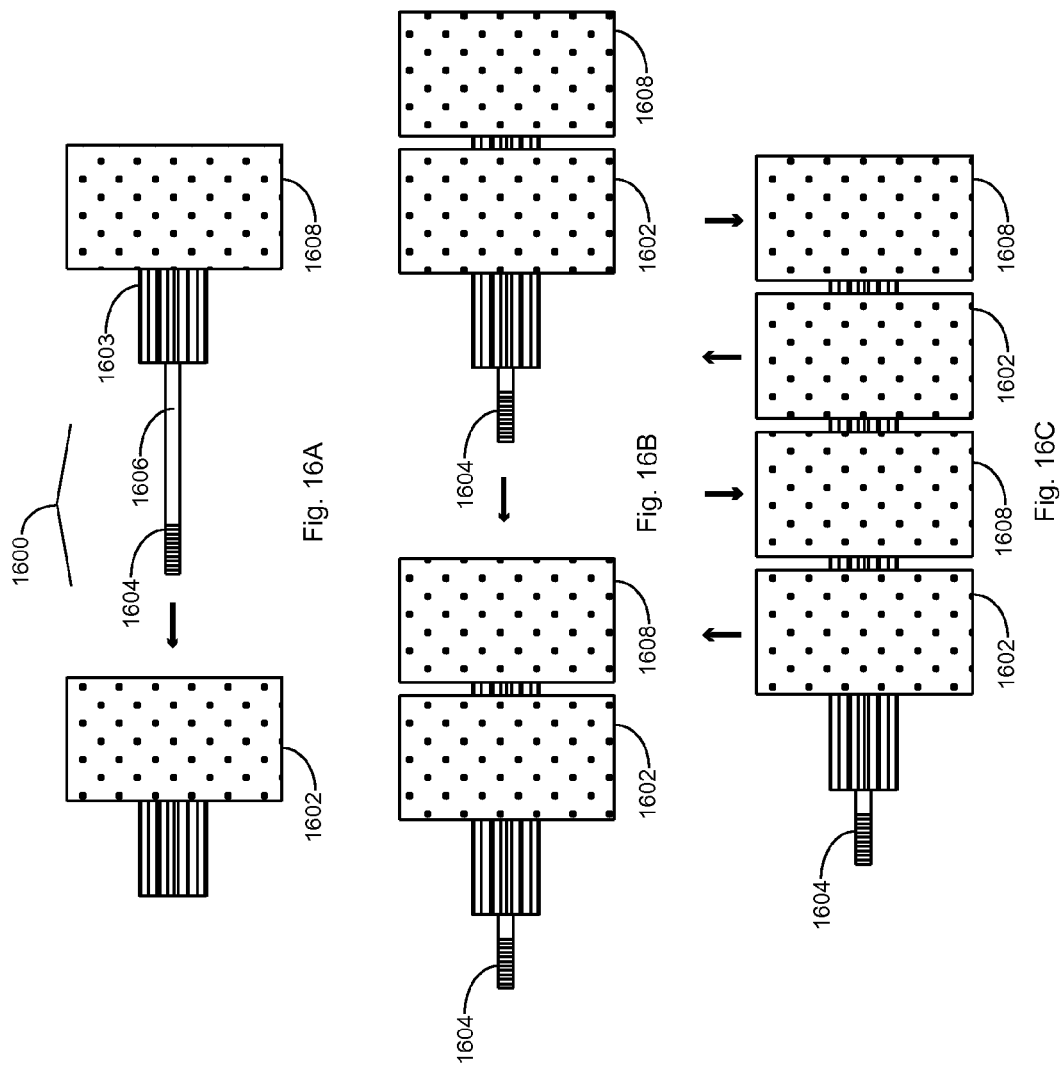

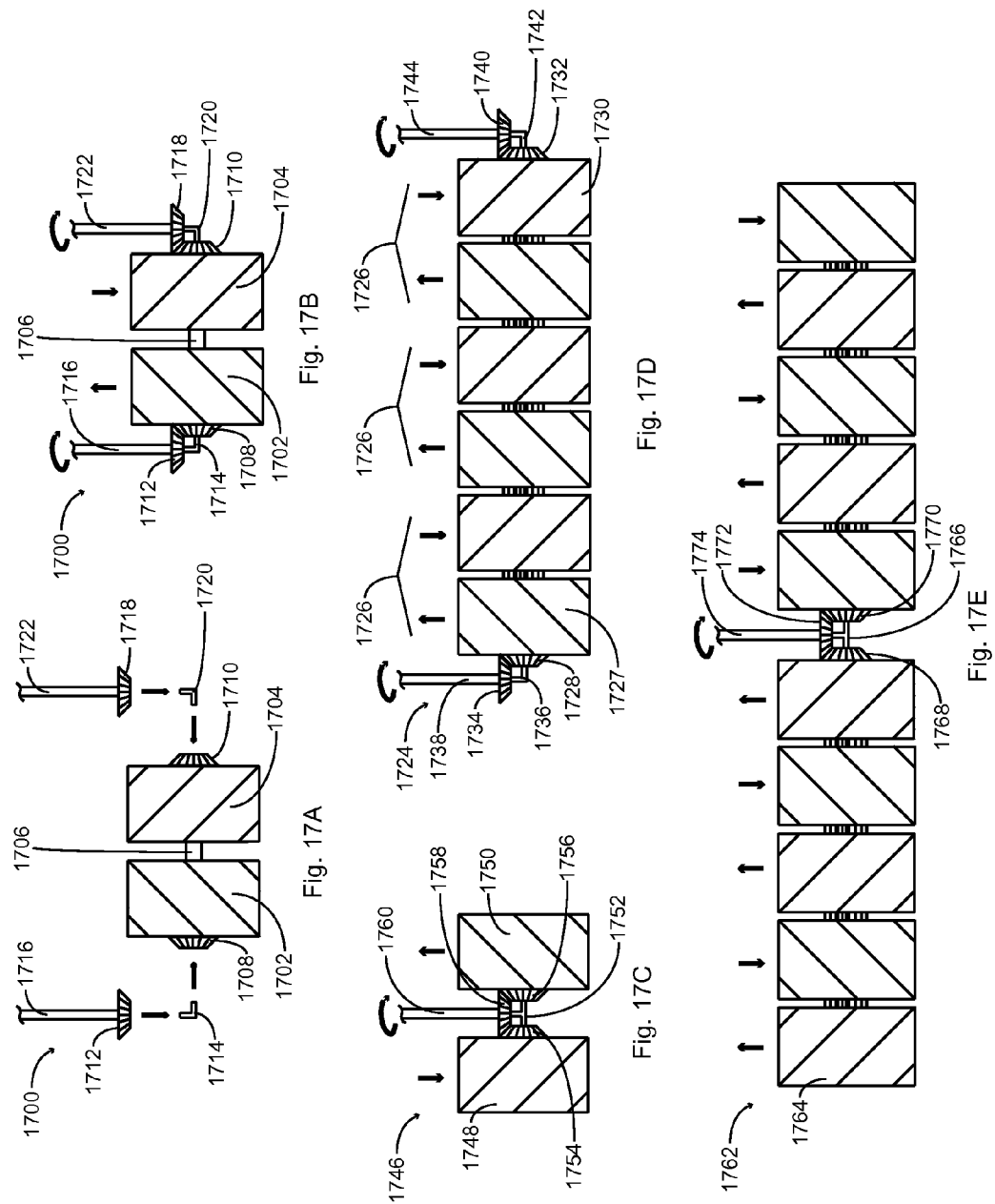

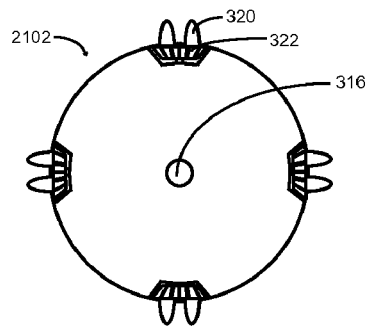
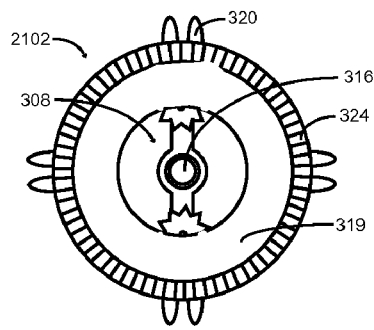
Fig. 21A  Fig. 21B
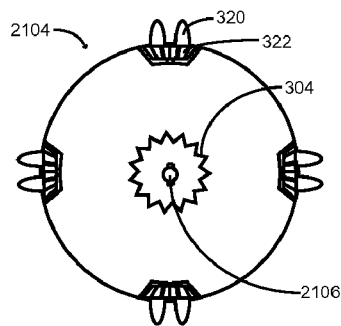
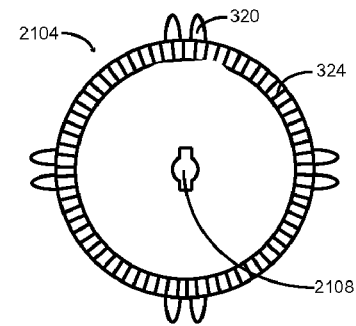
Fig. 21C  Fig. 21D
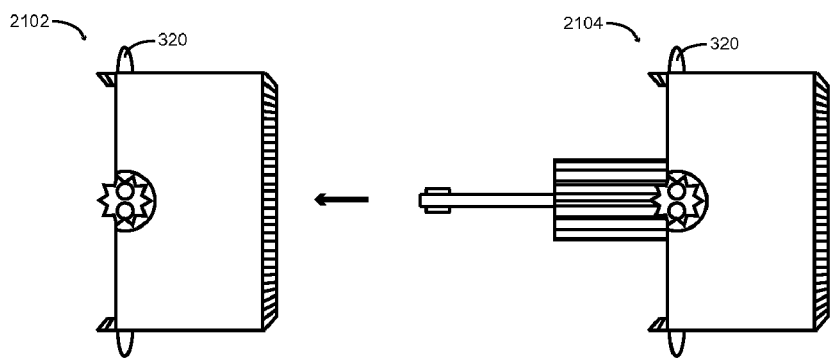
Fig. 21E
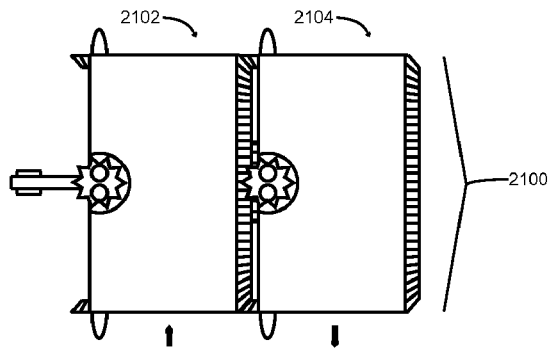
Fig. 21F

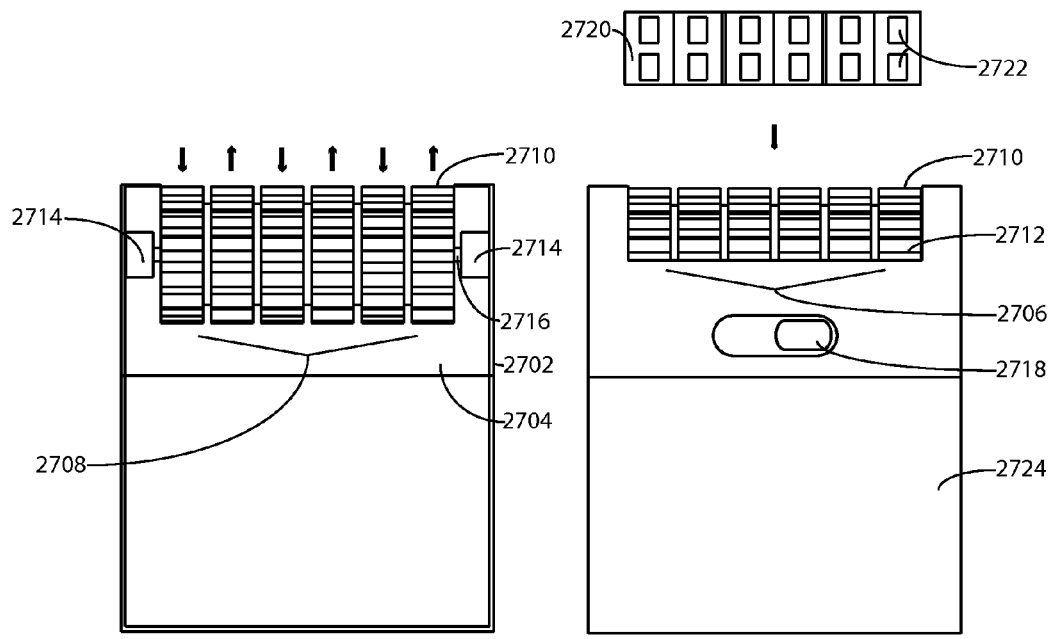
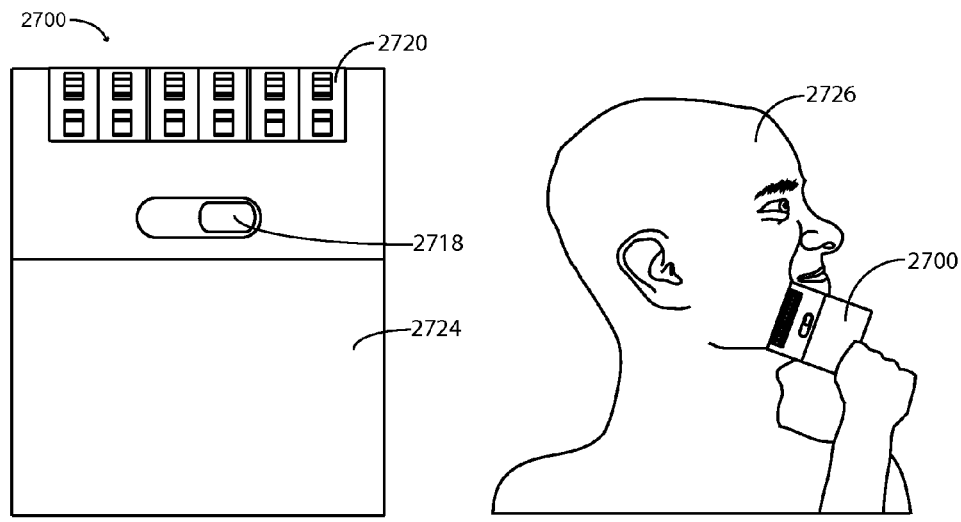
Fig. 27A  Fig. 27B
Fig. 27C  Fig. 27D

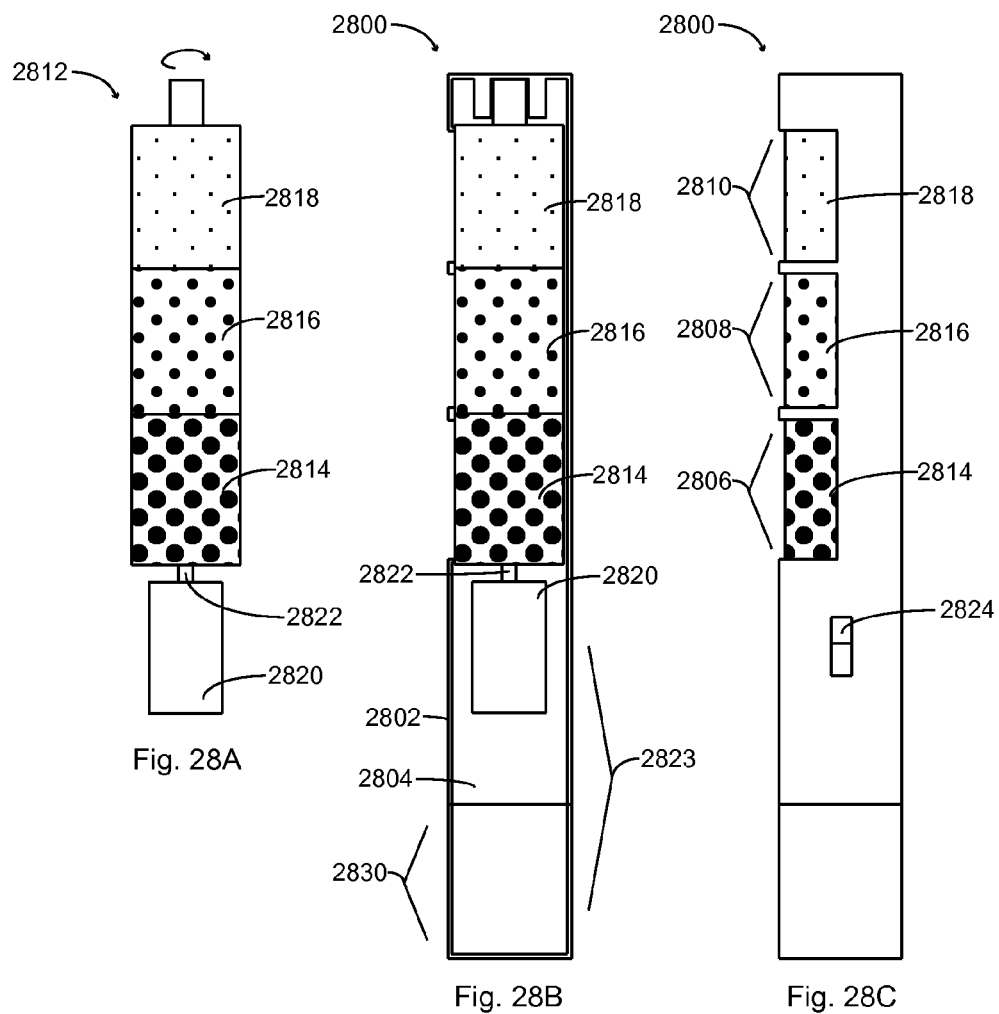
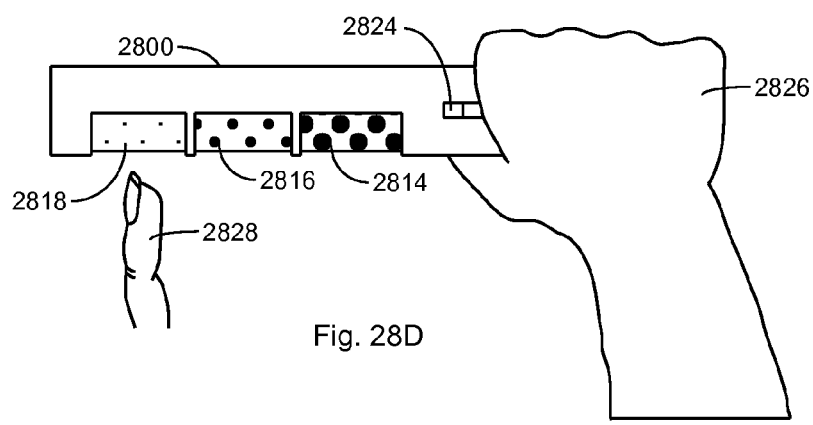

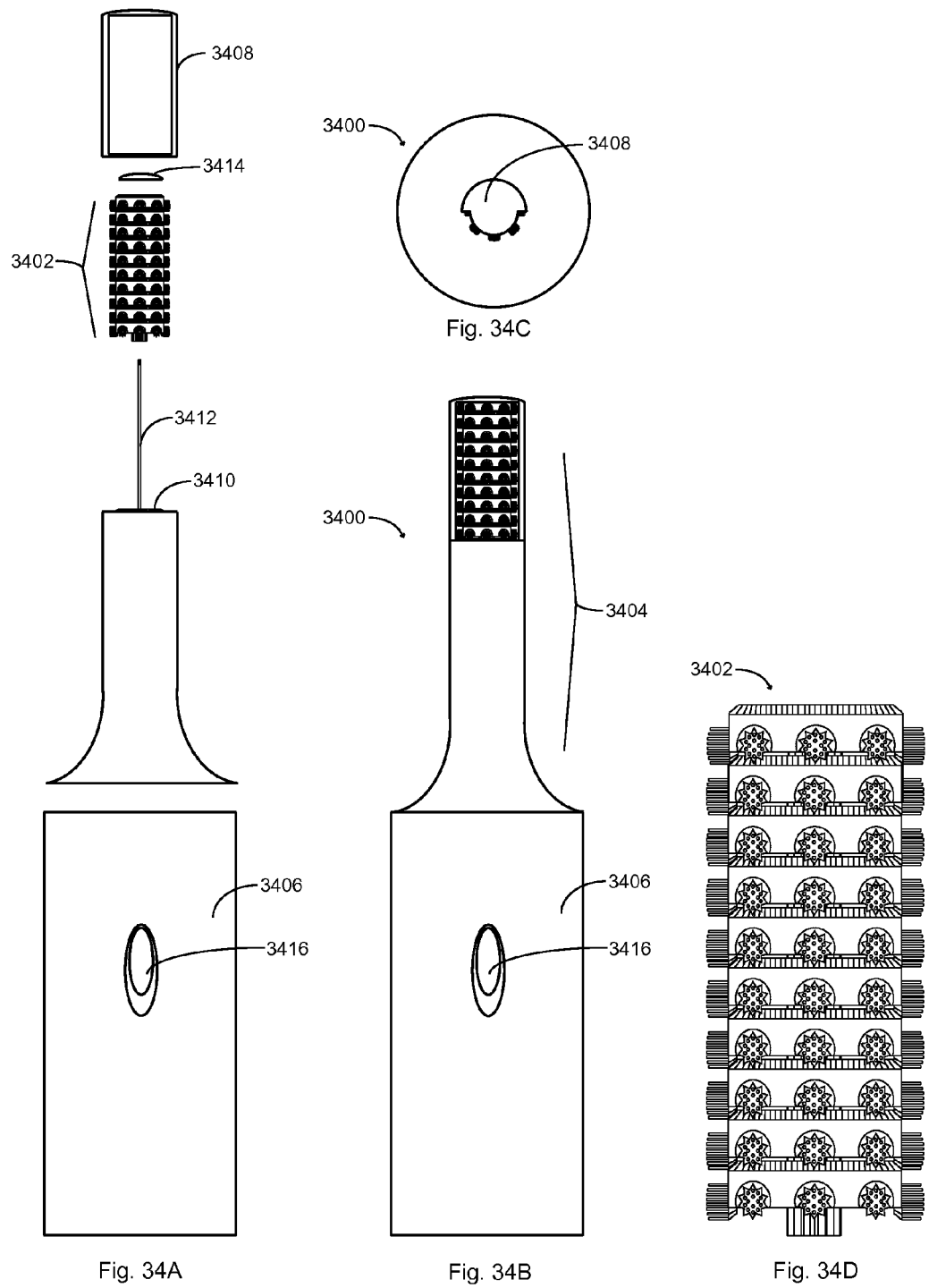

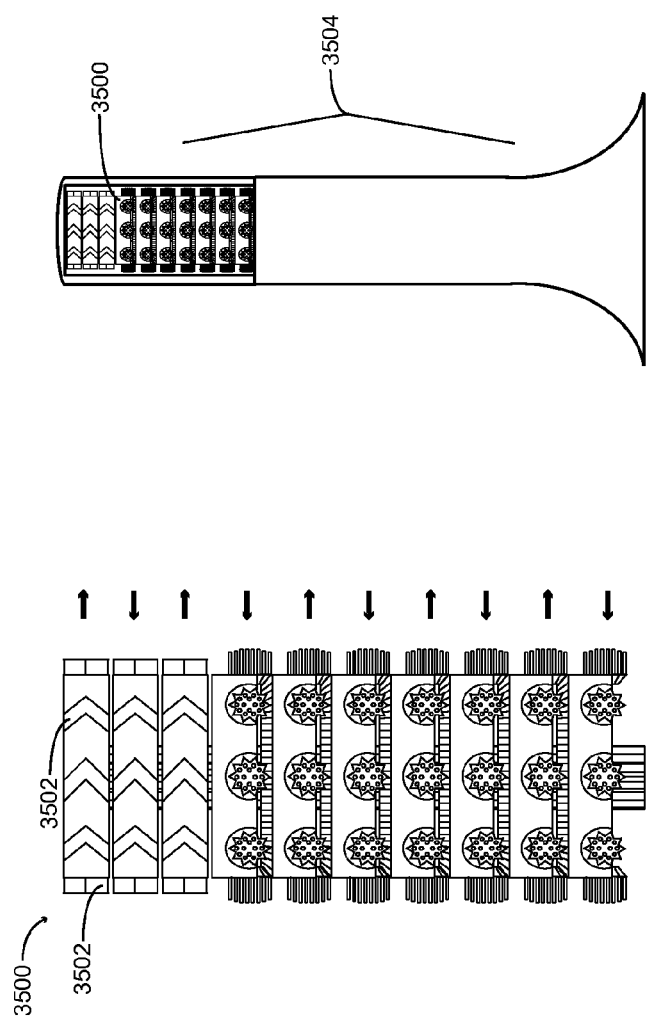
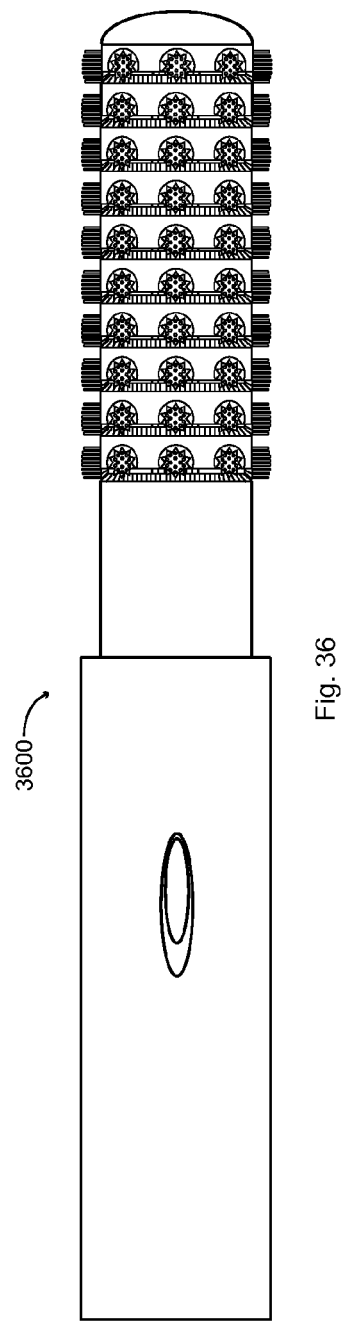
Fig. 35A
Fig. 35B
Fig. 36

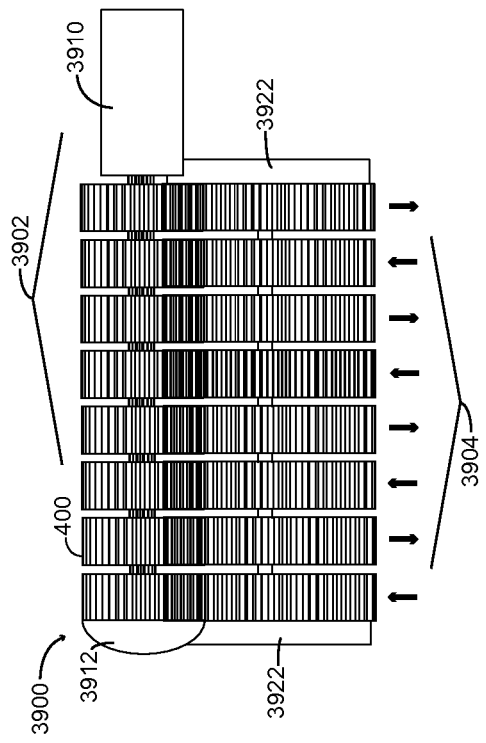
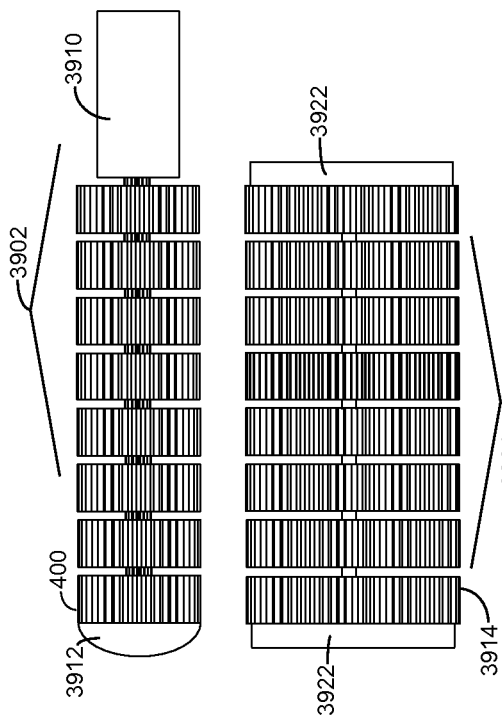
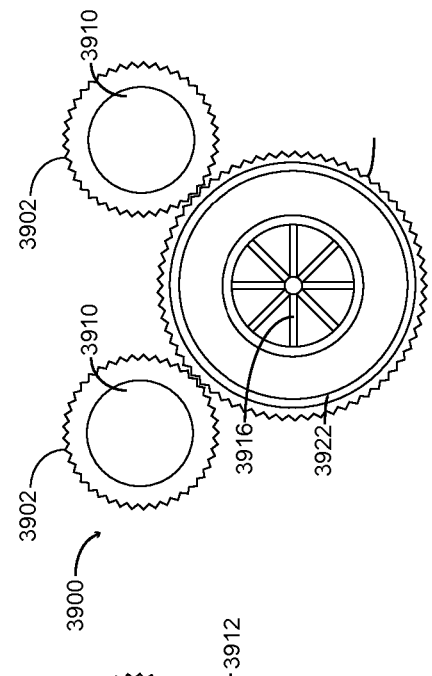
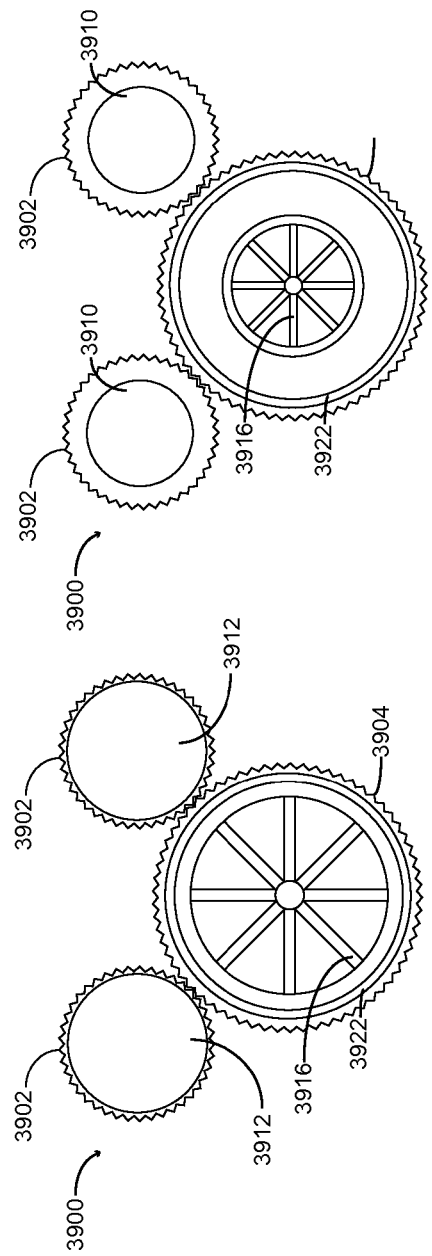

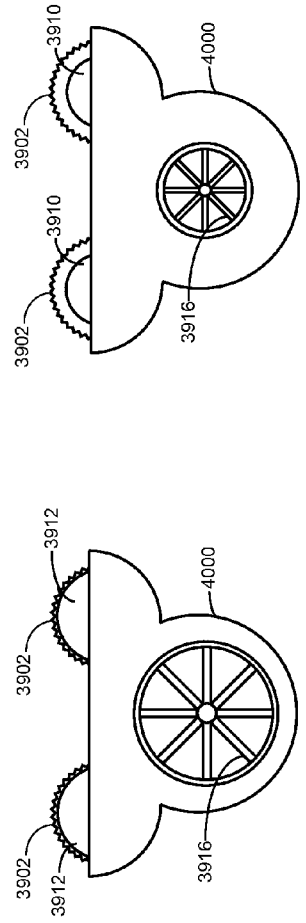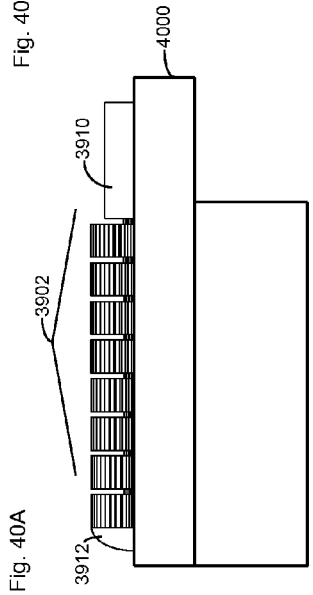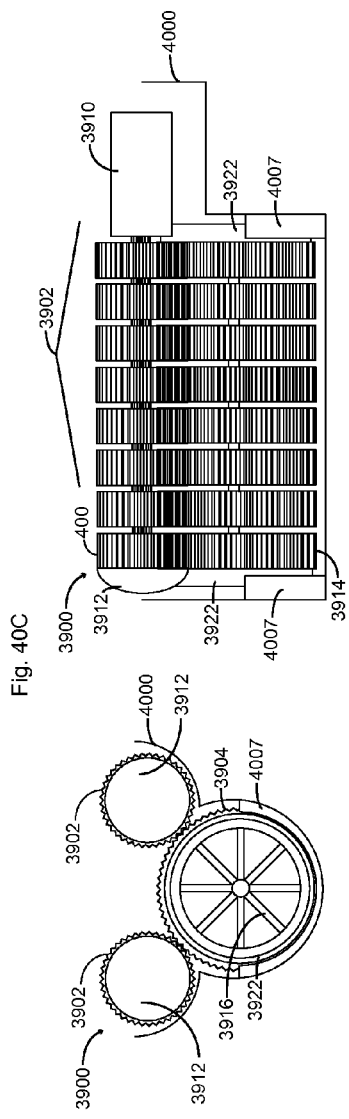

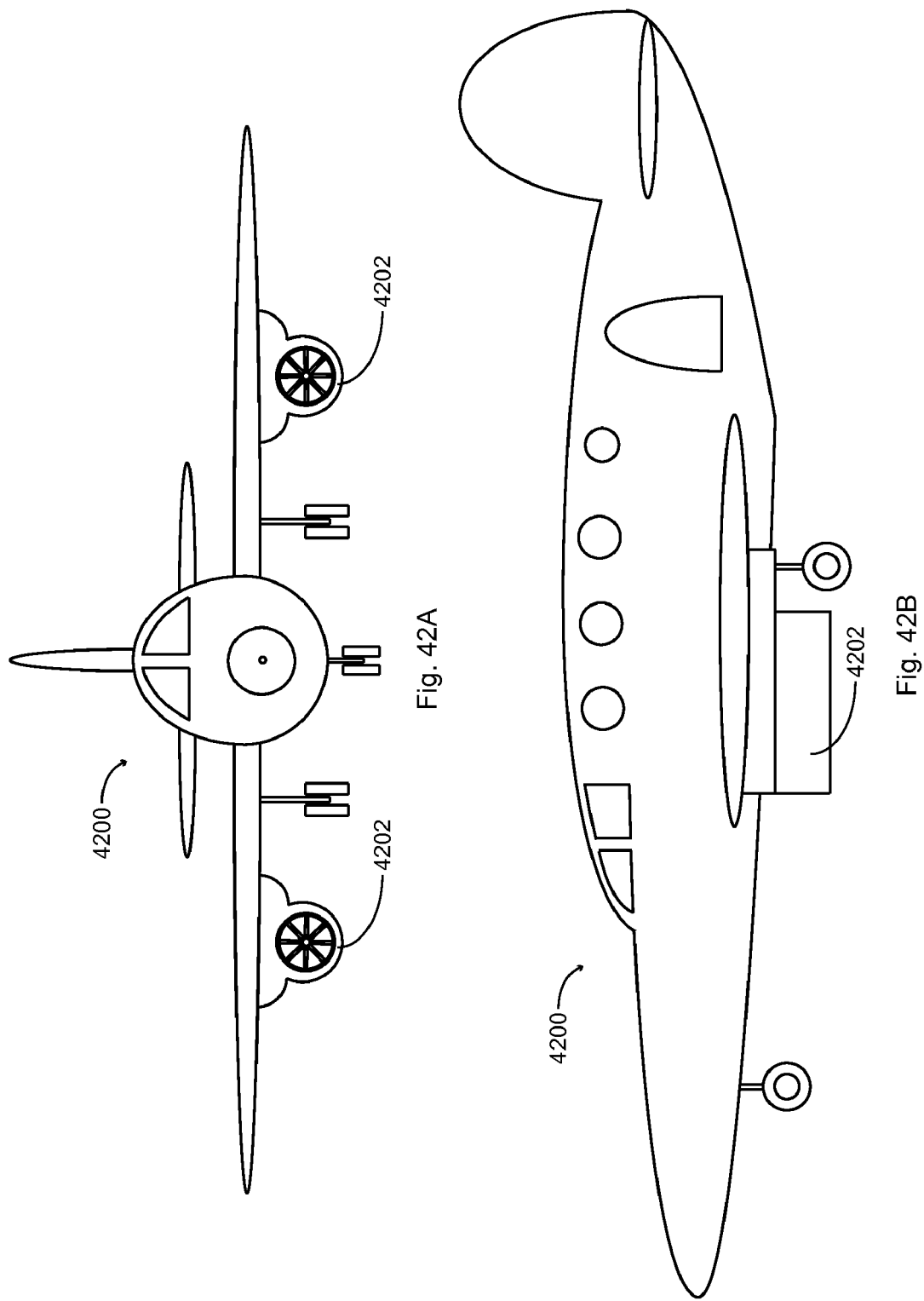

ROTARY UNITS, ROTARY MECHANISMS, AND RELATED APPLICATIONS

CROSS-REFERENCE TO RELATED APPLICATIONS

This application claims the benefit of priority from U.S. Provisional Patent Application No. 61/104,748, entitled "ROTARY UNITS, MECHANISMS, AND RELATED DEVICES", filed on Oct. 12, 2008 and International Application No. PCT/US09/60386, entitled "ROTARY UNITS, ROTARY MECHANISMS, AND RELATED APPLICATIONS", filed on Oct. 12, 2009, which are both incorporated by reference in their entirety.

FIELD OF THE INVENTION

The invention relates generally to mechanical, electrical, or electromechanical devices, and provides rotary units, rotary mechanisms, methods, and related devices and other applications that are useful for a wide variety of purposes.

BACKGROUND OF THE INVENTION

Electromechanical devices are ubiquitous. Some of these devices include rotating components and are used in many different applications. Gardening tools such as rotor tillers, for example, typically include rotating rotors having tines, which contact the soil during operation. Many other devices of use in agricultural and construction, among many other fields or applications also utilize various types of rotational components to achieve desired forms of work.

SUMMARY OF THE INVENTION

The invention relates to rotary units and rotary mechanisms that are suitable for use in numerous applications. Rotary units typically include rotational components that are configured to rotate. In some embodiments, for example, multiple rotary units are assembled in rotary mechanisms such that neighboring pairs of rotational components counter-rotate or contra-rotate relative to one another during operation of the rotary mechanisms. Rotational components generally include one or more implements that are structured to perform or effect one or more types of work as the rotational components rotate relative to one another in a given rotary mechanism. In certain embodiments, implements are configured to rotate and/or to effect the movement of other components as rotational components rotate. These and many other aspects will be apparent upon a complete review of this disclose.

In one aspect, the invention provides a rotary unit that includes at least one rotational component comprising at least a first gear component, at least one gear structure receiving area that is configured to receive one or more gear structures or components thereof, and at least a second gear component disposed at least proximal to the gear structure receiving area. The rotary unit also includes at least one gear structure comprising at least one support component and at least one third gear component rotatably coupled to the support component. The third gear component is configured to operably engage the second gear component when the gear structure is at least partially disposed in the gear structure receiving area. In addition, the first gear component is configured to operably engage one or more third gear components of at least one other rotary unit when the rotary unit is disposed proximal to the other rotary unit. In some embodiments of the rotary units of the invention, the rotational component is configured to receive at least one drive mechanism or a portion thereof. In certain embodiments, the other rotary unit operably engages the rotary unit. To further illustrate, in certain embodiments, at least two other rotary units operably engage the rotary unit.

Typically, the rotary units or mechanisms of the invention include one or more implements that can be used or adapted for use in many different applications. In certain embodiments, for example, at least one surface of a rotational component comprises at least one implement. Optionally, a rotational component comprises at least one implement that is configured to effect the movement of one or more other components (e.g., a propeller component or the like) when the rotational component rotates and the implement operably engages the other components. In certain embodiments, rotary units or mechanisms include at least one implement rotatably coupled to a rotation component, which implement is configured to operably engage one or more gear components of one or more other rotational components. To illustrate, in some embodiments, the rotary units or mechanisms of the invention include one or more gear components that are configured to operably engage one or more implements rotatably coupled to one or more other rotational components. In some embodiments, a rotary unit or a related rotary mechanism of the invention includes at least one implement rotatably coupled to a rotational component. In these embodiments, the implement is optionally configured to operably engage one or more gear components of at least one other rotary unit when the rotary unit is disposed proximal to the other rotary unit such that the implement rotates when at least the rotational component and the other rotary unit rotate relative to one another. Optionally, at least one implement is disposed in, on and/or extending from at least one surface of a rotational component. In some embodiments, for example, implements include one or more of, e.g., a blade, a razor, a prong, a peg, a claw, a tine, a chain, a stake, a column, a pillar, an arch, a bracket, a gear component, a bristle, a plume, an abrasive component, an elastomeric component, a nail filing component, a nail buffing component, a hair cutting component, a massaging component, a post, etc. To further illustrate, at least a portion of an implement comprises at least one cross-sectional shape selected from, e.g., a circle, an oval, a square, a rectangle, a trapezoid, an irregular n-sided polygon, a regular n-sided polygon, and the like.

In some embodiments, the rotary units or mechanisms of the invention include a rotational component that comprises a retaining mechanism that retains a gear structure at least partially in a gear structure receiving area. For example, a rotational component optionally comprises at least one substantially or partially circular indentation and the gear structure comprises at least one projection configured to at least partially fit and move within the substantially or partially circular indentation to retain the gear structure at least partially within the gear structure receiving area when the second and third gear components operably engage one another. To further illustrate, in certain embodiments, the gear structure comprises at least one substantially or partially circular indentation and the rotational component comprises at least one projection configured to at least partially fit and move within the substantially or partially circular indentation to retain the gear structure at least partially within the gear structure receiving area when the second and third gear components operably engage one another. In certain embodiments, the rotary units or mechanisms of the invention comprises at least one retaining mechanism structured to retain a gear structure at least partially in the gear structure receiving area.

In some embodiments of the rotary units or mechanisms of the invention, a first gear component is disposed in a substantially fixed position relative to a second gear component. In certain of these embodiments, the second gear component is disposed at least partially in a gear structure receiving area. In some of these embodiments, the second gear component is disposed in a substantially fixed position relative to the first gear component.

In certain embodiments of the rotary units or mechanisms of the invention, a gear structure is at least partially disposed in a gear structure receiving area. In some embodiments, for example, at least a portion of the gear structure is configured to rotate relative to a rotational component. Optionally, the gear structure is rotatably coupled to a rotational component.

In certain embodiments, a device or vehicle includes a rotary unit or mechanism of the invention. In some embodiments, the device is selected from, e.g., a held-held device, a rototiller, a hair cutting device, a massaging device, nail grooming device, a propulsion device, a woodworking device, a lathe, a woodchipping device, a machining device, a dermabrasion device, a medical device, a dental device, a cleaning device, an engine, a snowblower, a nozzle, a food preparation device, a grinder, a pencil sharpener, a lawn mower, a vacuum cleaner, a hair dryer, a plumbing device, a weapon, a surfboard, a scuba device, a component thereof, a combination thereof, etc. In certain embodiments, the vehicle includes a farming vehicle, a mining vehicle, a construction vehicle, a submarine, an aircraft, a marine vehicle, a boat, a personal watercraft, a military vehicle, or the like.

In certain embodiments of the rotary units or mechanisms of the invention, a rotational component comprises at least first and second surfaces. In some of these embodiments, the first and second surfaces substantially oppose one another. Optionally, the first gear component is disposed on and/or extends from the first surface. In some embodiments, the second gear component is disposed on and/or extends from the second surface.

In another aspect, the invention provides a rotary unit that includes at least one rotational component comprising at least first and second gear components and at least one gear structure receiving area, wherein the first gear component substantially fixedly extends from a first surface of the rotational component, wherein the first gear component is configured to operably engage one or more other gear components, wherein the second gear component substantially fixedly extends from a second surface of the rotational component, wherein the second gear component communicates with the gear structure receiving area, wherein the gear structure receiving area is configured to receive one or more gear structures or components thereof, wherein the first and second surfaces substantially oppose one another, and wherein at least one surface of the rotational component comprises at least one implement. In addition, the rotary unit includes at least one gear structure comprising at least one support component and at least a third gear component coupled to the support component, wherein the gear structure is at least partially disposed within the gear structure receiving area, wherein the gear structure is configured to rotate relative to the rotational component, wherein the third gear component is configured to operably engage the second gear component, and wherein the gear structure and/or the rotational component comprises at least one retaining mechanism or a portion thereof that is configured to retain the gear structure at least partially within the gear structure receiving area. Optionally, the other gear components comprise one or more third gear components of at least one other rotary unit (i.e., a different rotary unit). In some embodiments, the rotational component is configured to receive at least one drive mechanism or a portion thereof. In some of these embodiments, the third gear component is rotatably coupled to (e.g., is capable of rotating relative to) the support component.

In another aspect, the invention includes a rotary unit that comprises at least one rotational component comprising at least first and second sides that substantially oppose one another and at least one drive mechanism component receiving area that is configured to receive at least one drive mechanism component, wherein at least a first gear component is substantially coaxially and substantially fixedly positioned proximal to an inner region of the first side, wherein at least a second gear component is substantially coaxially and substantially fixedly positioned proximal to an outer region of the second side, wherein the second gear component defines at least a portion of at least one gear structure receiving area, wherein the gear structure receiving area is configured to receive one or more gear structures or components thereof, and wherein at least one surface of the rotational component comprises at least one implement. In some embodiments, the rotary unit includes at least one gear structure comprising at least one support component and at least a third gear component rotatably coupled to the support component, wherein the gear structure is at least partially disposed within the gear structure receiving area, wherein the gear structure is configured to rotate relative to the rotational component, wherein the third gear component is configured to operably engage the second gear component such that when the third gear component rotates in a first direction the rotational component rotates in the first direction, and wherein the first gear component is configured to operably engage the third gear component of at least one other rotary unit when the first gear component is disposed proximal to the other rotary unit such that when the first gear component rotates in the first direction the rotational component of the other rotary unit rotates in a second direction that is substantially opposite from the first direction; and at least one retaining mechanism that is configured to retain the gear structure at least partially within the gear structure receiving area. In some of these embodiments, the rotational component is configured to rotate about the drive mechanism component when the drive mechanism component receiving area receives the drive mechanism component. Optionally, the rotational component is substantially fixedly attachable to the drive mechanism component when the drive mechanism component receiving area receives the drive mechanism component such that the rotational component rotates in the same direction as the drive mechanism component when the drive mechanism component rotates. In some embodiments, the drive mechanism component receiving area receives the drive mechanism component. In certain embodiments, the rotational component is fabricated integral with the drive mechanism component.

In another aspect, the invention provides a rotary unit or rotary mechanism that includes at least one rotational component comprising at least first and second sides that substantially oppose one another and at least one drive mechanism component receiving area that is configured to receive at least one drive mechanism component, wherein at least a first gear component is substantially coaxially and substantially fixedly positioned proximal to an inner region of the first side, wherein at least a second gear component is substantially coaxially and substantially fixedly positioned proximal to an outer region of the second side, wherein the second gear component defines at least a portion of at least one gear structure receiving area, wherein the gear structure receiving area is configured to receive one or more gear structures or components thereof, and wherein at least one surface of the rotational component comprises at least one implement. Typically, the rotary unit includes at least one gear structure comprising at least one support component and at least a third gear component rotatably coupled to the support component, wherein the gear structure is at least partially disposed within the gear structure receiving area, wherein the gear structure is configured to rotate relative to the rotational component, wherein the third gear component is configured to operably engage the second gear component such that when the third gear component rotates in a first direction the rotational component rotates in the first direction, and wherein the first gear component is configured to operably engage the third gear component of at least one other rotary unit when the first gear component is disposed proximal to the other rotary unit such that when the first gear component rotates in the first direction, the rotational component of the other rotary unit rotates in a second direction that is substantially opposite from the first direction. The rotary unit typically includes means for retaining the gear structure at least partially within the gear structure receiving area.

In another aspect, the invention provides a rotary unit or rotary mechanism that includes a rotary unit comprising at least one rotational component comprising at least first and second gear components and at least one gear structure receiving area, wherein the first gear component substantially fixedly extends from a first surface of the rotational component, wherein the second gear component substantially fixedly extends from a second surface of the rotational component, wherein the first and second surfaces substantially oppose one another, wherein the second gear component communicates with the gear structure receiving area, wherein the gear structure receiving area is configured to receive one or more gear structures or components thereof, and wherein at least one surface of the rotational component comprises at least one implement. In some of these embodiments, the rotary unit or rotary mechanism includes at least one gear structure comprising at least one support component and at least a third gear component rotatably coupled to the support component, wherein the gear structure and/or the rotational component comprises at least one retaining mechanism or a portion thereof that is configured to retain the gear structure proximal to the first surface of the rotational component, wherein the gear structure or a component thereof is configured to rotate relative to the rotational component, wherein the first gear component is configured to operably engage the third gear component, and wherein the third gear component is configured to operably engage one or more other gear components when the third gear component is disposed proximal to the other gear components. To illustrate, the other gear components comprise one or more second gear components of at least one other rotary unit. In some embodiments, the rotational component is configured to receive at least one drive mechanism or a portion thereof.

In another aspect, the invention provides a rotary unit or rotary mechanism that includes a rotary unit comprising least one rotational component comprising at least a first gear component, at least one gear structure receiving area that is configured to receive one or more gear structures or components thereof, and at least a second gear component disposed at least proximal to the gear structure receiving area. The rotary unit also includes at least one gear structure comprising at least one support component and at least a third gear component rotatably coupled to the support component, wherein the third gear component is configured to operably engage the second gear component when the gear structure is at least partially disposed in the gear structure receiving area and wherein the third gear component is configured to operably engage one or more first gear components of at least one other rotary unit when the rotary unit operably engages the other rotary unit, or wherein the third gear component is configured to operably engage the first gear component when the third gear component is disposed proximal to the first gear component and wherein the third gear component is configured to operably engage one or more second gear components of at least one other rotary unit when the rotary unit operably engages the other rotary unit.

In another aspect, the invention provides a rotary unit or rotary mechanism comprising at least a first rotational component that comprises at least first and second surfaces, wherein the first surface comprises at least a first gear component and the second surface comprises at least a second gear component, which first and second gear components are substantially fixed relative to one another, wherein the first gear component is configured to operably engage one or more third gear components that are configured to operably engage one or more second gear components of at least a second rotational component when the first rotational component is disposed proximal to the second rotational component such that when the first rotational component rotates in a first direction, the second rotational component rotates in a second direction, and wherein the second gear component is configured to operably engage one or more third gear components that are configured to operably engage one or more first gear components of at least a third rotational component when the first rotational component is disposed proximal to the third rotational component such that when the first rotational component rotates in the first direction, the third rotational component rotates in the second direction.

In another aspect, the invention provides a rotary unit or rotary mechanism comprising at least one rotational component comprising at least a second gear component that substantially fixedly extends from a second surface of the rotational component and at least one drive mechanism component receiving area that is configured to receive at least one drive mechanism component, wherein the second gear component is configured to operably engage at least a third gear component such that when the third gear component rotates in a first direction, the rotational component rotates in the first direction.

In another aspect, the invention provides a rotary unit or rotary mechanism comprising at least one rotational component comprising at least first and second surfaces that substantially oppose one another, wherein at least a first gear component substantially fixedly extends from the first surface of the rotational component, which first gear component is configured to operably engage one or more third gear components, wherein at least a first drive mechanism component substantially fixedly extends from the first surface of the rotational component and is substantially coaxially positioned relative to the first gear component, and wherein at least one drive mechanism component receiving area is disposed proximal to the second surface and is configured to receive at least a second drive mechanism component.

In another aspect, the invention provides a rotary unit or rotary mechanism comprising at least one rotational component comprising at least first and second sides; at least a first gear component positioned on the first side of the rotational component, which first gear component is in a substantially fixed position relative to the rotational component; at least one gear structure receiving area positioned on the second side of the rotational component, which gear structure receiving area is configured to receive one or more gear structures; at least a second gear component positioned in and/or proximal to the gear structure receiving area; and, at least one gear structure comprising at least one support component and at least a third gear component rotatably connected to the support component, wherein the gear structure is at least partially disposed in the gear structure receiving area such that the third gear component operably engages the second gear component. Optionally, the rotary unit or the rotary mechanism includes at least one implement extending from at least one surface of the rotational component. In some embodiments, at least one surface of the rotational component comprises at least one implement. In some of these embodiments, the rotary unit or rotary mechanism comprises at least one retaining mechanism structured to retain the gear structure at least partially in the gear structure receiving area. In certain embodiments, at least a portion of the gear structure is configured to rotate relative to the rotational component.

In another aspect, the invention provides a rotary mechanism comprising at least two rotational components that are configured to substantially coaxially rotate relative to one another in which at least one of the rotational components comprises at least one implement. The rotary mechanism also includes at least one counter-rotational mechanism operably coupled to and/or operably engaged with at least first and/or second rotational components, which counter-rotational mechanism is configured to effect substantially simultaneous counter-rotation of at least the first and second rotational components relative to one another when movement of at least a portion of the counter-rotational mechanism is effected. In addition; the rotary mechanism also includes at least one drive mechanism operably coupled to the counter-rotational mechanism and/or at least one of the rotational components, which drive mechanism is configured to effect movement of at least the portion of the counter-rotational mechanism such that the first and second rotational components substantially simultaneously counter-rotate relative to one another. In some embodiments, the rotary mechanisms of the invention include a support structure structured to support at least a portion of the rotational components, the counter-rotational mechanism, and/or the drive mechanism.

The rotational components of the rotary units and rotary mechanisms of the invention include various embodiments. In some embodiments, for example, the rotational components are coupled to one another via a shaft positioned proximal to an axis of rotation. In certain embodiments, the rotary units and rotary mechanisms of the invention include more than two rotational components (e.g., 3, 4, 5, 6, 7, 8, 9, 10 or more rotational components) in which neighboring pairs of rotational components are configured to substantially simultaneously counter-rotate relative to one another. In some embodiments, a friction reducing material is disposed between the first and second rotational components to reduce friction between the first and second rotational components when the first and second rotational components substantially coaxially rotate relative to one another. In some embodiments, the rotational components substantially coaxially rotate around a rotational axis that is substantially horizontally disposed during operation of the rotary mechanism. Optionally, the rotational components each comprise one or more alignment components structured to align neighboring pairs of rotational components relative to one another. In some of these embodiments, for example, the alignment components comprise a circular ridge disposed on, extending from, or attached to a surface of a first member of a pair of neighboring rotational components and a circular groove disposed in a surface of a second member of the pair of neighboring rotational components, which circular ridge inserts into and rotates in the circular groove in an assembled rotary mechanism. In certain embodiments, the alignment components comprise a circular groove disposed in a surface of each member of the pair of neighboring rotational components and a ring disposed in the grooves of the pair of neighboring rotational components, which grooves rotate about the ring in an assembled rotary mechanism.

In some embodiments, the rotary units and rotary mechanisms of the invention include at least one implement rotatably coupled to the rotational component. In certain embodiments, an implement is configured to effect the movement of one or more other components (e.g., propeller components or the like) when the rotational component rotates and the implement operably engages the other components. Typically, an implement extends from one or more surfaces of the at least one of the rotational components. An implement is generally configured to move material when the rotational components substantially coaxially rotate relative to one another and the implement contacts the material. In some embodiments, an implement comprises one or more of, e.g., a blade, a razor, a prong, a peg, a claw, a tine, a chain, a stake, a column, a pillar, an arch, a bracket, a gear component, a bristle, a plume, an abrasive component, an elastomeric component, a nail filing component, a nail buffing component, a hair cutting component, a massaging component, a post, or the like. In certain embodiments of the rotary units and rotary mechanisms of the invention, each of the rotational components comprises multiple implements.

The counter-rotational mechanisms of the rotary units and rotary mechanisms of the invention include various embodiments. In some embodiments, for example, a counter-rotational mechanism comprises a first gear component configured to rotate in a substantially fixed position relative to the first rotational component, a second gear component configured to rotate in a substantially fixed position relative to the second rotational component in which the first and second gear components substantially face one another along an axis of rotation, and a third gear component that engages the first and second gear components such that when the third gear component rotates, the first gear component and the first rotational component rotate in the first direction, and the second gear component and the second rotational component rotate in the second direction. To further illustrate, a counter-rotational mechanism optionally comprises a first gear component configured to rotate in a substantially fixed position relative to the first rotational component, a second gear component configured to rotate in a substantially fixed position relative to the second rotational component, a third gear component that engages the first gear component such that when the third gear component rotates, the first gear component and the first rotational component rotate in a first direction, and a fourth gear component that engages the second gear component such that when the fourth gear component rotates, the second gear component and the second rotational component rotate in a second direction. In another exemplary embodiment, a counter-rotational mechanism comprises a first gear component configured to rotate in a substantially fixed position relative to the first rotational component such that when the first rotational component rotates in a first direction, the first gear component rotates in the first direction, a second gear component that engages the first gear component, which second gear component is configured to rotate in a second direction when first gear component rotates in the first direction, and a third gear component configured to rotate in a substantially fixed position relative to the second rotational component, which third gear component engages the second gear component such that when the second gear component rotates in the second direction, the third gear component and the second rotational component rotate in the second direction. In some of these embodiments, the first rotational component comprises the first gear component and the second rotational component comprises the third gear component.

The drive mechanisms used with the rotary units and rotary mechanisms of the invention include various embodiments. In certain embodiments, for example, a drive mechanism comprises at least one motor. Optionally, a drive mechanism comprises one or more of, e.g., a drive shaft, a chain drive, a belt drive, a gear drive, or the like. In some embodiments, a drive mechanism comprises at least one flexible drive shaft. To further illustrate, a drive mechanism is optionally operably coupled to a counter-rotational mechanism and/or rotational components via at least one drive shaft, at least one drive chain, at least one belt drive, and/or at least one gear drive.

In another aspect, the invention provides a rotary mechanism that includes at least three rotational components that are configured to substantially coaxially rotate relative to one another in which at least one of the rotational components comprises at least one implement. The rotary mechanism also includes means for effecting substantially simultaneous counter-rotation of neighboring pairs of the rotational components relative to one another.

In another aspect, the invention provides a rotary mechanism that includes at least a first rotational component comprising at least a first gear component, which first rotational component comprises or is configured to receive at least a first drive mechanism component in which the first drive mechanism component and/or the first rotational component is configured to receive at least a second drive mechanism component. The rotary mechanism also includes at least a second rotational component comprising at least a second gear component, which second rotational component is configured to receive at least a portion of the first drive mechanism component of the first rotational component, and at least a third gear component that operably engages the first gear component of the first rotational component and the second gear component of the second rotational component such that when the first rotational component rotates in a first direction, the third gear component and the second rotational component rotate in a second direction in which at least one other component (e.g., at least one other rotary mechanism, at least one other rotary unit, or the like) is configured to receive at least a portion of the first drive mechanism component of the first rotational component. Typically, the first and/or second rotational component comprises at least one implement. In some embodiments, the rotary mechanism includes at least one implement rotatably coupled to at least one of the rotational components, which implement is configured to operably engage one or more gear components of one or more other rotational components. In some embodiments, the other component comprises at least one retaining component that is configured to retain the second rotational component rotatably coupled to the first rotational component. The first and second directions are typically substantially opposite from one another. In some embodiments, the first drive mechanism component comprises a shaft component.

In another aspect, the invention provides a rotary mechanism that includes at least first, second, and third rotational components in which at least one of the rotational components comprises at least one implement. The rotary mechanism also includes at least first and second counter-rotational mechanisms in which the first counter-rotational mechanism operably engages at least the first and second rotational components, and in which the second counter-rotational mechanism operably engages at least the second and third rotational components. In addition, the rotary mechanism also includes at least one drive mechanism component or a portion thereof operably engaged with one or more of the rotational components and/or with one or more of the counter-rotational mechanisms, which drive mechanism component or portion thereof is configured at least to effect rotation of the rotational components and the counter-rotational mechanisms such that the first and third rotational components rotate in a first direction and the second rotational component rotates in a second direction. Typically, the drive mechanism component or portion thereof is configured to effect rotation of the rotational components and the counter-rotational mechanisms such that the first and third rotational components rotate in a second direction and the second rotational component rotates in a first direction. In some embodiments, the rotary mechanisms of the invention include more than three rotational components (e.g., 4, 5, 6, 7, 8, 9, 10 or more rotational components). In certain embodiments, the second rotational component is disposed between the first and third rotational components. Optionally, at least one of the rotational components comprises one or more gear components that are configured to operably engage one or more implements rotatably coupled to one or more other rotational components. In certain embodiments, at least the first counter-rotational mechanism comprises at least a first gear component disposed on the first rotational component, at least a second gear component disposed on the second rotational component, and at least a third gear component that operably engages the first and second gear components such that when the first gear component rotates in the first direction, the second and third gear components rotate in the second direction and when the first gear component rotates in the second direction, the second and third gear components rotate in the first direction. In some of these embodiments, the rotary mechanism includes a retaining mechanism that retains the third gear component operably engaged with the first and second gear components. In some of these embodiments, the second gear component substantially defines a gear receiving area that is configured to receive at least a portion of the third gear component. Gear components used with the rotary units, rotary mechanisms, and other applications of the invention typically include gear teeth. Any operable gear tooth configuration and/or type are optionally used in the rotary units, rotary mechanisms and applications of the invention.

The implements of the rotary units and rotary mechanisms of the invention include various embodiments. In some embodiments, for example, an implement is configured to effect the movement of one or more other components (e.g., a propeller component, etc.) when the implement operably engages the other components. In certain embodiments, an implement comprises one or more of, e.g., a blade, a razor, a prong, a peg, a claw, a tine, a chain, a stake, a column, a pillar, an arch, a bracket, a gear component (e.g., a gear tooth, etc.), a bristle, a plume, an abrasive component, an elastomeric component, a nail filing component, a nail buffing component, a hair cutting component, a massaging component, a post, or the like. Typically, at least a portion of an implement comprises at least one cross-sectional shape selected from, e.g., a circle, an oval, a square, a rectangle, a trapezoid, an irregular n-sided polygon, a regular n-sided polygon, and the like. In certain embodiments, an implement is rotatably coupled to the rotational component. In some of these embodiments, the implement is configured to operably engage one or more gear components of one or more other rotational components.

The gear structures of some of the rotary units and rotary mechanisms of the invention include various embodiments. In certain embodiments, for example, a rotary unit or a rotary mechanism includes at least one gear structure that comprises at least one support component in which the third gear component is rotatably coupled to the support component. Typically, a gear structure is at least partially disposed in a gear receiving area or gear structure receiving area. Optionally, a gear structure is rotatably coupled to at least one of first and second rotational components. In some embodiments, at least one of first and second rotational components comprises at least one substantially or partially circular indentation and the gear structure comprises at least one projection configured to at least partially fit and move within the substantially or partially circular indentation to retain the gear structure relative to first and/or second rotational components. In certain embodiments, a gear structure comprises at least one substantially or partially circular indentation and at least one of first and second rotational components comprises at least one projection configured to at least partially fit and move within the substantially or partially circular indentation to retain the gear structure relative to first and/or second rotational components.

In another aspect, the invention provides a rotary mechanism that includes at least two rotational components that are configured to substantially coaxially rotate relative to one another in which at least one of the rotational components comprises at least one implement. The rotary mechanism also includes at least one counter-rotational mechanism operably coupled to at least first and/or second rotational components, which counter-rotational mechanism is configured to effect substantially simultaneous counter-rotation of at least the first and second rotational components relative to one another when movement of at least a portion of the counter-rotational mechanism is effected. In addition, the rotary mechanism also includes at least one drive mechanism operably coupled to the counter-rotational mechanism and/or rotational components, which drive mechanism is configured to effect movement of at least the portion of the counter-rotational mechanism such that the first and second rotational components substantially simultaneously counter-rotate relative to one another. In some embodiments, a support structure structured to support at least a portion of the rotational components, the counter-rotational mechanism, and/or the drive mechanism.

In another aspect, the invention provides a hair cutting device that includes at least one housing comprising one or more surfaces that define a cavity disposed at least partially within the housing and at least one opening that communicates with the cavity, and at least one rotary mechanism at least partially disposed within the cavity, which rotary mechanism comprises: at least two rotational components that are configured to substantially coaxially rotate relative to one another, wherein at least one of the rotational components comprises at least one cutting implement that is configured to cut hair via the opening when the rotational components substantially coaxially rotate relative to one another and the cutting implement contacts the hair; and at least one counter-rotational mechanism operably coupled to at least first and/or second rotational components, which counter-rotational mechanism is configured to effect substantially simultaneous counter-rotation of at least the first and second rotational components relative to one another when movement of at least a portion of the counter-rotational mechanism is effected. In addition, the hair cutting device also includes at least one drive mechanism operably coupled to the counter-rotational mechanism and/or rotational components, which drive mechanism is configured to effect movement of at least the portion of the counter-rotational mechanism such that the first and second rotational components substantially simultaneously counter-rotate relative to one another. In some embodiments, the hair cutting device includes at least one removable structure disposed in or proximal to the opening, which removable structure comprises at least one hole via which the hair is cut when the rotational components substantially coaxially rotate relative to one another and the cutting implement contacts the hair. In some embodiments, the hair cutting device includes a support structure structured to support at least a portion of the rotational components, the counter-rotational mechanism, and/or the drive mechanism. In some embodiments, the hair cutting device is dimensioned to be hand-held. In some embodiments, the housing comprises at least one substantially circular cross-section.

In some embodiments, each of the rotational components comprises multiple cutting implements. In some embodiments, the rotational components are coupled to one another via a shaft positioned proximal to an axis of rotation. In some embodiments, the rotational components are configured to coaxially counter-oscillate relative to one another about an axis of rotation of the rotary mechanism. In some embodiments, the cutting implement comprises a razor.

In another aspect, the invention provides a nail grooming device that includes at least one housing comprising one or more surfaces that define a cavity disposed at least partially within the housing and at least one opening that communicates with the cavity; at least one rotary mechanism at least partially disposed within the cavity, which rotary mechanism comprises: at least two rotational components that are configured to substantially coaxially rotate relative to one another, wherein at least one of the rotational components comprises or is operably coupled to at least one nail grooming implement that is configured to groom at least one nail via the opening when the rotational components substantially coaxially rotate relative to one another and the nail grooming implement contacts the nail; and at least one counter-rotational mechanism operably coupled to at least first and/or second rotational components, which counter-rotational mechanism is configured to effect substantially simultaneous counter-rotation of at least the first and second rotational components relative to one another when movement of at least a portion of the counter-rotational mechanism is effected. In addition, the nail grooming device includes at least one drive mechanism operably coupled to the counter-rotational mechanism and/or rotational components, which drive mechanism is configured to effect movement of at least the portion of the counter-rotational mechanism such that the first and second rotational components substantially simultaneously counter-rotate relative to one another. In some embodiments, the housing comprises at least one substantially circular cross-section. In some embodiments, the nail grooming device includes a friction reducing material disposed between the first and second rotational components to reduce friction between the first and second rotational components when the first and second rotational components substantially coaxially rotate relative to one another.

BRIEF DESCRIPTION OF THE DRAWINGS

The description provided herein is better understood when read in conjunction with the accompanying drawings which are included by way of example and not by way of limitation. It will be understood that like reference numerals identify like components throughout the drawings, unless the context indicates otherwise. It will also be understood that some or all of the figures may be schematic representations for purposes of illustration and do not necessarily depict the actual relative sizes or locations of the elements shown. In addition, in certain figures implements are schematically illustrated as cross-hatches on rotary units.

FIG. 1A schematically illustrates a rotary unit from a front side view according to one embodiment of the invention. FIG. 1B schematically shows the rotary unit of FIG. 1A from a rear side view. FIG. 1C schematically depicts the rotary unit of FIG. 1A from a side view. FIG. 1D schematically shows a gear structure of the rotary unit of FIG. 1A from a rear side view. FIG. 1E schematically illustrates the gear structure of FIG. 1D from a front side view. FIG. 1F schematically shows the gear structure of FIG. 1D from a side view. FIG. 1G schematically illustrates a sectional view of the rotary unit of FIG. 1A. FIG. 1H schematically shows a sectional view of the rotary unit of FIG. 1A. FIG. 1I schematically depicts a partially exploded view of the rotary unit of FIG. 1A.

FIGS. 2 A-F schematically show side elevational views of various exemplary implements.

FIG. 3A schematically illustrates a rotary unit from a side view according to one embodiment of the invention. FIG. 3B schematically shows the rotary unit of FIG. 3A from a front side view. FIG. 3C schematically shows the rotary unit of FIG. 3A from a rear side view. FIG. 3D schematically depicts a sectional view of the rotary unit of FIG. 3A. FIG. 3E schematically depicts a sectional view of the rotary unit of FIG. 3A. FIG. 3F schematically shows a gear structure of the rotary unit of FIG. 3A from a rear side view. FIG. 3G schematically shows a gear structure of the rotary unit of FIG. 3A from a front side view. FIG. 3H schematically shows a gear structure of the rotary unit of FIG. 3A from a side view.

FIG. 4A schematically illustrates a rotary unit from a front side view according to one embodiment of the invention. FIG. 4B schematically shows the rotary unit of FIG. 4A from a rear side view. FIG. 4C schematically shows the rotary unit of FIG. 4A from a side view. FIG. 4D schematically depicts a sectional view of the rotary unit of FIG. 4A. FIG. 4E schematically shows a gear structure of the rotary unit of FIG. 4A from a rear side view. FIG. 4F schematically shows a gear structure of the rotary unit of FIG. 4A from a front side view. FIG. 4G schematically shows a gear structure of the rotary unit of FIG. 4A from a side view.

FIG. 5A schematically illustrates a rotary unit from a front side view according to one embodiment of the invention. FIG. 5B schematically shows the rotary unit of FIG. 5A from a rear side view. FIG. 5C schematically shows the rotary unit of FIG. 5A from a side view. FIG. 5D schematically depicts a sectional view of the rotary unit of FIG. 5A. FIG. 5E schematically shows a gear structure of the rotary unit of FIG. 5A from a front side view. FIG. 5F schematically shows a gear structure of the rotary unit of FIG. 5A from a rear side view. FIG. 5G schematically shows a gear structure of the rotary unit of FIG. 5A from a side view.

FIG. 6A schematically illustrates a rotary unit from a front side view according to one embodiment of the invention. FIG. 6B schematically shows the rotary unit of FIG. 6A from a rear side view. FIG. 6C schematically shows the rotary unit of FIG. 6A from a side view. FIG. 6D schematically depicts a sectional view of the rotary unit of FIG. 6A. FIG. 6E schematically shows a gear structure of the rotary unit of FIG. 6A from a front side view. FIG. 6F schematically shows a gear structure of the rotary unit of FIG. 6A from a rear side view. FIG. 6G schematically shows a gear structure of the rotary unit of FIG. 6A from a side view.

FIG. 7A schematically illustrates a rotary unit from a side view according to one embodiment of the invention. FIG. 7B schematically shows a sectional view of the rotary unit of FIG. 7A. FIG. 8A schematically shows a rotary unit from a front side view according to one embodiment of the invention.

FIG. 8B schematically illustrates the rotary unit of FIG. 8A from a side view. FIG. 8C schematically depicts the rotary unit of FIG. 8A from a rear side view. FIG. 8D schematically shows a sectional view of the rotary unit of FIG. 8A. FIG. 8E schematically illustrates a gear structure of the rotary unit of FIG. 8A from a rear side view. FIG. 8F schematically shows the gear structure of FIG. 8E from a front side view. FIG. 8G schematically illustrates the gear structure of FIG. 8E from a front side view.

FIG. 9A schematically shows a rotary unit from a front side view according to one embodiment of the invention. FIG. 9B schematically shows the rotary unit of FIG. 9A from a rear side view. FIG. 9C schematically depicts the rotary unit of FIG. 9A from a side view.

FIG. 10A schematically shows a rotary unit from a front side view according to one embodiment of the invention. FIG. 10B schematically shows the rotary unit of FIG. 10A from a rear side view. FIG. 10C schematically depicts the rotary unit of FIG. 10A from a side view.

FIG. 11A schematically illustrates a rotary unit from a side view according to one embodiment of the invention. FIG. 11B schematically shows a sectional view of the rotary unit of FIG. 11A. FIG. 11C schematically illustrates a gear structure of the rotary unit of FIG. 11A from a front side view. FIG. 11D schematically illustrates the gear structure of FIG. 11C from a side view. FIG. 11E schematically shows a sectional view of a rotary mechanism that includes the rotary unit of FIG. 11A according to one embodiment of the invention.

FIG. 12A schematically depicts rotary units and a shaft from side elevational views prior to assembly according to one embodiment of the invention. FIG. 12B schematically illustrates the rotary units and the shaft from FIG. 12A from side elevational views in an assembled format.

FIG. 15D schematically shows two of the rotary units from FIG. 15B from side views prior to assembly. FIG. 15E schematically illustrates the rotary units from FIG. 15B from side views with two assembled rotary units prior to assembly with the third rotary unit. FIG. 15F schematically shows the assembled rotary mechanism of FIG. 15C from a side view.

FIG. 16A schematically depicts a partially unassembled rotational or rotary mechanism from a side view according to one embodiment of the invention. FIG. 16B schematically depicts multiple partially assembled rotary mechanisms from side views according to one embodiment of the invention. FIG. 16C schematically shows a rotary mechanism from a side view according to one embodiment of the invention.

FIG. 17A schematically illustrates a rotary mechanism from a partially exploded front side view according to one embodiment of the invention. FIG. 17B schematically shows the rotary mechanism of FIG. 17A from a front side view. FIG. 17C schematically illustrates a rotary mechanism from a front elevational view according to one embodiment of the invention. FIG. 17D schematically illustrates a rotary mechanism from a front elevational view according to one embodiment of the invention. FIG. 17E schematically illustrates a rotary mechanism from a front elevational view according to one embodiment of the invention.

FIG. 21A schematically shows a rotary unit from a front side view according to one embodiment of the invention. FIG. 21B schematically illustrates the rotary unit of FIG. 21A from a rear side view. FIG. 21C schematically shows a rotary unit from a front side view according to one embodiment of the invention. FIG. 21D schematically illustrates the rotary unit of FIG. 21C from a rear side view. FIG. 21E schematically shows a rotary mechanism that includes the rotary units of FIGS. 21 A and C prior to assembly from a side view according to one embodiment of the invention. FIG. 21F schematically depicts an assembled rotary mechanism from FIG. 21E from a side view.

FIG. 27A schematically shows a hair cutting device from a partial cross-sectional view according to one embodiment of the invention. FIG. 27B schematically shows the hair cutting device of FIG. 27A prior to placing a removable structure in an opening of the device housing from side elevational views according to one embodiment of the invention. FIG. 27C schematically shows the hair cutting device from FIG. 27B with the removable structure positioned in the opening of the housing from a side elevational view according to one embodiment of the invention. FIG. 27D schematically illustrates a person shaving facial hair using the hair cutting device from FIG. 27B from a side elevational view according to one embodiment of the invention.

FIG. 28A schematically shows a rotary mechanism of a nail grooming device from a side elevational view according to one embodiment of the invention. FIG. 28B schematically shows the rotary mechanism of FIG. 28A positioned in a housing of a nail grooming device from a partial cross-sectional view according to one embodiment of the invention. FIG. 28C schematically shows the nail grooming device from FIG. 28B from a side elevational view according to one embodiment of the invention. FIG. 28D schematically illustrates the nail grooming device from FIG. 28C being held in one hand of a person and addressing a finger nail on a finger on the other hand of the person from a side elevational view according to one embodiment of the invention.

FIG. 34A schematically illustrates a partially exploded view of a tooth brushing device according to one embodiment of the invention. FIG. 34B schematically shows an assembled tooth brushing device from FIG. 34A from a side view. FIG. 34C schematically depicts the tooth brushing device of FIG. 34B from a top side view. FIG. 34D schematically depicts a rotary mechanism from the tooth brushing device of FIG. 34B from a side view.

FIG. 35A schematically shows a rotary mechanism for a tooth brushing device from a side view according to one embodiment of the invention. FIG. 35B schematically depicts a toothbrush head component that includes the rotary mechanism of FIG. 35A from a side view according to one embodiment of the invention.

FIG. 36 schematically illustrates a cleaning device from a side view according to one embodiment of the invention.

FIG. 39C schematically shows the propulsion device of FIG. 39A from a partially exploded view. FIG. 39D schematically illustrates the propulsion device of FIG. 39A from a side view. FIG. 39E schematically shows the propulsion device of FIG. 39A from a front side view. FIG. 39F schematically shows the propulsion device of FIG. 39A from a rear side view.

FIG. 40A schematically illustrates the propulsion device of FIG. 39A disposed within a housing from a front side view according to one embodiment of the invention. FIG. 40B schematically illustrates the propulsion device of FIG. 39A disposed within a housing from a rear side view according to one embodiment of the invention. FIG. 40C schematically illustrates the propulsion device of FIG. 39A disposed within a housing from a side view according to one embodiment of the invention. FIG. 40D schematically illustrates the propulsion device of FIG. 39A disposed within a housing from a partially sectional front side view according to one embodiment of the invention. FIG. 40E schematically illustrates the propulsion device of FIG. 39A disposed within a housing from a partially sectional side view according to one embodiment of the invention.

FIG. 42A schematically shows an aircraft that includes propulsion devices from a front side view according to one embodiment of the invention. FIG. 42B schematically illustrates the aircraft of FIG. 42A from a side view.

DETAILED DESCRIPTION

I. Introduction

Figure 13A:
FIG. 13A schematically shows a drive mechanism component from a side view according to one embodiment of the invention.
Figure 13B:
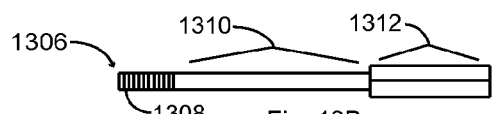
FIG. 13B schematically shows a drive mechanism component from a side view according to one embodiment of the invention.
Figures 13C, 13D:
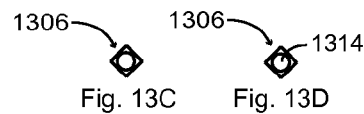
FIG. 13C schematically illustrates the drive mechanism component of FIG. 13B from a front side view.
FIG. 13D schematically illustrates the drive mechanism component of FIG. 13B from a rear side view.
Figure 13E:
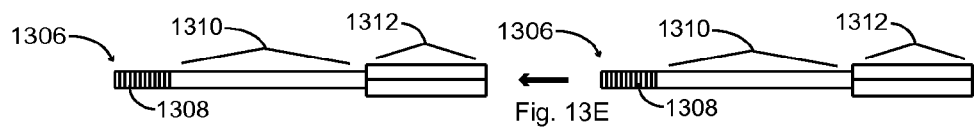
FIG. 13E schematically depicts two drive mechanism components prior to assembly from side views according to one embodiment of the invention.
Figure 13F:
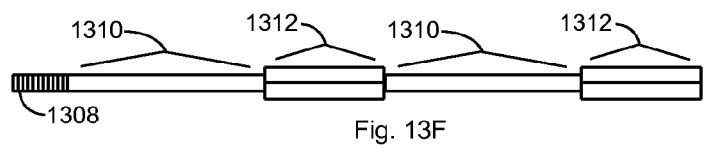
FIG. 13F schematically shows the two drive mechanism components from FIG. 13E in an assembled format from a side view.
Figure 14A:
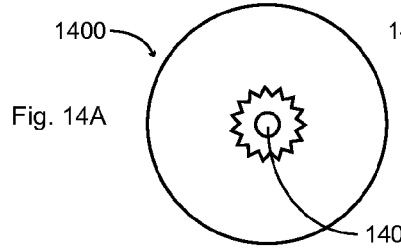
FIG. 14A schematically illustrates a rotary unit from a front side view according to one embodiment of the invention.
Figure 14B:
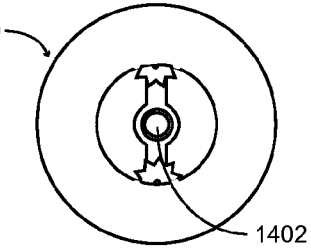
FIG. 14B schematically shows the rotary unit from FIG. 14A from a rear side view.
Figure 14C:
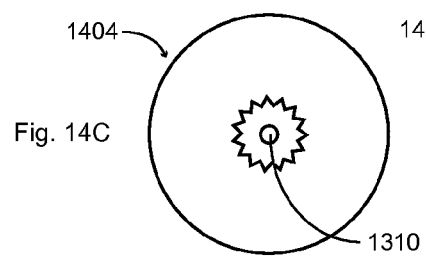
FIG. 14C schematically illustrates a rotary unit from a front side view according to one embodiment of the invention.
Figure 14D:
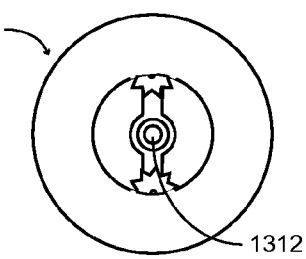
FIG. 14D schematically shows the rotary unit from FIG. 14C from a rear side view.
Figure 14E:
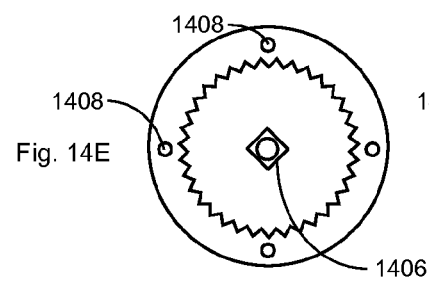
FIG. 14E schematically shows a rotational component of the rotary unit from FIG. 14C from a rear side view without positioned retaining and drive mechanism components.
Figure 14F:
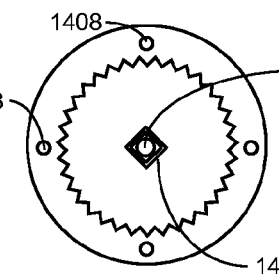
FIG. 14F schematically illustrates the rotational component of the rotary unit from FIG. 14E with a drive mechanism component positioned in a drive mechanism component receiving area of the rotational component.

Before describing the invention in detail, it is to be understood that this invention is not limited to particular methods, rotary units, rotary mechanisms, devices, or systems, which can vary. As used in this specification and the appended claims, the singular forms "a," "an," and "the" also include plural referents unless the context clearly provides otherwise. It is also to be understood that the terminology used herein is for the purpose of describing particular embodiments only, and is not intended to be limiting. Further, unless defined otherwise, all technical and scientific terms used herein have the same meaning as commonly understood by one of ordinary skill in the art to which this invention pertains. In describing and claiming the invention, the following terminology, and grammatical variants thereof, will be used in accordance with the definitions set forth below.

The term "coaxially positioned" refers to objects that are positioned relative to one another such that they can rotate about a substantially coincident axis.

The term "fixed position" refers to objects that are positioned relative to one another such that they do not move separately from one another. In some embodiments, for example, gear components (e.g., sun gear components) are attached (e.g., integrally fabricated, bonded, welded, adhered, or the like) to rotational components, such that when the rotational components move in one direction, the gear components move in the same direction as the rotational components.

The term "counter-rotate" or "contra-rotate" refers to objects that rotate in opposite directions relative to one another. In some embodiments, for example, rotary mechanisms include rotational components that are configured to rotate in opposite directions.

The term "communicate" refers to the direct or indirect transfer or transmission, and/or capability of directly or indirectly transferring or transmitting, something at least from one thing to another thing. In some embodiments, for example, devices include housings having openings through which hair, finger nails, or the like can be transferred to contact implements within housing cavities of the devices.

The invention relates to rotary units and rotary mechanisms that are suitable for use in numerous applications. Rotary units typically include rotational components that are configured to rotate. In some embodiments, for example, multiple rotary units are assembled in rotary mechanisms such that neighboring pairs of rotational components counter-rotate or contra-rotate relative to one another during operation of the rotary mechanisms. Rotational components generally include one or more implements that are structured to perform or effect one or more types of work as the rotational components rotate relative to one another in a given rotary mechanism. In certain embodiments, implements are configured to rotate and/or to effect the movement of other components as rotational components rotate. The representative embodiments described herein are intended to illustrate, but not to limit, the invention. Essentially any combination of components or portions thereof described herein are optionally utilized or adapted for use together in certain embodiments.

II. Exemplary Rotary Units

FIGS. 1A-H schematically show a rotary unit or components thereof according to one embodiment of the invention. As shown, rotary unit 100 includes rotational component 102, which includes first gear component 104 disposed on a first side of rotational component 102 (e.g., in an inner region of the first side) and second gear component 106 disposed on a second side of rotational component 102 (e.g., in an outer region of the second side). As shown, the first and second sides substantially oppose one another. Gear components used with the rotary units, rotary mechanisms, and other applications of the invention typically include gear teeth. Any operable gear tooth configuration and/or type are optionally used in the rotary units, rotary mechanisms and applications of the invention. Second gear component 106 substantially defines gear structure receiving area 108, which is configured to receive gear structure 110. Gear structure 110 includes support component 112 and third gear components 114. Third gear components 114 are configured to operably engage second gear component 106 such that when third gear components 114 rotate in a first direction, second gear component 106 and rotational component 102 also rotate the first direction. Third gear components 114 are configured to operably engage other gear components, such as a first gear component of another rotary unit such that when the other gear components rotate in a second direction, third gear components 114, second gear component 106, and rotational component 102 all rotate in the first direction. Rotary unit 100 also includes retaining mechanism 116 (shown as a wall or lip in this exemplary embodiment) that is structured to retain gear structure 110 at least partially in gear structure receiving area 108. As further shown in FIG. 1I, for example, in some embodiments during rotary unit assembly retaining mechanism 116 is attached to rotational component 102, once gear structure 110 is positioned in gear structure receiving area 108, via attachment components 118 (e.g., which clip into corresponding notches (not within view) in rotational component 102 in this representative embodiment).

Rotary unit 100 also includes implements 120 shown as beads that can be used, for example, as part of a massaging device or the like. Essentially any implement (e.g., type(s) and/or number on a given rotational component, etc.) is optionally adapted for use with the rotary units of the present invention, e.g., depending on the intended application of a given rotary unit. Representative implements that are optionally used include one or more of, e.g., a blade, a razor, a prong, a peg, a claw, a tine, a chain, a stake, a column, a pillar, an arch, a bracket, a gear component, a bristle, a plume, an abrasive component, an elastomeric component, a nail filing component, a nail buffing component, a hair cutting component, a massaging component, a post, or the like. Some exemplary implements 200-210 are also illustrated from side elevational views in, e.g., FIGS. 2 A-F.

In addition, rotary unit 100 also includes drive mechanism component receiving area 122 (shown as a hole disposed through rotational component 102) that is configured to receive a drive mechanism component, such as a drive shaft or a portion thereof. Other exemplary drive mechanism components are described herein or otherwise known in the art.

FIGS. 3 A-H schematically show another exemplary embodiment of a rotary unit or components thereof of the invention. As shown, rotary unit 300 includes rotational component 302 that includes first gear component 304 disposed on a first surface of rotational component 302 and second gear component 306 disposed on a second surface of rotational component 302. Rotary unit 300 also include gear structure 308, which is structured to fit within gear structure receiving area 310 and operably engage second gear component 306 of rotational component 302. Gear structure 308 includes third gear components 312 rotatably coupled to support component 314. As shown, gear structure 308 includes hole 315 that is structured to align with drive mechanism component receiving area 316 of rotational component 302. When a drive mechanism component, such as a drive shaft is disposed through hole 315 and drive mechanism component receiving area 316, gear structure 308 and rotational component 302 can rotate about the drive mechanism component. Support component 314 of gear structure 308 also includes tips 318 that position a portion of support component 314 away from rotational component 302, e.g., to minimize friction between rotational component 302 and gear structure 308 when those components rotate relative to one another. In addition, rotary unit 300 also includes retaining mechanism 319 (shown as a wall or lip) that is structured to retain gear structure 308 positioned relative to rotational component 302.

Rotary unit 300 also includes implements 320 that are rotatably coupled to rotational component 302. As shown, rotatably coupled implements 320 include gear components 322 that are configured to operably engage a corresponding gear component on a neighboring rotary unit when the neighboring rotary unit is disposed suitably proximal to rotary unit 300. In these embodiments, during operation, as neighboring rotary units counter-rotate relative to one another, rotatably coupled implements, such as implements 320 (e.g., implements suitable for a massaging device or the like) also rotate. To further illustrate, rotary unit 300 includes gear component 324 that is configured to operably engage rotatably coupled implements disposed on a neighboring rotary unit.

FIGS. 4 A-G schematically illustrate a rotary unit or components thereof according to one embodiment of the invention. As shown, rotary unit 400 includes rotational component 402, which includes first gear component 404 extending from a first side, and second gear component 406 on a second side and substantially defining gear structure receiving area 408. Rotary unit 400 also includes gear structure 410, which includes third gear components 412 rotatably coupled to support component 414. As also shown, gear structure 410 includes hole 416 that is structured to align with drive mechanism component receiving area 418 of rotational component 402, e.g., to receive a drive mechanism component, such as a drive shaft about which gear structure 410 and rotational component 402 rotate.

Rotary unit 400 also includes a retaining mechanism that is configured to retain gear structure 410 in position relative to rotational component 402 such that the components can operably engage one another during operation. The retaining mechanism of rotary unit 400 includes groove or track 420 disposed approximately around gear structure receiving area 408 in rotational component 402. In addition, the retaining mechanism also includes projections 422 of gear structure 410 that insert into groove or track 420 such that gear structure 410 is retained and rotates within gear structure receiving area 408.

In some embodiments, the rotational components of the rotary units of the invention include implements that are configured to effect the movement of one or more other components (e.g., propeller components or the like) when the rotational components rotate and the implements operably engage the other components. To illustrate, rotational component 402 of rotary unit 400 also includes gear component 424 that is configured to operably engage other gear components of other components, e.g., to effect rotation of those components when rotational component 402 rotates.

FIGS. 5 A-G schematically show another exemplary embodiment of a rotary unit of the invention. As shown, rotary unit 500 includes rotational component 502 that includes first and second surfaces that substantially oppose one another. First gear component 504 is disposed on the first surface of rotational component 502 and is configured to operably engage third gear components of another rotary unit. Second gear component 506 is disposed on the second surface of rotational component 502 and substantially defines gear structure receiving area or cavity 508.

Rotary unit 500 also include gear structure 510, which includes support structure 512 and third gear components 514 rotatably coupled to support structure 512. Rotary unit 500 also includes a retaining mechanism formed, in part, by groove or track 516 formed in rotational component 502. Circular projection 518 disposed on support structure 512 of gear structure 510 is configured to fit within groove or track 516 such that gear structure 510 is retained, yet permitted to rotate, within gear structure receiving area 508. As also shown, rotary unit 500 also includes implements 520 (shown as blades) extending from a surface of rotational component 502.

FIGS. 6 A-G schematically show another exemplary embodiment of a rotary unit of the invention. As shown, rotary unit 600 includes rotational component 602 that includes first and second surfaces that substantially oppose one another. First gear component 604 is disposed on a first side of rotational component 602 and is configured to operably engage third gear components 614 of gear structure 610. Second gear component 606 is disposed on the second surface of rotational component 602 and substantially defines gear structure receiving area or cavity 608.

Rotary unit 600 also include gear structure 610, which includes support structure 612 and third gear components 614 rotatably coupled to support structure 612. Rotary unit 600 also includes a retaining mechanism formed, in part, by groove or track 616 formed in rotational component 602. Circular projection 618 disposed on support structure 612 of gear structure 610 is configured to fit within groove or track 616 such that gear structure 610 is retained, yet permitted to rotate, about first gear component 604. As also shown, rotary unit 600 also includes implements 620 (shown as blades) extending from a surface of rotational component 602.

FIGS. 7 A and B schematically illustrate a rotary unit according to another exemplary embodiment of the invention. As shown, rotary unit 700 includes rotational component 702. First gear component 704 extends from a first side of rotational component 702, while gear structure 706 engages a second gear component in a gear structure receiving area on a second side of rotational component 702 and partially extends from the gear structure receiving area. Gear structure includes third gear components 708 rotatably coupled to support structure 710. Rotary unit 700 also includes a retaining mechanism formed, in part, by groove or track 712 formed in the gear structure receiving area of rotational component 702. Circular projection 714 disposed on support structure 710 of gear structure 706 is configured to fit within groove or track 712 such that gear structure 706 is retained, yet permitted to rotate, within the gear structure receiving area of rotational component 702. First gear component 704 is configured to engage one or more third gear components of another rotary unit. Third gear components 708 are configured to engage the second gear component in the gear structure receiving area and a first gear component of another rotary unit.

FIGS. 8 A-G schematically show a rotary unit or components thereof according to another representative embodiment of the invention. As shown, rotary unit 800 includes rotational component 802. Rotational component 802 includes first gear component 804 on a first side and second gear component 806 on a second side. Second gear component 806 substantially defines a gear structure receiving area of rotational component 802. Rotary unit 800 also includes gear structure 808 disposed within the gear structure receiving area. Gear structure 808 includes third gear components 810 rotatably coupled to support component 812. Third gear components 810 are configured to operably engage second gear component 806 of rotational component 802 and the first gear component of another rotary unit or another gear component, such as a component of a drive mechanism or the like. Gear structure 808 also includes hole or aperture 814, which is structured to align with drive mechanism component receiving area 816 of rotational component 802, e.g., to receive a drive mechanism component, such as a drive shaft about which gear structure 808 and rotational component 802 rotate. Rotary unit 800 also includes a retaining mechanism that is configured to retain and permit gear structure 808 to rotate within the gear structure receiving area of rotational component 802. In particular, support component 812 of gear structure 808 includes partially circular indentation 818 and rotational component 802 comprises projection 820 (e.g., an elevated circular track or the like). Projection 820 is configured to at least partially fit and move within partially circular indentation 818 to retain gear structure 808 at least partially within the gear structure receiving area when second gear component 806 and third gear components 810 operably engage one another. In some embodiments, gear structures comprise projections, such as projection 820 and rotational components comprise the substantially or partially circular indentation (e.g., a circular track or groove structured to receive the projection).

Rotary unit 800 also includes implements 822 that are rotatably coupled to rotational component 802. As shown, rotatably coupled implements 822 include gear components 824 that are configured to operably engage a corresponding gear component on a neighboring rotary unit when the neighboring rotary unit is disposed suitably proximal to rotary unit 800. In these embodiments, during operation, as neighboring rotary units counter-rotate relative to one another, rotatably coupled implements, such as implements 822 (e.g., shown as bristles suitable for a toothbrush, household cleaning device, or the like) also rotate. To further illustrate, rotary unit 800 includes gear component 826 that is configured to operably engage rotatably coupled implements disposed on a neighboring rotary unit.

FIGS. 9 A-C schematically show a rotary unit according to one embodiment of the invention. As shown, rotary unit 900 includes rotational component 902, which includes first gear component 904 on a first side. Rotary unit 900 also includes a gear structure 906 disposed and able to rotate within a gear structure receiving area rotational component 902. Lip or wall 908 retains gear structure 906 in the gear structure receiving area, similar to how lip or wall 319 retains gear structure 308 in gear structure receiving area 310 of rotary unit 300, as described above. Rotary unit 900 also includes alignment components that are structured to align rotary units relative to one another, e.g., in a given device or other application. In particular, the first side of rotational component 902 includes circular groove 910, while the second side of rotational component 902 includes circular ridge 912. Circular groove 910 is configured to receive a circular ridge (e.g., circular ridge 1012) of another rotary unit (e.g., rotary unit 1000), which circular ridge is configured to rotate within circular groove 910. In contrast, circular ridge 912 is configured to fit and rotate within a circular groove (e.g., circular groove 1010) of another rotary unit (e.g., rotary unit 1000). In some embodiments, the first side of rotational component 902 includes circular ridge 912, while the second side of rotational component 902 includes circular groove 910.

Rotary unit 900 also include drive mechanism component receiving area 914 that is configured to receive a drive mechanism component (e.g., drive mechanism component 1016 (shown as a drive shaft) of rotary unit 1000). Rotational component 902 is configured to rotate about a drive mechanism component (e.g., drive mechanism component 1016 of rotary unit 1000), while first gear component 904 operably engages a gear component (e.g., a gear component of a gear structure) of another rotary unit (e.g., a rotary unit, such as a rotary unit 1000) and gear components of gear structure 906 operably engage another gear component (e.g., a first gear component) of yet another rotary unit (e.g., another rotary unit, such as another rotary unit 1000). As also shown, a surface of rotational component 902 also includes multiple implements 916 (shown as razors or cutting edges) that are optionally used in hair cutting devices or other applications.

FIGS. 10 A-C schematically show a rotary unit according to one embodiment of the invention. As shown, rotary unit 1000 includes rotational component 1002, which includes first gear component 1004 on a first side. Rotary unit 1000 also includes a gear structure 1006 disposed and able to rotate within a gear structure receiving area rotational component 1002. Lip or wall 1008 retains gear structure 1006 in the gear structure receiving area, similar to how lip or wall 319 retains gear structure 308 in gear structure receiving area 310 of rotary unit 300, as described above. Rotary unit 1000 also includes alignment components that are structured to align rotary units relative to one another, e.g., in a given device or other application. In particular, the first side of rotational component 1002 includes circular groove 1010, while the second side of rotational component 1002 includes circular ridge 1012. Circular groove 1010 is configured to receive a circular ridge (e.g., circular ridge 912) of another rotary unit (e.g., rotary unit 900), which circular ridge is configured to rotate within circular groove 1010. In contrast, circular ridge 1012 is configured to fit and rotate within a circular groove (e.g., circular groove 910) of another rotary unit (e.g., rotary unit 900). In some embodiments, the first side of rotational component 1002 includes circular ridge 1012, while the second side of rotational component 1002 includes circular groove 1010.

Rotary unit 1000 also include drive mechanism component receiving area 1014 that is configured to receive a drive mechanism component (e.g., drive mechanism component 1016 of a rotary unit 1000). In the embodiment shown, drive mechanism component receiving area 1014 includes a female threaded region that is configured to receive a male threaded region of drive mechanism component 1016 of another rotary unit 1000. As described above, another rotary unit (such as a rotary unit 900) is configured to fit between two rotary units 1000 and rotate around a drive mechanism component 1016 of one of the rotary units 1000. As also shown, a surface of rotational component 1002 also includes multiple implements 1018 (shown as razors or cutting edges) that are optionally used in hair cutting devices or other applications.

FIGS. 11A-D schematically show a rotary unit or components thereof according to one embodiment of the invention. As shown, rotary unit 1100 includes rotational component 1102 that includes first gear component 1104 and a gear structure receiving area. As also shown, rotary unit 1100 also includes gear structure 1106, which includes third gear components 1108. Third gear components 1108 are rotatably coupled to first support component 1110 and second support component 1112. Rotary unit 1100 also includes a retaining mechanism formed, in part, by first groove or track 1114 formed in a second side of rotational component 1102 proximal to the gear structure receiving area. First circular projection 1116 disposed on first support component 1110 of gear structure 1106 is configured to fit within first groove or track 1114 such that gear structure 1106 is retained, yet permitted to rotate, within the gear structure receiving area of rotary unit 1100 and operably engage a second gear component of rotary unit 1100 and a gear component of another rotary unit (e.g., a first gear component of another rotary unit 1100). Rotary unit 1100 also includes second groove or track 1118 formed in a first side of rotational component 1102. Second groove or track 1118 is configured to receive and rotatably retain a second circular projection 1120 of a gear structure 1106 of another rotary unit, such as another rotary unit 1100. Similarly, second circular projection 1120 of gear structure 1106 is configured to retainingly fit and rotate within a second groove or track 1118 of yet another rotary unit such that third gear components 1108 engage the second gear components of rotary unit 1100 and, e.g., the first gear component of the other rotary unit. In some of these embodiments, drive mechanism components, such as shafts or the like are not used, for example, because multiple rotary units are coupled to, and able to rotate relative to, one another via these retaining mechanisms.

To further illustrate, FIG. 11E schematically illustrates a sectional view of a rotary mechanism 1121 that includes four rotary units 1100 in which neighboring pairs of rotary units 1100 are configured to counter-rotate relative to one another (represented by the directional arrows shown below each rotary unit 1100 in rotary mechanism 1121). Additional representative rotary mechanisms are described further herein.

III. Exemplary Rotary Mechanisms

In certain embodiments, the invention provides rotary mechanisms that include two or more rotational components or rotary units (e.g., 2, 3, 4, 5, 6, 7, 8, 9, 10, 11, 12, 13, 14, 15, or more rotational components or rotary units). Rotary mechanisms also typically include at least one counter-rotational mechanism operably coupled to one or more of the rotational components. The counter-rotational mechanism is generally configured to effect substantially simultaneous counter-rotation of the rotational components relative to one another when movement of at least a portion of the counter-rotational mechanism is effected. Rotary mechanisms also typically include drive mechanisms operably coupled to the counter-rotational mechanism and/or rotational components. Drive mechanisms are typically configured to effect movement of at least the portion of the counter-rotational mechanisms such that the rotational components substantially simultaneously counter-rotate relative to one another. In some embodiments, for example, multiple rotary units are included as components (e.g., rotational components and counter-rotational mechanisms, etc.) of rotary mechanisms.

In some embodiments, rotary units are operably coupled to one another via one or more shafts. To illustrate one embodiment, FIG. 12A schematically depicts rotary units 100 and drive mechanism component 1202 (shown as a shaft) prior to assembly. As shown, gear component 1204 is fixedly coupled to shaft 1202 and is configured to operably engage third gear components 114 (not within view in FIGS. 12 A and B) of a rotary unit 100 in assembled rotary mechanism 1200. During assembly, shaft 1202 is inserted through drive mechanism component receiving areas 122 (shown as holes, e.g., in FIG. 1A) of rotary units 100 to operably couple rotary units 100 to one another. FIG. 12B schematically illustrates rotary units 100 and shaft 1202 following assembly. Suitable shafts include a variety of cross-sectional shapes (e.g., circular, oval, triangular, square, rectangular, polygonal, etc.). In some embodiments, a given shaft includes multiple cross-sectional shapes. In some of these embodiments, individual rotary units include drive mechanism component receiving areas (e.g., holes, apertures, etc.) that correspond to those different cross-sectional shapes. In some embodiments, for example, one member of a pair of neighboring rotary units includes a square hole that fits on a square cross-section of a shaft, while the other member of the pair includes a circular hole that fits on a circular cross-section of the shaft. In these embodiments, the rotary unit with the square hole typically rotates in a substantially fixed position relative to the shaft, whereas the rotary unit with the circular hole typically rotates substantially free or independent relative to the shaft. To illustrate, FIG. 13A schematically depicts drive mechanism component 1300 (shown as a shaft), which includes circular cross-sectional areas 1302 and square cross-sectional areas 1304. To further illustrate, FIGS. 13 B-F schematically show drive mechanism component units 1306, which each include circular cross-sectional areas 1310 and square cross-sectional areas 1312. As also shown, drive mechanism component units 1306 include threaded segments 1308. During assembly, a threaded segment 1308 on a given drive mechanism component unit 1306 is threaded into a corresponding threaded receiving hole 1314 in neighboring shaft units 1306.

FIGS. 14 A-F schematically show rotary units or components thereof that are optionally used with drive mechanism components 1306. More specifically, drive mechanism component receiving area 1402 of rotary unit 1400 is configured to receive and rotate around circular cross-sectional areas 1310 of drive mechanism components 1306. In contrast, drive mechanism component receiving area 1406 of rotary unit 1404 is configured to receive square cross-sectional area 1312, such that rotary unit 1404 is substantially fixed relative to, and rotates with, drive mechanism component 1306. To further illustrate, FIG. 14E schematically shows a rotational component of rotary unit 1404 from a rear side view in which drive mechanism component 1306 is absent from drive mechanism component receiving area 1406, whereas FIG. 14F schematically illustrates the rotational component of rotary unit 1404 drive mechanism component 1306 positioned in drive mechanism component receiving area 1406 of the rotational component. As also shown in, e.g., FIGS. 14 E and F, the rotational components of rotary unit 1404 also include holes 1408, which are structured to receive a retaining mechanism component (not shown in FIGS. 14 E and F) that retains a gear structure in a gear structure receiving area of rotary unit 1404. Rotary units 1400 and 1404 include gear structures and gear structure receiving areas that are similar to gear structure 308 and gear structure receiving area 310 of rotary unit 300, as described above.

Figure 15A:
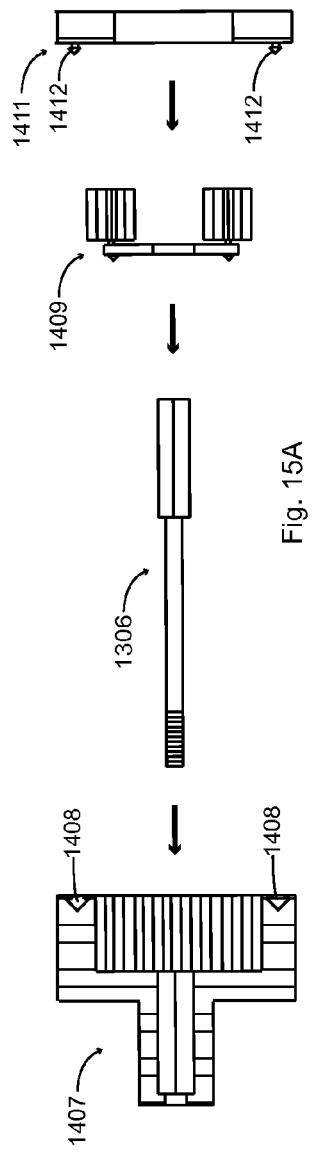
FIG. 15A schematically illustrates the rotary unit from FIG. 14C from an exploded sectional view.
Figure 15B:
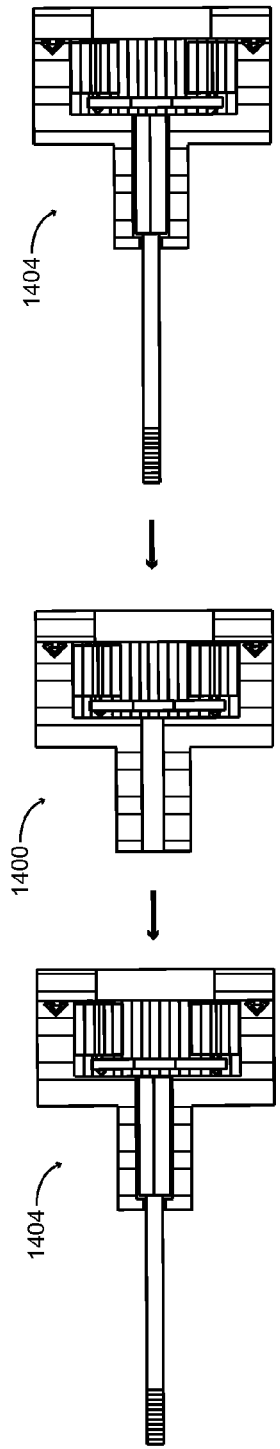
FIG. 15B schematically shows three rotary units of a rotary mechanism prior to assembly from sectional views according to one embodiment of the invention.
Figure 15C:
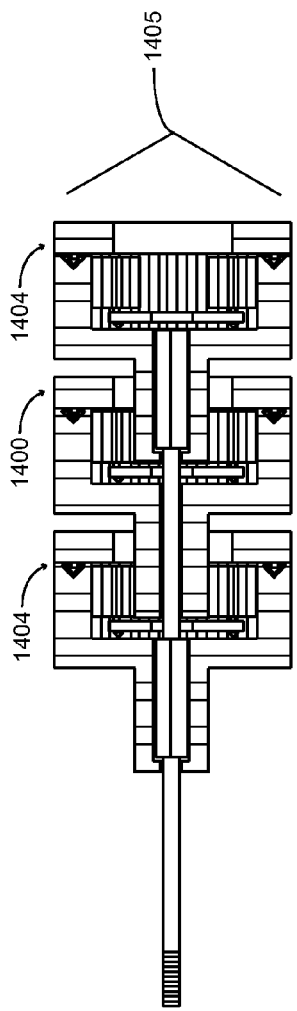
FIG. 15C schematically depicts the three rotary units from FIG. 15B in an assembled rotary mechanism from a sectional view.

FIGS. 15 A-F schematically further show rotary units 1400 and 1404 and rotary mechanism 1405, which includes rotary units 1400 and 1404. In particular, FIG. 15A schematically illustrates rotary unit 1404 from an exploded sectional view prior to assembly. As shown, rotary unit 1404 includes rotational component 1407, drive mechanism component 1306, gear component 1409, and retaining mechanism component 1411. Retaining mechanism component 1411 includes attachment components 1412, which fit within holes 1408 of rotational component 1407 to retain gear structure in the gear structure receiving area of assembled rotary unit 1404. FIG. 15B schematically shows three rotary units of rotary mechanism 1405 prior to assembly from sectional views. FIG. 15C schematically depicts assembled rotary mechanism 1405 from a sectional view. FIG. 15D schematically shows rotary units 1400 and 1404 from side views prior to assembly. FIG. 15E schematically illustrates side views with two assembled rotary units 1400 and 1404 prior to assembly with another rotary unit 1404. FIG. 15F schematically shows assembled rotary mechanism 1405 from a side view.

Now referring FIGS. 16 A-C, which schematically depict various aspects of rotational or rotary mechanisms from side elevational views according to certain embodiments of the invention. In FIG. 16A, for example, rotary mechanism 1600 includes rotary unit 1602 and rotary unit 1608. Implements are schematically illustrated as an abrasive material on the rotary units that can be used in, for example, dermabrasion, woodworking, metal grinding or machining, or many other applications. Rotary unit 1608 is fixedly coupled to shaft 1606, which includes threaded segment 1604. Shaft 1606 includes a circular cross-section that inserts through a corresponding circular hole (not within view) disposed through rotary unit 1602. Rotary unit 1602 freely rotates around shaft 1606. As shown in FIG. 16B, once rotary unit 1602 is positioned on shaft 1606 next to rotary unit 1608 (e.g., such that a gear structure of rotary unit 1602 operably engages first gear component 1603 of rotary unit 1608), one rotary mechanism 1600 can be operably connected to another rotary mechanism 1600 via threaded segment 1604. In FIG. 16C, for example, two rotary mechanisms 1600 are operably connected to one another and can be coupled with, e.g., another component of a drive mechanism, such as a motor (e.g., a gas powered motor, an electric motor, etc.) via threaded segment 1604. The motor is typically used to effect counter-rotation of rotary units 1602 and 1608, as schematically represented by the direction arrows in FIG. 16C.

FIGS. 17 A-E schematically illustrate various exemplary rotary mechanisms from front elevational views. As shown in FIGS. 17 A and B, for example, rotary mechanism 1700 includes two rotational components 1702 and 1704 rotatably coupled to one another via shaft 1706. Rotational components 1702 and 1704 are configured to counter-rotate relative to one another. Rotational component 1702 includes gear component 1708, while rotational component 1704 includes gear component 1710. The drive mechanism of rotary mechanism 1700 includes gear component 1712, which engages gear component 1708. Support structure 1714 (shown as a support bracket) maintains the positions of gear component 1712 and gear component 1708 relative to one another. Rotation of gear component 1712 is effected by shaft 1716, which connects to, e.g., a motor (not shown). The drive mechanism of rotary mechanism 1700 also includes gear component 1718, which engages gear component 1710. Support structure 1720 (shown as a support bracket) maintains the positions of gear component 1718 and gear component 1710 relative to one another. Rotation of gear component 1718 is effected by shaft 1722, which connects to, e.g., a motor (not shown).

FIG. 17C schematically depicts exemplary rotary mechanism 1746, which includes rotational components 1748 and 1750 that are rotatably coupled to one another via support structure 1752 (shown as a support bracket), which maintains the positions of gear component 1754 and gear component 1756 relative to one another and relative to gear component 1758. Rotational components 1748 and 1750 are configured to counter-rotate relative to one another. As shown, rotational component 1748 includes gear component 1754, while rotational component 1750 includes gear component 1756. The drive mechanism of rotary mechanism 1746 includes gear component 1758, which engages gear components 1748 and 1756. Rotation of gear component 1758 is effected by shaft 1760, which connects to, e.g., a motor (not shown).

FIG. 17D schematically depicts exemplary rotary mechanism 1724, which includes three pairs of rotational components 1726 that are rotatably coupled to one another via a shaft. Members of a give pair of rotational components 1726 are configured to counter-rotate relative to one another. In some embodiments, rotational component or portions thereof are coated with materials (e.g., polytetrafluoroethylene, etc.) that reduce friction between neighboring rotational components when those components counter-rotate relative to one another. Rotational component 1727 includes gear component 1728, while rotational component 1730 includes gear component 1732. The drive mechanism of rotary mechanism 1724 includes gear component 1734, which engages gear component 1728. Support structure 1736 (shown as a support bracket) maintains the positions of gear component 1734 and gear component 1728 relative to one another. Rotation of gear component 1734 is effected by shaft 1738, which connects to, e.g., a motor (not shown). The drive mechanism of rotary mechanism 1724 also includes gear component 1740, which engages gear component 1732. Support structure 1742 (shown as a support bracket) maintains the positions of gear component 1732 and gear component 1740 relative to one another. Rotation of gear component 1740 is effected by shaft 1744, which connects to, e.g., a motor (not shown).

FIG. 17E schematically depicts exemplary rotary mechanism 1762, which includes multiple rotational components 1764 that are rotatably coupled to one another via a shaft and support structure 1766 (shown as a support bracket), which maintains the positions of gear component 1768 and gear component 1770 relative to one another and relative to gear component 1772. Rotational components 1764 are configured to counter-rotate relative to one another. The drive mechanism of rotary mechanism 1762 includes gear component 1772, which engages gear components 1768 and 1770. Rotation of gear component 1772 is effected by shaft 1774, which connects to, e.g., a motor (not shown).

Figure 18A:
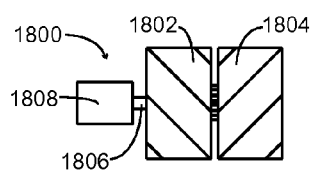
FIG. 18A schematically illustrates a rotary mechanism from a front elevational view according to one embodiment of the invention.

FIGS. 18 A-C schematically illustrate various exemplary rotary mechanisms from front elevational views. As shown in FIG. 18A, for example, rotary mechanism 1800 includes rotational components 1802 and 1804 rotatably coupled to one another via shaft 1806. Rotational components 1802 and 1804 are configured to counter-rotate relative to one another. Rotational components 1802 and 1804 are also coupled to motor 1808 via shaft 1806. Motor 1808 is configured to effect counter-rotation of rotational components 1802 and 1804.

Figure 18B:
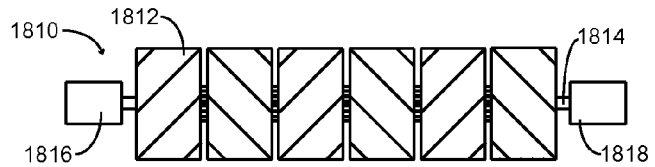
FIG. 18B schematically illustrates a rotary mechanism from a front elevational view according to one embodiment of the invention.

FIG. 18B schematically depicts exemplary rotary mechanism 1810, which includes rotational components 1812 that are rotatably coupled to one another via shaft 1814. Rotational components 1812 are configured to counter-rotate relative to one another. The drive mechanism of rotary mechanism 1810 includes motors 1816 and 1818 that are coupled to rotational components 1812 via shaft 1814. Motors 1816 and 1818 are configured to effect counter-rotation of rotational components 1812.

Figure 18C:
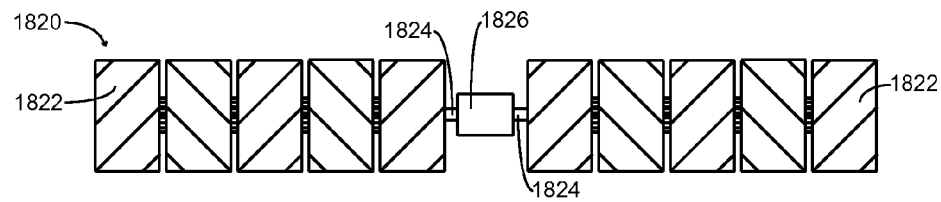
FIG. 18C schematically illustrates a rotary mechanism from a front elevational view according to one embodiment of the invention.

FIG. 18C schematically depicts exemplary rotary mechanism 1820, which includes rotational components 1822 that are rotatably coupled to one another via shaft 1824. Rotational components 1822 are configured to counter-rotate relative to one another. The drive mechanism of rotary mechanism 1820 includes motor 1826 that is coupled to rotational components 1822 via shaft 1824. Motor 1826 (e.g., a dual shaft motor, etc.) is configured to effect counter-rotation of rotational components 1822.

Figure 19A:
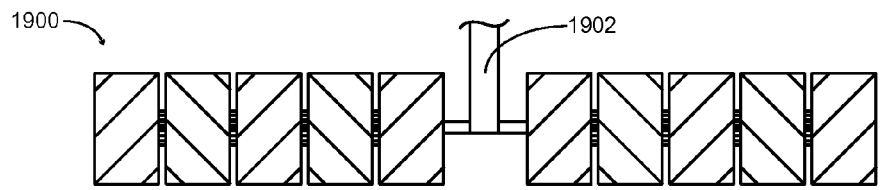
FIG. 19A schematically illustrates a rotary mechanism from a front elevational view according to one embodiment of the invention.
Figure 19B:
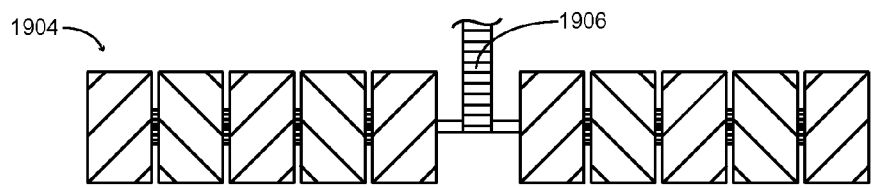
FIG. 19B schematically illustrates a rotary mechanism from a front elevational view according to one embodiment of the invention.
Figure 20A:
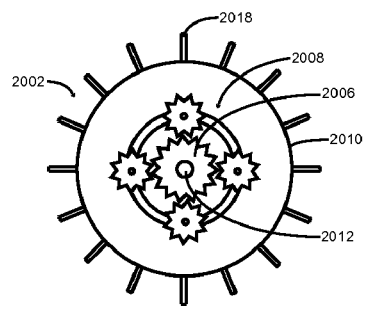
FIG. 20A schematically shows a rotary unit from a front side view according to one embodiment of the invention.
Figure 20B:
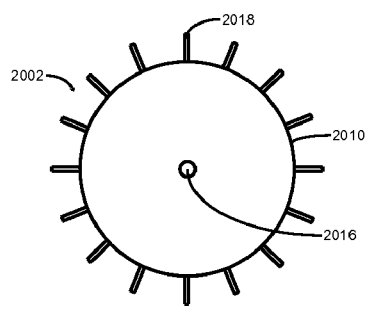
FIG. 20B schematically illustrates the rotary unit of FIG. 20A from a rear side view.
Figure 20C:
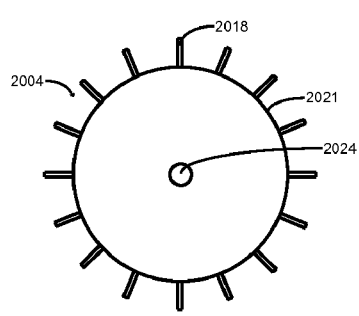
FIG. 20C schematically shows a rotary unit from a front side view according to one embodiment of the invention.
Figure 20D:
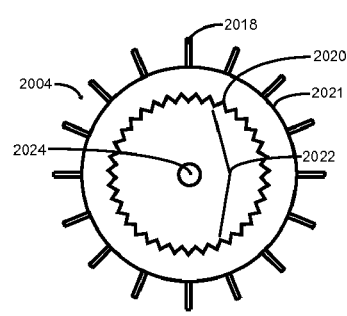
FIG. 20D schematically illustrates the rotary unit of FIG. 20C from a rear side view.
Figure 20E:
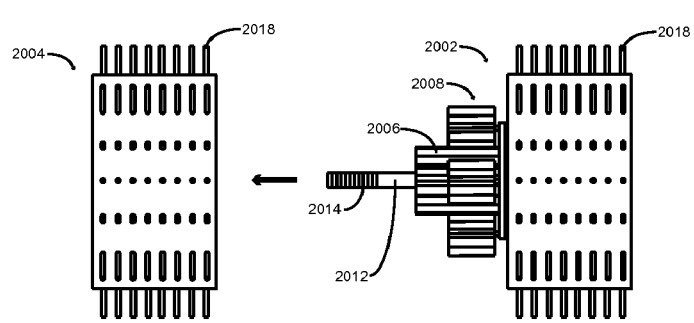
FIG. 20E schematically shows a rotary mechanism that includes the rotary units of FIGS. 20 A and C prior to assembly from a side view according to one embodiment of the invention.
Figure 20F:
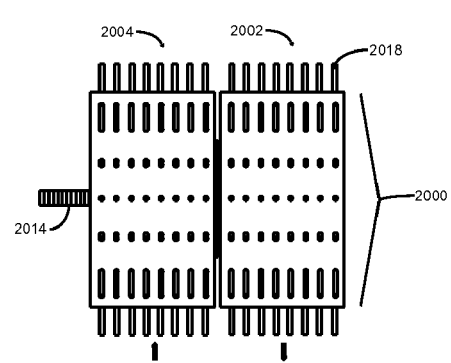
FIG. 20F schematically depicts an assembled rotary mechanism from FIG. 20E from a side view.

FIGS. 19 A and B schematically illustrate various exemplary rotary mechanisms from front elevational views. As shown in FIG. 19A, for example, the drive mechanism of rotary mechanism 1900 includes belt drive 1902. As shown in FIG. 19B, the drive mechanism of rotary mechanism 1904 includes drive chain 1906.

FIGS. 20 A-F schematically illustrate a rotary mechanism or components thereof according to another exemplary embodiment of the invention. As shown, rotary mechanism 2000 includes rotary unit 2002 and rotary unit 2004. First gear component 2006 and gear structure 2008 are disposed on a first side of rotational component 2010 of rotary unit 2002. In this exemplary embodiment, gear structure 2008 is similar to gear structure 610, as described above. Further, gear structure 2008 is retained and rotatably coupled with rotational component 2010 via a retaining mechanism similar to that described above for rotary unit 600. Rotary unit 2002 also includes drive mechanism component 2012 (shown as a shaft) extending from and substantially coaxially aligned with first gear component 2006. As shown, drive mechanism component 2012 includes male threaded region 2014. A second side of rotational component 2010 includes female threaded region 2016, which is configured to receive, e.g., a male threaded region 2014 from another rotary unit 2002. Similarly, male threaded region 2014 of drive mechanism component 2012 of rotary unit 2002 is configured to be received by a female threaded region, such as a female threaded region 2016 of another rotary unit 2002. As also shown in this representative embodiment, a surface of rotational component 2010 includes implements 2018 (shown as bristles that can be adapted for use in, e.g., dental, household cleaning, and other applications).

Rotary mechanism 2000 also includes rotary unit 2004, which includes second gear component 2020 on a second side of rotational component 2021. Second gear component 2020 substantially defines gear structure receiving area 2022 and is configured to operably engage the third gear components of gear structure 2008 of rotary unit 2002 when gear structure 2008 of rotary unit 2002 is positioned in gear structure receiving area 2022 of rotary unit 2004, as shown, for example, in FIG. 20F. Rotary unit 2004 also includes drive mechanism receiving area 2024 (shown as a hole or orifice) disposed through rotational component 2021. As schematically depicted, for example, in FIGS. 20 E and F, drive mechanism receiving area 2024 is configured to receive and rotate around drive mechanism component 2012 such that rotational component 2010 and rotational component 2021 counter-rotate relative to one another during operation. In this embodiment, a surface of rotational component 2021 includes implements 2018.

FIGS. 21 A-F schematically depict a rotary mechanism or components thereof according to another representative embodiment of the invention. As shown, rotary mechanism 2100 includes rotary unit 2102 and rotary unit 2104. Rotary unit 2102 is essentially the same as rotary unit 300, as described herein, but it lacks first gear component 304. Rotary unit 2104 is also similar to rotary unit 300, but lacks a gear structure receiving area and gear structure 308. Rotary unit 2104 does include drive mechanism component 2106 on a first surface of its rotational component and drive mechanism component receiving area 2108 in a second surface of its rotational component. In an assembled rotary mechanism 2100, drive mechanism component 2106 of rotary unit 2104 is received through drive mechanism receiving area 316 of rotary unit 2102, which rotates around drive mechanism component 2106. In addition, drive mechanism component 2106 of rotary mechanism 2100 can be received by drive mechanism component receiving area 2108 of another rotary unit 2104 or rotary mechanism 2100 such that more than two rotary units can be operably connected to one another.

Figure 22A:
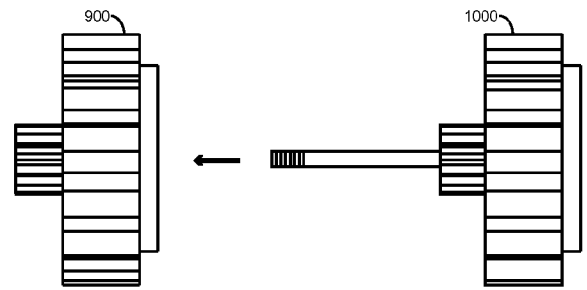
FIG. 22A schematically shows rotary units prior to assembly of a rotary mechanism from side views according to one embodiment of the invention.
Figure 22B:
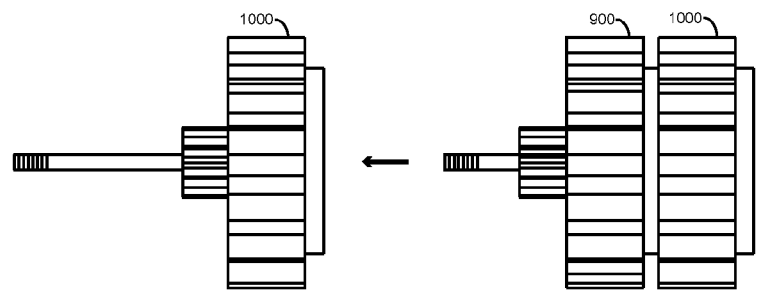
FIG. 22B schematically shows a partially assembled rotary mechanism with the rotary units of FIG. 22A from side views.
Figure 22C:
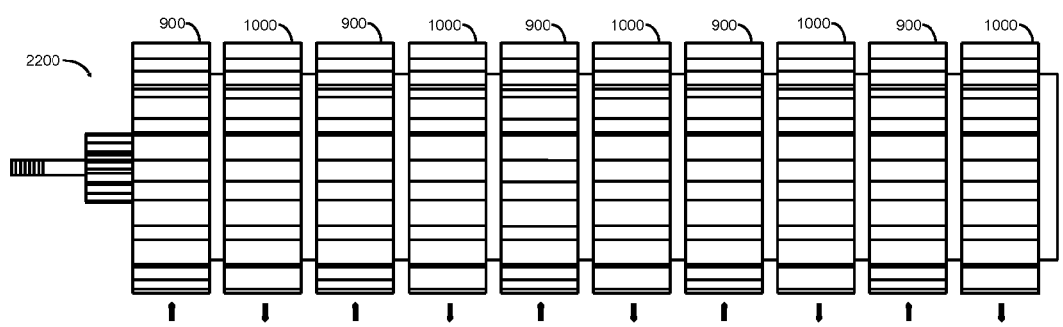
FIG. 22C schematically illustrates a rotary mechanism that includes the rotary units of FIG. 22A from a side view.

To further illustrate, FIGS. 22 A-C schematically show rotary mechanism 2200 assembled from pairs of rotary units 900 and 1000, which are both described further herein. More specifically, FIG. 22A schematically shows an individual pair of rotary units 900 and 1000 prior to assembly of rotary mechanism 2200 from side views. FIG. 22B schematically shows partially assembled rotary mechanism 2200 with the rotary units of FIG. 22A from side views. FIG. 22C schematically illustrates rotary mechanism 2200 that includes multiple pairs of rotary units 900 and 1000.

IV. Exemplary Applications

Figure 23A:
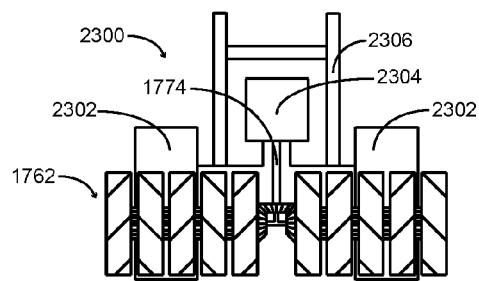
FIG. 23A schematically illustrates a rotor tiller that includes a rotary mechanism from a front elevational view according to one embodiment of the invention.
Figure 23B:
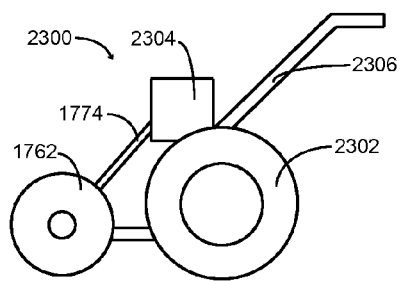
FIG. 23B schematically illustrates the rotor tiller from FIG. 23A from a side elevational view.

FIGS. 23 A and B schematically illustrate a rotor tiller or rototiller that includes a rotary mechanism according to one embodiment of the invention. As shown, rotor tiller 2300 includes rotary mechanism 1762 that is operably connected to motor 2304 via shaft 1774. As also shown, rotor tiller 2300 also includes wheels 2302 and handle 2306 coupled to a support structure.

Figure 24A:
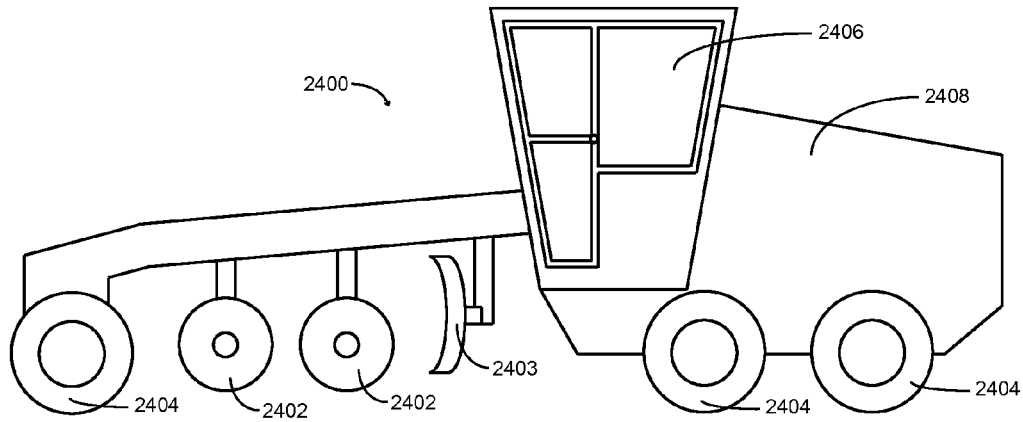
FIG. 24A schematically illustrates a vehicle that includes rotary mechanisms from a side elevational view according to one embodiment of the invention.
Figure 24B:
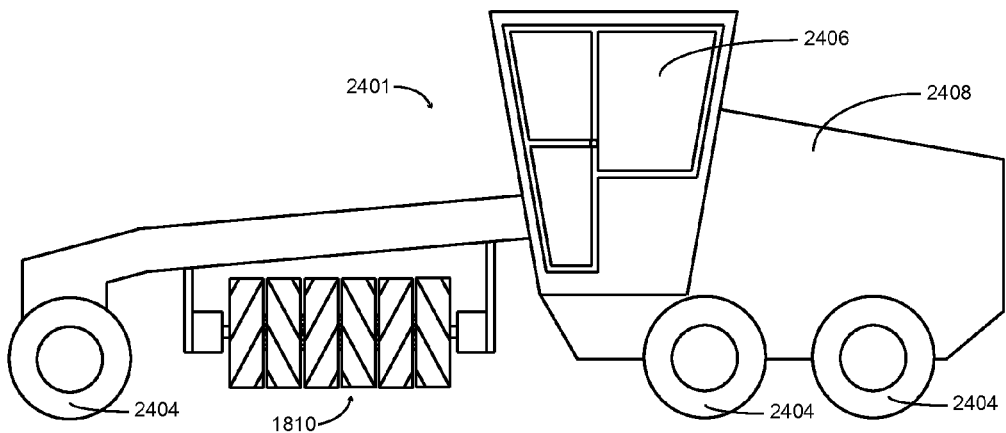
FIG. 24B schematically illustrates a vehicle that includes rotary mechanisms from a side elevational view according to one embodiment of the invention.

To further illustrate exemplary embodiments of the invention, FIG. 24A schematically shows vehicle 2400 from a side elevational view. As shown, vehicle 2400 includes two rotary mechanisms 2402 and grading blade 2403, which can each be independently raised and lowered. Rotary mechanisms can include various embodiments, including various types of implements (e.g., as described herein or the like). As also shown, vehicle 2400 also includes wheels 2404, driver's compartment 2406, and engine compartment 2408. Vehicle 2400 can be adapted for a wide variety of uses in, e.g., agricultural, construction, military, or other applications. In some embodiments, for example, vehicle 2400 is used to till, grade, and/or otherwise move soil. As another exemplary illustration, FIG. 24B schematically shows vehicle 2401 from a side elevational view. As shown, vehicle 2401 includes rotary mechanism 1810, which can be raised and lowered. As also shown, vehicle 2401 also includes wheels 2404, driver's compartment 2406, and engine compartment 2408. Vehicle 2401 can be adapted for a wide variety of uses. In some embodiments, for example, vehicle 2401 is used to till, grade, and/or otherwise move soil.

In other representative embodiments, the invention provides hair cutting devices, e.g., for cutting facial hair, leg hair, or hair on other body parts. To illustrate, FIGS. 25 A-G illustrate various aspects of a hair cutting device according to one embodiment of the invention. As shown, hair cutting device 2500 includes housing 2502, which comprises surfaces that define cavity 2504 disposed at least partially within housing 2502. Housing 2502 also includes opening 2506 that communicates with cavity 2504. Rotary mechanism 2508 (e.g., similar to the rotary mechanism described with respect to FIG. 22C) is at least partially disposed within cavity 2504. Rotary mechanism 2508 includes multiple rotational components 2510 and 2512 (such as the rotational components described with respect to FIGS. 9 A-C and 10 A-C, etc.) that are configured to substantially coaxially rotate (e.g., coaxially counter-rotate) relative to one another. Rotational components 2510 and 2512 also include cutting implements 2514 (e.g., razor blades or other sharp edges) that are configured to cut hair via opening 2506 when the multiple rotational components 2510 and 2512 substantially coaxially rotate relative to one another and cutting implements 2514 (see, e.g., implements 916 and 1018 or the like) contact the hair (see, e.g., FIG. 25F). Rotary mechanism 2508 also includes at least one counter-rotational mechanism, as described herein (see, e.g., the multiple assembled rotational mechanisms schematically depicted in, e.g., FIGS. 22 A-C or the like), operably coupled to the multiple rotational components 2510 and 2512. The counter-rotational mechanism is configured to effect substantially simultaneous counter-rotation of the multiple rotational components 2510 and 2512 relative to one another when movement of at least a portion of the counter-rotational mechanism is effected. That is, rotational component 2510 is configured to rotate in a direction that is opposite the direction of rotation of rotational component 2512. In some embodiments, the rotational components are configured to coaxially counter-oscillate relative to one another about an axis of rotation of the rotary mechanism. In some of these embodiments, cutting implements include dual-side cutting edges, e.g., to cutting hair in both directions of the oscillation.

As also shown, hair cutting device 2500 also includes a drive mechanism operably coupled to the counter-rotational mechanism and rotational components. In the embodiment shown, for example, in FIGS. 25A and 25C, the drive mechanism includes motor 2516 (e.g., a stepper motor, a servo motor, etc.), which is configured to effect movement of the counter-rotational mechanism via shaft 2518 such that the multiple rotational components 2510 and 2512 substantially simultaneously counter-rotate relative to one another. As also shown, switch 2517 (e.g., on/off switch, a variable speed control switch, and/or the like) is operably connected to motor 2516. Although not shown, hair cutting device 2508 also typically includes a power source (e.g., a power cord that plugs into a wall socket, a battery (rechargeable or not), a photovoltaic cell, etc.) operably connected to motor 2516.

Figure 25A:
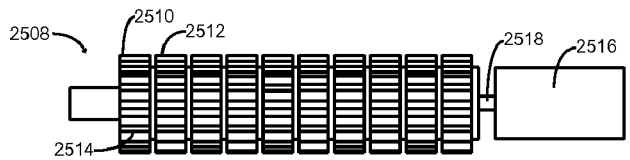
FIG. 25A schematically shows a rotary mechanism of a hair cutting device from a side elevational view according to one embodiment of the invention.
Figure 25B:
FIG. 25B schematically shows a removable structure of a hair cutting device from a side elevational view according to one embodiment of the invention.
Figure 25C:
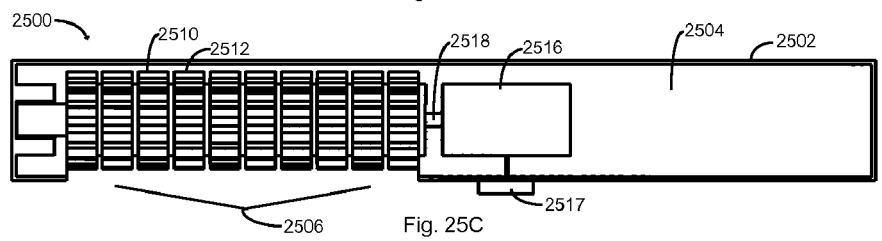
FIG. 25C shows the rotary mechanism of FIG. 25A positioned in a housing of a hair cutting device from a partial cross-sectional view according to one embodiment of the invention.
Figure 25D:
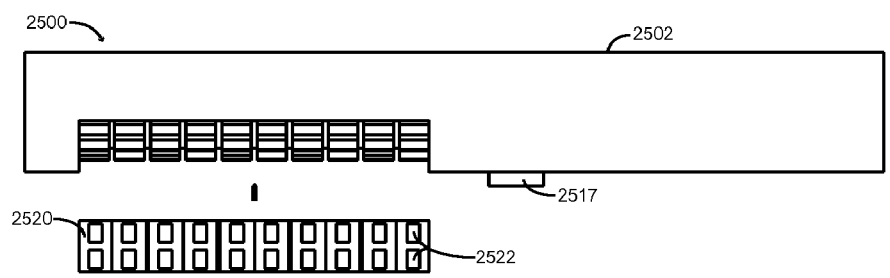
FIG. 25D schematically shows the rotary mechanism of FIG. 25A positioned in a housing of a hair cutting device prior to placing a removable structure in an opening of the housing from side elevational views according to one embodiment of the invention.
Figure 25E:
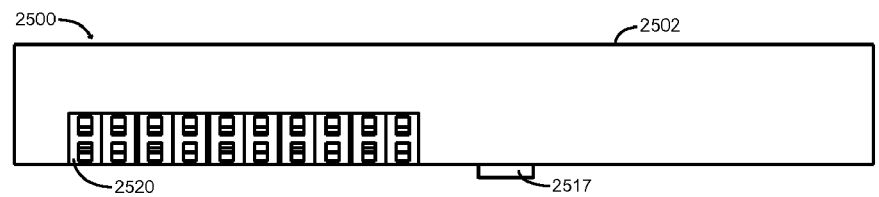
FIG. 25E schematically shows the hair cutting device from FIG. 25D with the removable structure positioned in the opening of the housing from a side elevational view according to one embodiment of the invention.
Figure 25F:
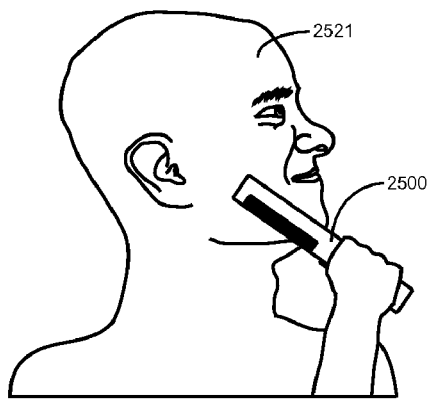
FIG. 25F schematically illustrates a person shaving facial hair using the hair cutting device from FIG. 25E from a side elevational view according to one embodiment of the invention.
Figure 25G:
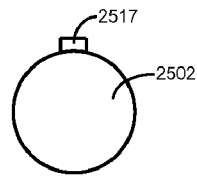
FIG. 25G schematically illustrates a cross-section of the hair cutting device from FIG. 25E.
Figure 26D:
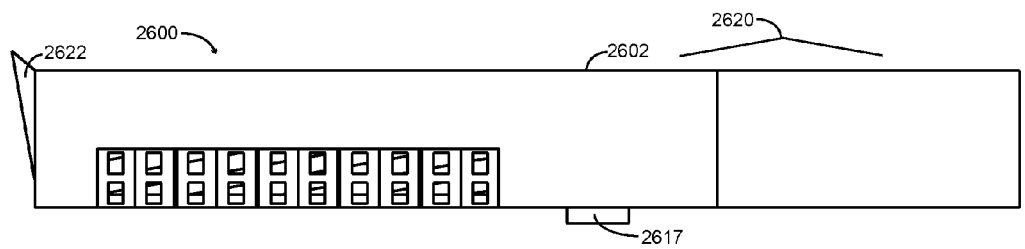
FIG. 26D schematically shows the hair cutting device from FIG. 26C with the removable structure positioned in the opening of the housing from a side elevational view according to one embodiment of the invention.
Figure 26C:
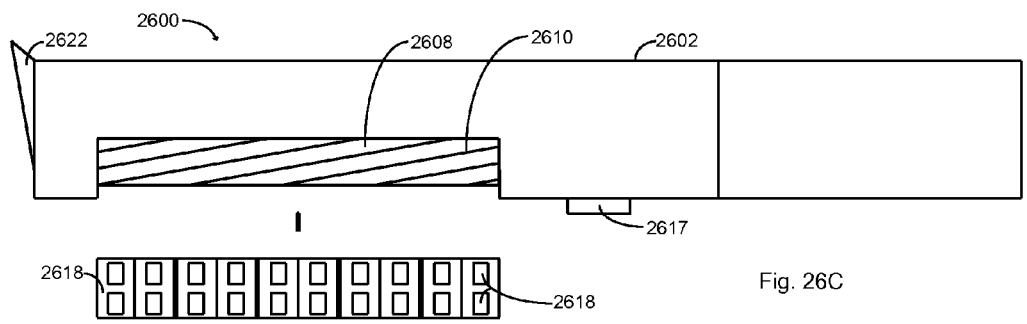
FIG. 26C schematically shows the rotary mechanism of FIG. 26A positioned in a housing of a hair cutting device prior to placing a removable structure in an opening of the housing from side elevational views according to one embodiment of the invention.
Figure 26B:
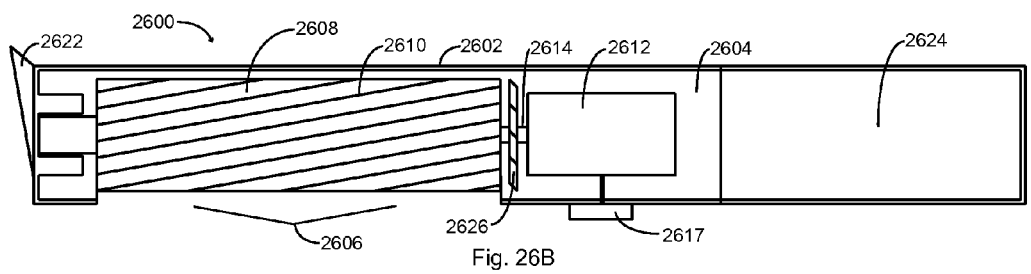
FIG. 26B schematically shows the rotary mechanism of FIG. 26A positioned in a housing of a hair cutting device from a partial cross-sectional view according to one embodiment of the invention.
Figure 26A:
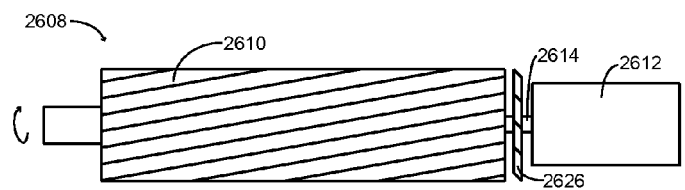
FIG. 26A schematically shows a rotary mechanism of a hair cutting device from a side elevational view according to one embodiment of the invention.

Hair cutting device 2500 also includes removable structure 2520 (e.g., a shaving foil structure or the like) disposed in opening 2506. Removable structure 2520 comprises holes 2522 via which hair is cut when the multiple rotational components 2510 and 2512 substantially coaxially counter-rotate relative to one another and cutting implements 2514 contact the hair. Hair cutting devices also typically include support structures that are structured to support at least a portion of the rotational components, the counter-rotational mechanism, and/or the drive mechanism within the device housings. As shown in FIG. 25F, for example, hair cutting device 2500 is dimensioned to be hand-held (i.e., person 2521 is holding hair cutting device 2500 in his hand). As shown, e.g., FIG. 25G housing 2502 of hair cutting device 2500 comprises at least one substantially circular cross-section.

FIGS. 26 A-D schematically illustrate another exemplary embodiment of a hair cutting device. As shown, hair cutting device 2600 includes housing 2602 that comprises surfaces defining cavity 2604 disposed at least partially within housing 2602 and opening 2606 that communicates with cavity 2604. Hair cutting device 2600 also includes rotary mechanism 2608 at least partially disposed within cavity 2604. Rotary mechanism 2608 comprises cutting implements 2610 that are configured to cut hair via opening 2606 when at least a portion of rotary mechanism 2608 rotates and cutting implements 2610 (e.g., razors or other sharp edges) contact the hair.

Hair cutting device 2600 also includes a drive mechanism (shown as comprising motor 2612 coupled to rotary mechanism 2608 via shaft 2614) operably coupled to rotary mechanism 2608 and positioned substantially parallel with an axis of rotation of rotary mechanism 2608. As also shown, switch 2617 (e.g., on/off switch, a variable speed control switch, and/or the like) is operably connected to motor 2612. Although not shown, hair cutting device 2600 also typically includes a power source (e.g., a power cord that plugs into a wall socket, a battery (rechargeable or not), a photovoltaic cell, etc.) operably connected to motor 2612. The drive mechanism is configured to effect rotation of rotary mechanism 2608 at least partially around the axis of rotation. In some embodiments, the rotary mechanism is configured to oscillate about the axis of rotation. In some of these embodiments, cutting implements include dual-side cutting edges, e.g., to cutting hair in both directions of the oscillation. The drive mechanism (e.g., including motor 2612 and shaft 2614) is at least partially disposed within handle portion 2620 of housing 2602. As shown, the drive mechanism is substantially coaxially positioned relative to the axis of rotation of the rotary mechanism. Although other cross-sectional shapes are optionally utilized, in the representative embodiment shown in, e.g., FIGS. 26B-D, housing 2602 of hair cutting device 2600 comprises at least one substantially circular cross-section, e.g., similar to housing 2504 schematically shown in FIG. 25G. In the embodiment shown, hair cutting device 2600 is dimensioned to be hand-held. As also shown, hair cutting device 2600 includes removable structure 2616 disposed in opening 2606. Removable structure 2616 comprises holes 2618 via which hair is cut when rotary mechanism 2608 at least partially rotates around the axis of rotation and cutting implements 2610 contact the hair.

As also shown, hair cutting device 2600 also comprises linear cutting component 2622. In the embodiment shown, linear cutting component 2622 fixedly extends from an external surface of housing 2602. In other exemplary embodiments, linear cutting components retractably extend from external surfaces of hair cutting device housings.

Hair cutting device 2600 additionally includes waste collection component 2624 operably connected to housing 2602 and is formed within at least a portion of cavity 2604. Waste collection component 2624 is detachable from the housing 2602. Hair cutting device 2600 also includes waste conveyance component 2626 at least partially disposed within housing 2602. Waste conveyance component 2626 is configured to convey waste at least from an area of cavity 2604 that comprises rotary mechanism 2608 to waste collection component 2624, e.g., by creating a suction force that draws waste (e.g., cut hair, etc.) into waste collection component 2624 as rotary mechanism 2608 rotates.

To further illustrate, FIGS. 27A-D schematically show another representative hair cutting device embodiment. As shown, hair cutting device 2700 includes housing 2702, which comprises surfaces that define cavity 2704 disposed at least partially within housing 2702. Housing 2702 also includes opening 2706 that communicates with cavity 2704. Rotary mechanism 2708 is at least partially disposed within cavity 2704. Rotary mechanism 2708 includes multiple rotational components 2710 that are configured to substantially coaxially counter-rotate relative to one another. Rotational components 2710 also include cutting implements 2712 (e.g., razor blades or other sharp edges) that are configured to cut hair via opening 2706 when the multiple rotational components 2710 substantially coaxially rotate relative to one another and cutting implements 2712 contact the hair (see, e.g., FIG. 27D). Rotary mechanism 2708 also includes at least one counter-rotational mechanism, as described herein (see, e.g., rotary mechanism 1810 schematically depicted in, e.g., FIG. 18B, or adapted from the rotary mechanism schematically shown in, e.g., FIGS. 22 A-C), operably coupled to the multiple rotational components 2710. The counter-rotational mechanism is configured to effect substantially simultaneous counter-rotation of the multiple rotational components 2710 relative to one another when movement of at least a portion of the counter-rotational mechanism is effected. That is, one rotational component 2710 is configured to rotate in a direction that is opposite the direction of rotation of an adjacent rotational component 2710 as schematically illustrated, e.g., by the directional arrows shown in FIG. 27A.

Hair cutting device 2700 also includes a drive mechanism (shown as comprising motors 2716 coupled to rotary mechanism 2708 via shaft 2716) operably coupled to rotary mechanism 2708 and positioned substantially parallel with an axis of rotation of rotary mechanism 2708. Switch 2718 (e.g., on/off switch, a variable speed control switch, and/or the like) is operably connected to motors 2727. Although not shown, hair cutting device 2700 also typically includes a power source (e.g., a power cord that plugs into a wall socket, a battery (rechargeable or not), a photovoltaic cell, etc.) operably connected to motors 2714. The drive mechanism is configured to effect rotation of rotary mechanism 2708 at least partially around the axis of rotation. In some embodiments, the rotary mechanism is configured to oscillate about the axis of rotation. In some of these embodiments, cutting implements include dual-side cutting edges, e.g., to cutting hair in both directions of the oscillation. As shown in FIG. 27D, for example, hair cutting device 2700 is dimensioned to be handheld (i.e., person 2726 is holding hair cutting device 2700 in his hand). As also shown, hair cutting device 2700 includes removable structure 2720 disposed in opening 2706. Removable structure 2720 comprises holes 2722 via which hair is cut when rotary mechanism 2708 at least partially rotates around the axis of rotation and cutting implements 2712 contact the hair. Hair cutting device 2700 additionally includes waste collection component 2724 operably connected to housing 2702 and is formed within at least a portion of cavity 2704. Waste collection component 2724 is detachable from the housing 2702. Although not shown, in some embodiments, hair cutting device 2700 also includes at least one linear cutting component.

In other aspects, the invention also provides nail grooming devices. To illustrate, FIGS. 28A-D schematically depict a nail grooming device according to one embodiment of the invention. As shown, nail grooming device 2800 includes housing 2802, which comprises one or more surfaces that define cavity 2804 disposed within housing 2802. In some embodiments, the housing comprises at least one substantially circular cross-section. Nail grooming device 2800 also includes openings 2806, 2808, and 2810 that communicate with cavity 2804. Nail grooming device 2800 also includes rotary mechanism 2812 disposed within cavity 2804. As shown, rotary mechanism 2812 comprises nail grooming implements 2814, 2816, and 2818 (e.g., surfaces of rotary mechanism 2812) that are configured to groom nails (e.g., human finger nails, human toe nails, pet nails, etc.) via openings 2806, 2808, and 2810 when at least a portion of rotary mechanism 2812 rotates and nail grooming implement 2814, 2816, and/or 2818 contacts the nail. Exemplary nail grooming implements are described further herein. In some embodiments, nail grooming devices are dimensioned to be handheld. To illustrate, FIG. 28D schematically illustrates nail grooming device 2800 being held in one hand 2826 of a person and addressing a finger nail on finger 2828 on the other hand of the person.

Nail grooming device 2800 also includes a drive mechanism (e.g., including motor 2820 and shaft 2822) operably coupled to rotary mechanism 2812. The drive mechanism is configured to effect rotation of rotary mechanism 2812 at least partially around an axis of rotation. In some embodiments, rotary mechanism 2812 is configured to oscillate about the axis of rotation. As shown, for example, in FIGS. 28 A and B, in some embodiments, at least a portion of the drive mechanism is positioned substantially parallel with an axis of rotation of rotary mechanism 2812. As further shown, for example, in FIGS. 28 A and B, in some embodiments, at least a portion of the drive mechanism is substantially coaxially positioned relative to an axis of rotation of rotary mechanism 2812. In some embodiments, drive mechanisms comprises drive shafts, chain drives, belt drives, gear drives, and/or the like. In some embodiments, at least the drive mechanism is at least partially disposed within a handle portion of a nail grooming device housing. To illustrate, motor 2820 and shaft 2822 are disposed within handle 2823 of housing 2802 of nail grooming device 2800. As shown, for example, in FIGS. 28 A and B, in some embodiments, the drive mechanism is substantially coaxially positioned relative to the axis of rotation of rotary mechanism 2812. Switch 2824 (e.g., on/off switch, a variable speed control switch, and/or the like) is operably connected to motor 2820. Although not shown, nail grooming device 2800 also typically includes a power source (e.g., a power cord that plugs into a wall socket, a battery (rechargeable or not), a photovoltaic cell, etc.) operably connected to motor 2820.

Essentially any type of nail grooming implement can be adapted for use with or in the nail grooming devices of the invention. In some embodiments, for example, nail grooming implements comprises nail filing components and/or nail buffing components. In some embodiments, nail grooming implements comprise at least one substantially flat surface (see, e.g., nail grooming implements 2814, 2816, and 2818 of nail grooming device 2800) that is configured to rotate proximal to nail grooming device openings. In some embodiments, nail grooming implements comprise at least one curved surface that is configured to rotate proximal to nail grooming device openings. In some embodiments, nail grooming implements comprise at least one groove that is configured to rotate proximal to nail grooming device openings. In some embodiments, nail grooming implements comprise at least one abrasive surface that is configured to rotate proximal to nail grooming device openings. For example, nail grooming implements 2814, 2816, and 2818 of nail grooming device 2800 typically include different abrasive or buffing surfaces. In some embodiments, nail grooming implements comprise at least one glass file that is configured to rotate proximal to nail grooming device openings. In some embodiments, rotary mechanisms comprise multiple nail grooming implements (see, e.g., nail grooming implements 2814, 2816, and 2818 of nail grooming device 2800), whereas in other embodiments, rotary mechanisms comprise only a single nail grooming implement.

In some embodiments, nail grooming devices comprise at least one movable door disposed proximal to the opening, which door is configured to move at least between an open position and a closed position. In some embodiments, nail grooming devices include at least one nail cutting component (e.g., an electric nail clipping mechanism operably connected to a device motor and housing). In some embodiments, nail grooming devices include at least one removable structure disposed in or proximal to device openings, which removable structure comprises at least one hole via which the nail is groomed when the rotational components substantially coaxially rotate relative to one another and the cutting implement contacts the nail.

In some embodiments, the nail grooming device includes a waste collection component operably connected to the housing. As schematically illustrated, for example, in FIG. 28B, waste collection component 2830 is operably connected to housing 2802 of nail grooming device 2800. In some embodiments, at least a portion of the cavity comprises the waste collection component. In some embodiments, the waste collection component is detachable from the housing (see, e.g., waste collection component 2830 of nail grooming device 2800). In some embodiments, the nail grooming device includes at least one waste conveyance component at least partially disposed within the housing, which waste conveyance component is configured to convey waste at least from an area of the cavity that comprises the rotary mechanism to the waste collection component.

Figures 29A, 29B, 29C:
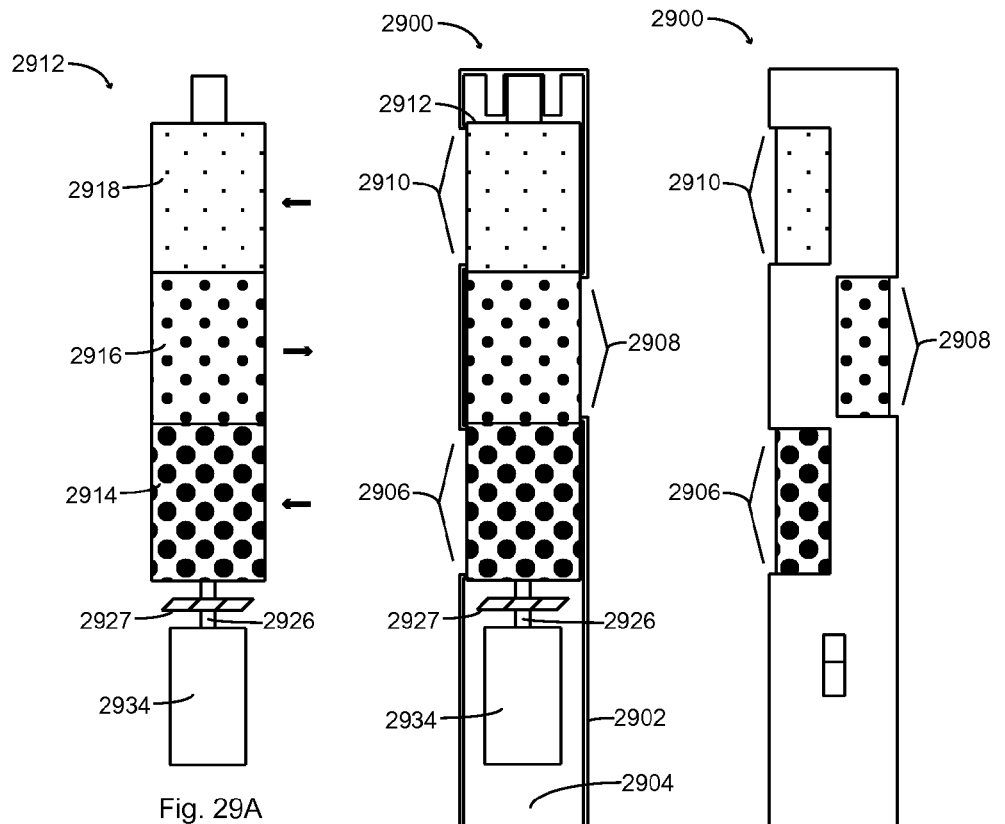
FIG. 29A schematically shows a rotary mechanism of a nail grooming device from a side elevational view according to one embodiment of the invention.
FIG. 29B schematically shows the rotary mechanism of FIG. 29A positioned in a housing of a nail grooming device from a partial cross-sectional view according to one embodiment of the invention.
FIG. 29C schematically shows the nail grooming device from FIG. 29B from a side elevational view according to one embodiment of the invention.

In other embodiments, the invention provides nail grooming devices with rotary mechanisms having rotational components that are configured to counter-rotate relative to one another. One embodiment of such a device is schematically shown in FIGS. 29A-C. As shown, nail grooming device 2900 includes housing 2902 that comprises surfaces defining cavity 2904 disposed at least partially within housing 2902. Housing 2902 also includes openings 2906, 2908, and 2910 that communicate with cavity 2904. Nail grooming device 2900 also includes rotary mechanism 2912 at least partially disposed within cavity 2904. Rotary mechanism 2912 includes rotational components 2914, 2916, and 2918 that are configured to substantially coaxially rotate relative to one another. Rotational components typically comprise or are operably coupled to at least one nail grooming implement that is configured to groom at least one nail via the opening when the rotational components substantially coaxially rotate relative to one another and the nail grooming implement contacts the nail. In the embodiment shown, surfaces of rotational components 2914, 2916, and 2918 comprise nail grooming implements, such as abrasive or buffing materials. In some embodiments, housing 2902 comprises at least one substantially circular cross-section. In some embodiments, nail grooming devices includes a friction reducing material (e.g., polytetrafluoroethylene, oil, or another lubricant, etc.) disposed between rotational components to reduce friction between the rotational components when the rotational components substantially coaxially rotate relative to one another.

Figure 29D:
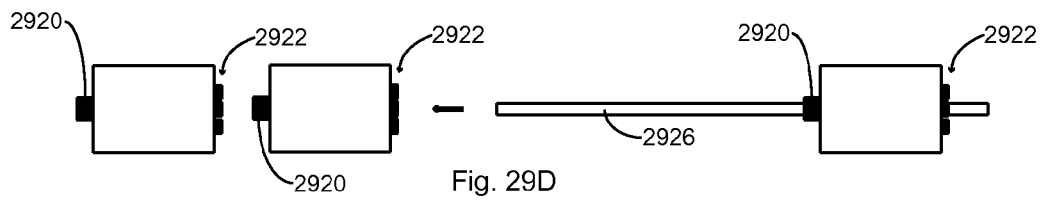
FIG. 29D schematically shows components of a counter-rotational mechanism of the rotary mechanism of FIG. 29A from side elevational views prior to assembly according to one embodiment of the invention.
Figure 29E:
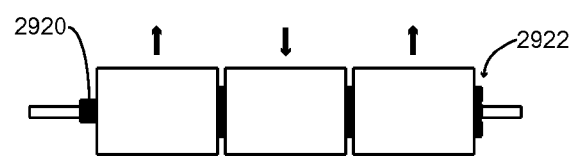
FIG. 29E schematically shows components of a counter-rotational mechanism of the rotary mechanism of FIG. 29A from side elevational views following partial assembly according to one embodiment of the invention.
Figures 29F, 29G:
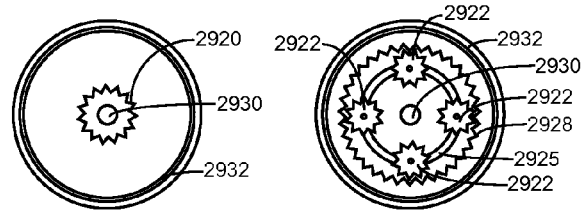
FIG. 29F schematically shows components of a counter-rotational mechanism of a rotational component of the rotary mechanism of FIG. 29A from a front side elevational view according to one embodiment of the invention.
FIG. 29G schematically shows components of a counter-rotational mechanism of a rotational component of the rotary mechanism of FIG. 29A from a back side elevational view according to one embodiment of the invention.

Nail grooming device 2900 also includes a counter-rotational mechanism (e.g., gear components) operably coupled to rotational components 2914, 2916, and 2918. The counter-rotational mechanism is configured to effect substantially simultaneous counter-rotation of rotational components 2914, 2916, and 2918 relative to one another when movement of at least a portion of the counter-rotational mechanism is effected. To further illustrate, FIG. 29D schematically shows gear components 2920 and 2922 of a counter-rotational mechanism of rotary mechanism 2912 of FIG. 29A from side elevational views prior to assembly according to one embodiment of the invention. FIG. 29E schematically shows gear components 2920 and 2922 of a counter-rotational mechanism of rotary mechanism 2912 of FIG. 29A from side elevational views following partial assembly according to one embodiment of the invention. As shown, gear component 2920 on one rotational component are operably coupled to gear components 2922 on another rotational component via shaft 2926 of a drive mechanism of nail grooming device 2900. To further illustrate, FIG. 29F schematically shows gear component 2920 of a counter-rotational mechanism of a rotational component (e.g., rotational components 2914, 2916, or 2918) of rotary mechanism 2912 from a front side elevational view. FIG. 29G schematically shows gear components 2922 and support component 2925 of a gear structure of a counter-rotational mechanism of the rotational component (e.g., rotational components 2914, 2916, or 2918) of FIG. 29F from a back side elevational view. As shown, gear component 2920 is fixedly coupled to the front end of the rotational component (e.g., rotational components 2914, 2916, or 2918), whereas gear components 2922 are rotatably coupled (e.g., via a gear structure or the like) to the back end of the rotational component (e.g., rotational components 2914, 2916, or 2918). When multiple rotational components are assembled, gear component 2920 on one rotational component engages gear components 2922 of another rotational component. During operation, when a first rotational component rotates in one direction gear component 2920 on that first rotational component engages gear components 2922 on a second rotational component and causes gear components 2922 on the second rotational component to rotate in the opposite direction. Gear components 2922 on the second rotational component, which engage gear component 2928 (e.g., an annulus gear) on the second rotational component, in turn, cause gear component 2928 and the second rotational component to rotate in a direction that is opposite from the direction of rotation of the first rotational component. As also shown in FIGS. 29 F and G, the rotational component includes hole 2930 disposed therethrough. Hole 2930 is configured to receive shaft 2926. As also shown in, e.g., FIGS. 29 F and G, the rotational component includes alignment components 2932 structured to align neighboring pairs of rotational components relative to one another. In some of these embodiments, the alignment components comprise a circular ridge disposed on, extending from, or attached to a surface of a first member of a pair of neighboring rotational components and a circular groove disposed in a surface of a second member of the pair of neighboring rotational components, which circular ridge inserts into and rotates in the circular groove in an assembled rotary mechanism. In some of these embodiments, the alignment components comprise a circular groove disposed in a surface of each member of the pair of neighboring rotational components and a ring disposed the grooves of the pair of neighboring rotational components, which grooves rotate about the ring in an assembled rotary mechanism. In some embodiments, the rotational components are configured to coaxially counter-oscillate relative to one another about an axis of rotation of the rotary mechanism.

Figures 30A, 30B, 30C:
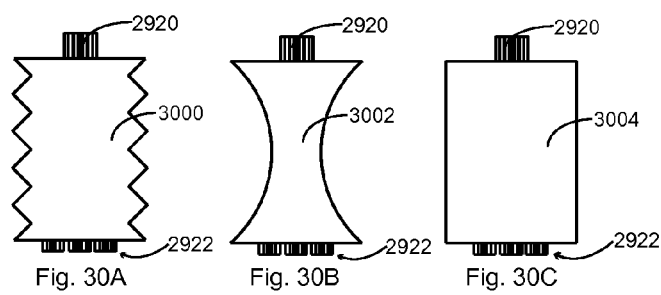
FIG. 30A schematically shows a rotational component from a side elevational view according to one embodiment of the invention.
FIG. 30B schematically shows a rotational component from a side elevational view according to one embodiment of the invention.
FIG. 30C schematically shows a rotational component from a side elevational view according to one embodiment of the invention.
Figure 30D:
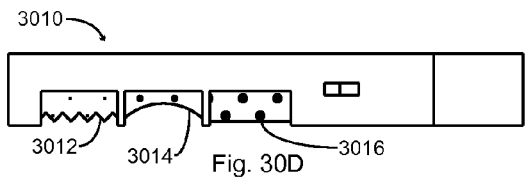
FIG. 30D schematically illustrate a nail grooming device from a side elevational view according to one embodiment of the invention.

The rotational components of the nail grooming devices described herein include many different embodiments. For example, they can include various nail grooming implements. To further illustrate, rotational components can include a wide variety of cross-sectional shapes. Some of these rotational component cross-sectional shapes are schematically illustrated in, e.g., FIGS. 30 A-C, which show rotational components 3000, 3002, and 3004, respectively. To illustrate some additional embodiments, FIG. 30D schematically illustrates nail grooming device 3010, which includes rotational components 3012, 3014, and 3016.

In addition, nail grooming device 2900 also includes a drive mechanism (e.g., including motor 2934 and shaft 2926) operably coupled to rotary mechanism 2912. The drive mechanism is configured to effect movement of at least the portion of the counter-rotational mechanism such that rotational components 2914, 2916, or 2918 substantially simultaneously counter-rotate relative to one another.

Figure 31A:
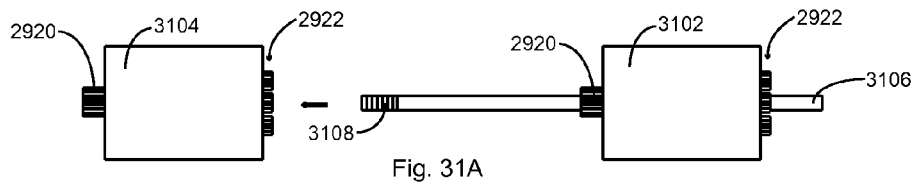
FIG. 31A schematically depicts components of a rotary mechanism prior to assembly from side elevational views according to one embodiment of the invention.
Figure 31B:
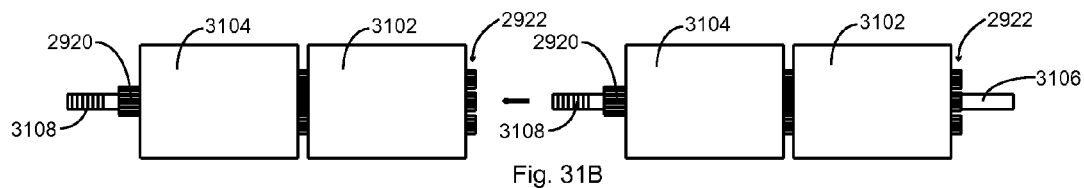
FIG. 31B schematically illustrates components of a rotary mechanism prior to assembly from side elevational views according to one embodiment of the invention.
Figure 31C:
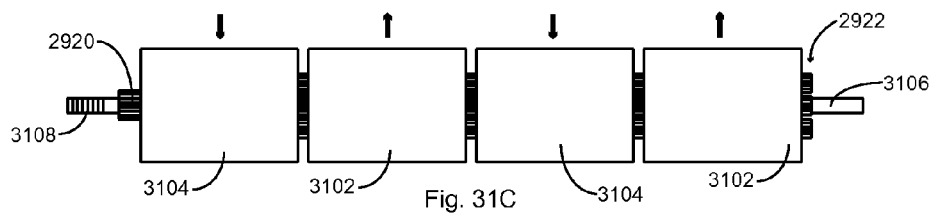
FIG. 31C schematically illustrates a rotary mechanism from a side elevational view according to one embodiment of the invention.

FIGS. 31A-C schematically illustrate another exemplary embodiment of rotary mechanisms. As shown, rotary mechanism 3100 includes rotational components 3102 and 3104. Rotational component 3102 is fixedly coupled to shaft 3106, which includes threaded portion 3108. Rotational component 3104 includes a hole (not within view) through which shaft 3106 is inserted. Rotational component 3104 freely rotates about shaft 3106 and engages gear component on rotational component 3102. Threaded portion 3108 of one unit screws into a receiving threaded portion of another unit (see, e.g., FIG. 31C). As further shown, multiple units can be attached to one another in these embodiments in which individual rotational components 3102 and 3104 are configured to counter-rotate relative to one another.

In some embodiments, the nail grooming implement comprises a nail filing component. In some embodiments, the nail grooming implement comprises a nail buffing component. In some embodiments, the nail grooming implement comprises at least one substantially flat surface that is configured to rotate proximal to the opening. In some embodiments, the nail grooming implement comprises at least one curved surface that is configured to rotate proximal to the opening. In some embodiments, the nail grooming implement comprises at least one groove that is configured to rotate proximal to the opening. In some embodiments, the nail grooming implement comprises at least one abrasive surface that is configured to rotate proximal to the opening. In some embodiments, the nail grooming implement comprises at least one glass file that is configured to rotate proximal to the opening.

In some embodiments, at least the drive mechanism is at least partially disposed within a handle portion of the housing. In some embodiments, the drive mechanism comprises at least one photovoltaic cell. In some embodiments, the drive mechanism is operably coupled to the counter-rotational mechanism and/or the rotational components via at least one drive shaft, at least one drive chain, at least one belt drive, and/or at least one gear drive. In some embodiments, at least a portion of the drive mechanism is substantially coaxially positioned relative to an axis of rotation of the rotary mechanism. In some embodiments, at least a portion of the drive mechanism is positioned substantially parallel with an axis of rotation of the rotary mechanism. In some embodiments, the drive mechanism comprises one or more of: a drive shaft, a chain drive, a belt drive, or a gear drive. In some embodiments, the drive mechanism comprises at least one flexible drive shaft. In some embodiments, the drive mechanism comprises at least one rechargeable battery. In some embodiments, the drive mechanism comprises at least one motor. In some embodiments, the motor comprises at least two drive shafts that are each operably coupled to a separate rotary mechanism.

Figure 32A:
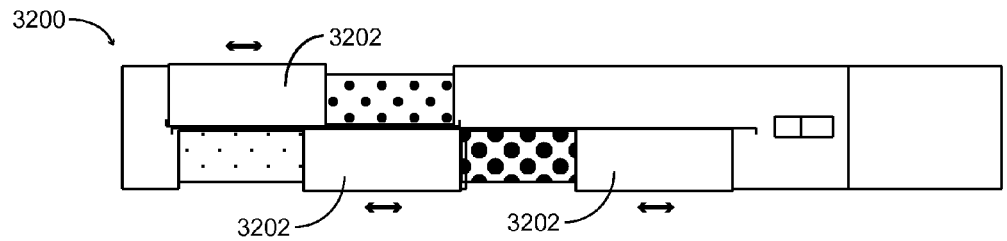
FIG. 32A schematically depicts a nail grooming device that includes doors from a side elevational view according to one embodiment of the invention.
Figure 32B:
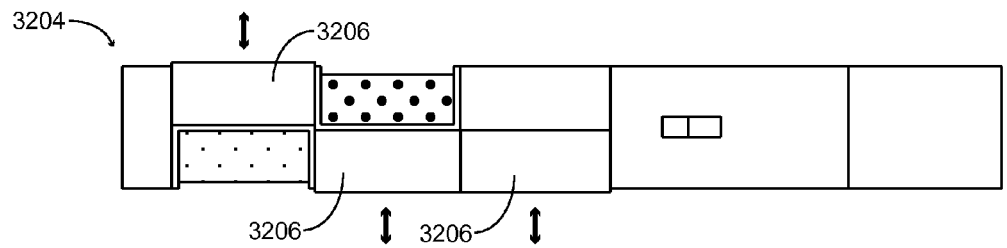
FIG. 32B schematically depicts a nail grooming device that includes doors from a side elevational view according to one embodiment of the invention.

In some embodiments, the nail grooming device includes at least one movable door disposed proximal to the opening, which door is configured to move at least between an open position and a closed position. To illustrate, FIG. 32A schematically depicts nail grooming device 3200 that includes doors 3202, which are configured to move substantially parallel to an axis of rotation of the rotational components of nail grooming device 3200. As shown in FIG. 32B, for example, nail grooming device 3204 that includes doors 3206, which are configured to move substantially perpendicular to an axis of rotation of the rotational components of nail grooming device 3204.

In some embodiments, the nail grooming device includes at least one removable structure disposed in or proximal to the opening, which removable structure comprises at least one hole via which the nail is groomed when the rotational components substantially coaxially rotate relative to one another and the cutting implement contacts the nail. In some embodiments, the nail grooming device includes a support structure structured to support at least a portion of the rotational components, the counter-rotational mechanism, and/or the drive mechanism. In some embodiments, the hair cutting device is dimensioned to be hand-held. In some embodiments, the nail grooming device includes at least one nail cutting component.

In some embodiments, the nail grooming device includes a waste collection component operably connected to the housing. As shown in FIG. 29A, for example, at least portion of cavity 2904 comprises waste collection component 2936. As shown, waste collection component 2936 is detachable from housing 2902. Nail grooming device 2900 also includes waste conveyance component 2927 at least partially disposed within housing 2902. Waste conveyance component 2927 is configured to convey waste at least from an area of cavity 2904 that comprises rotary mechanism 2912 to waste collection component 2936, e.g., by creating a suction force that draws waste (e.g., nail filings, etc.) into waste collection component 2936 as rotary mechanism 2912 rotates.

In some embodiments, the rotational components each comprise one or more alignment components structured to align neighboring pairs of rotational components relative to one another. In some embodiments, the alignment components comprise a circular ridge disposed on, extending from, or attached to a surface of a first member of a pair of neighboring rotational components and a circular groove disposed in a surface of a second member of the pair of neighboring rotational components, which circular ridge inserts into and rotates in the circular groove in an assembled rotary mechanism. In some embodiments, the alignment components comprise a circular groove disposed in a surface of each member of the pair of neighboring rotational components and a ring disposed the grooves of the pair of neighboring rotational components, which grooves rotate about the ring in an assembled rotary mechanism.

In another aspect, the invention provides a drive mechanism that includes at least one motor, and at least one flexible drive shaft operably connected to the motor, which flexible drive shaft is configured to couple with at least one rotational effector component.

Figure 33:
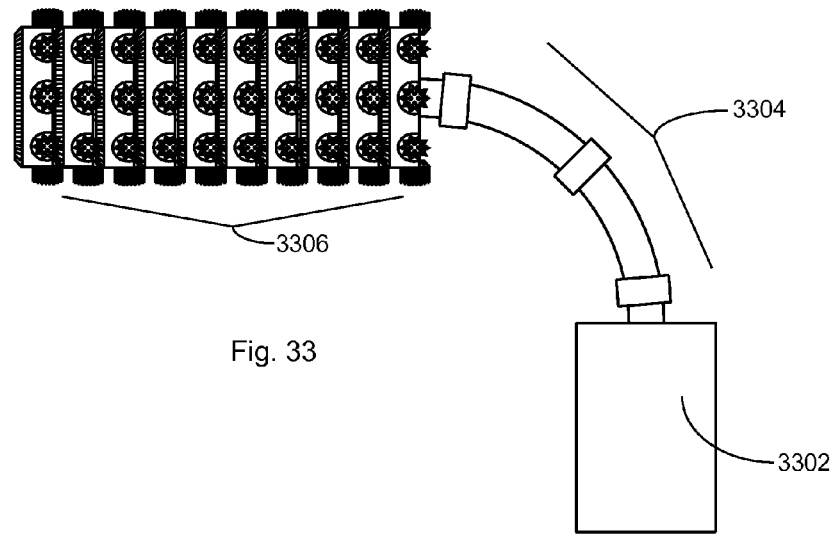
FIG. 33 schematically shows a drive mechanism that includes a flexible drive shaft according to one embodiment of the invention.

In some embodiments, the motor is fixedly coupled to at least one support structure. In some embodiments, the drive mechanism includes at least one guide component disposed proximal to the flexible drive shaft, which guide component is configured to substantially maintain a position of the flexible drive shaft when the motor rotates the flexible drive shaft. To illustrate an exemplary embodiment, FIG. 33 schematically illustrates drive mechanism that includes motor 3302 flexible drive shaft 3304 operably connected to motor 3302, which flexible drive shaft 3304 is configured to couple with rotational effector component 3306.

FIGS. 34 A-D schematically illustrate an exemplary tooth brushing device or components thereof according to one embodiment of the invention. As shown, tooth brushing device 3400 includes rotary mechanism 3402, which includes a plurality of rotary units 800, as described above. Tooth brushing device 3400 also includes toothbrush head component 3404 and handle component 3406. Toothbrush head component 3404 includes rotary mechanism housing 3408, which partially exposes a portion of the bristles of rotary mechanism 3402 through an opening in rotary mechanism housing 3408 during operation. Toothbrush head gear components 3410 and drive shaft 3412 also extend from a portion of rotary mechanism housing 3408. Drive shaft 3412 is received through drive mechanism receiving areas of rotational components 802 of rotary units 800 of rotary mechanism 3402. Toothbrush head gear components 3410 operably engage gear components 804 and 824 of a rotary unit 800 to effect counter rotation of neighboring rotational components 802 and implements 822 of rotary mechanism 3402. Rotary mechanism cap 3414 attaches to drive shaft 3412 to retain rotary mechanism positioned relative to toothbrush head gear components 3410. Handle component 3406 houses a motor (not within view) the operably connects to toothbrush head gear components 3410 and drive shaft 3412. A power source, such as a rechargeable battery or the like is also housed in handle component 3406 is some embodiments. In certain embodiments, the motor is optionally connected to other types of power sources, such as photovoltaic cells attached to handle component 3406, external power sources, or the like. As also shown, handle component 3406 also include switch 3416, which is used, e.g., to turn tooth brushing device 3400 on and off, regulate speeds or modes of rotary unit rotation, or the like.

FIGS. 35 A and B schematically show an exemplary rotary mechanism or toothbrush head component that is optionally used, e.g., with handle component 3406 of tooth brushing device 3400. As shown, rotary mechanism 3500 includes a plurality of rotary units 800 in which implements 3502 (raised elastomeric regions, e.g., for tooth polishing) have been substituted for implements 822 on several individual rotary units. FIG. 35B schematically shows toothbrush head component 3504, which includes rotary mechanism 3500.

FIG. 36 schematically illustrates an exemplary cleaning device from a side view according to one embodiment of the invention. As shown, cleaning device 3600 includes a rotary mechanism that includes rotary units similar to rotary units 800, which are described further herein. Exemplary uses of cleaning device 3600 include cleaning outdoor cooking grills, dishes, and toilets, among many possible applications.

Figure 37A:
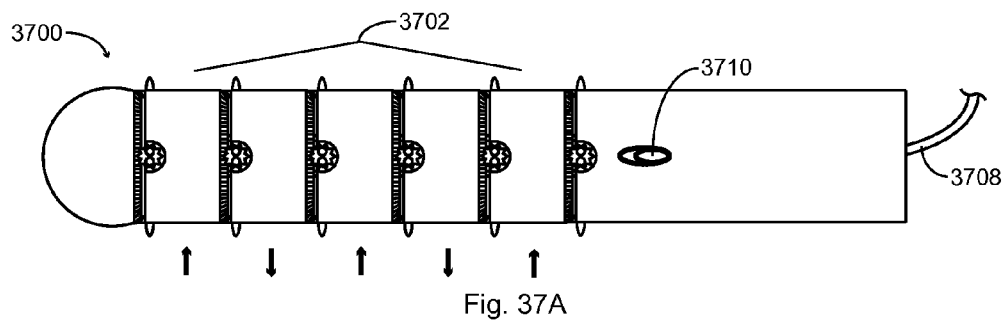
FIG. 37A schematically shows a massaging device from a side view according to one embodiment of the invention.
Figure 37B:
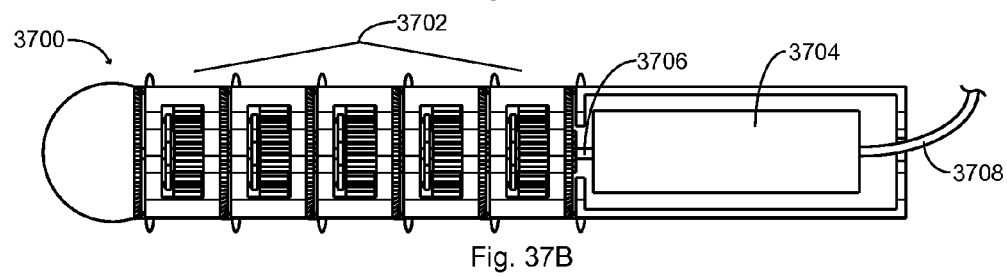
FIG. 37B schematically shows the massaging device of FIG. 37A from a partial sectional view.
Figure 38A:
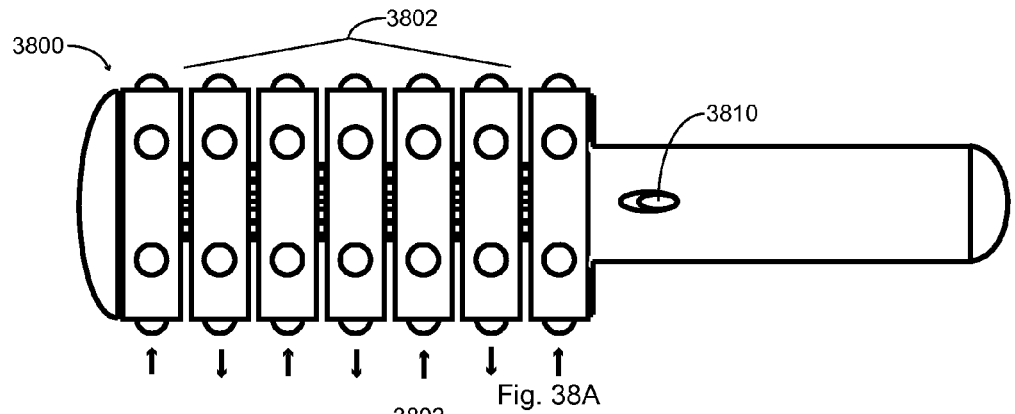
FIG. 38A schematically shows a massaging device from a side view according to one embodiment of the invention.
Figure 38B:
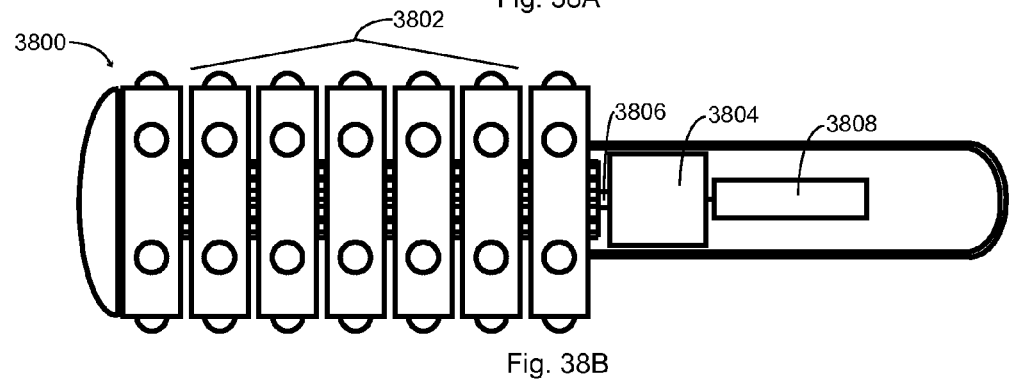
FIG. 38B schematically shows the massaging device of FIG. 38A from a partial sectional view.

To further illustrate, rotary units and rotary mechanisms are also optionally used in various types of massaging devices. For example, FIGS. 37 A and B schematically show one representative massaging device from side and partial sectional views. As shown, massaging device 3700 includes rotary mechanism 3702, which includes a plurality of rotary units 300, as described herein. Rotary mechanism 3702 is operably connected to motor 3704 via shaft 3706, which in this exemplary embodiment is connected to an external power source via power cord 3708. Massaging device 3700 also includes switch 3710 (e.g., an on-off switch or the like). When motor 3704 rotates shaft 3706, neighboring pairs of rotary units in rotary mechanism 3702 counter-rotated relative to one another, as schematically depicted by the accompanying directional arrows in, e.g., FIG. 37A. In certain embodiments, motors used in the devices and other embodiments of the invention can selectively rotate operably connected shafts or the like in, e.g., two directions such that neighboring pairs of rotary units in a given rotary mechanism can counter-rotate in those directions as well. As another example, FIGS. 38 A and B schematically illustrate massaging device 3800 from side and partial sectional views. As shown, massaging device 3800 includes rotary mechanism 3802, which includes a plurality of rotary units 100, as described herein. Rotary mechanism 3802 is operably connected to motor 3804 via shaft 3806, which in this exemplary embodiment is connected to battery 3808 (e.g., a disposable battery, a rechargeable battery, etc.). Massaging device 3800 also includes switch 3810 (e.g., an on-off switch or the like). When motor 3804 rotates shaft 3806, neighboring pairs of rotary units in rotary mechanism 3802 counter-rotated relative to one another, as schematically depicted by the accompanying directional arrows in, e.g., FIG. 38A. In some embodiments, the rotary units of massaging devices are configured to selectively oscillate, rotate in variable speeds, or the like. Optionally, thermal modulators (e.g., heating elements, etc.) are included as part of a massaging device, e.g., so that a user can also select a given temperature to be applied by the device. To further illustrate, vibrational elements are also optionally included as part of a massaging device, e.g., so that a user can also select a vibrational mode during operation of the device. In some embodiments, at least portions of these massaging devices (e.g., regions that include the rotary mechanisms) include flexible coverings (e.g., an elastomeric material or the like).

Figure 39A:
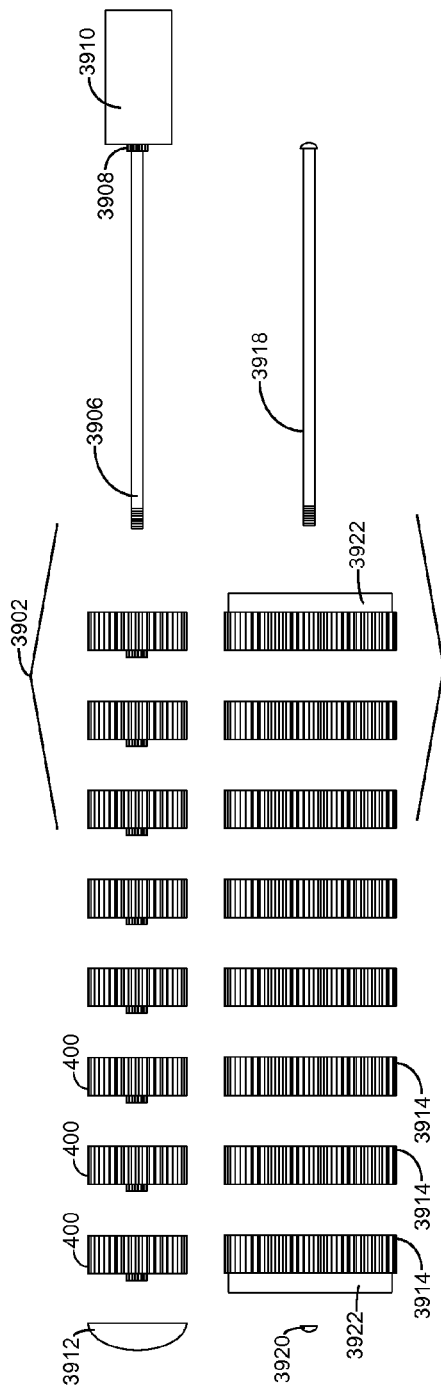
FIG. 39A schematically illustrates an exploded view of a propulsion device according to one embodiment of the invention.
Figure 39B:
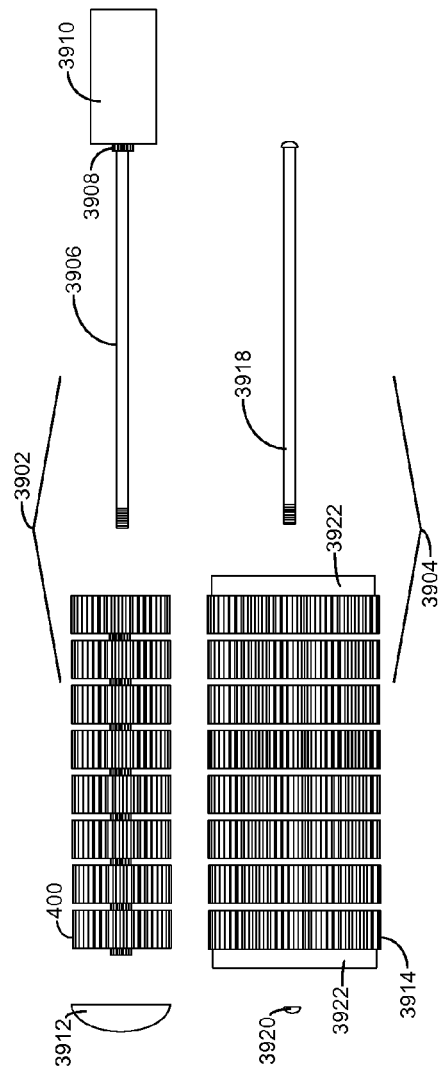
FIG. 39B schematically shows the propulsion device of FIG. 39A from a partially exploded view.

To further illustrate representative embodiments, rotary units and rotary mechanisms are optionally used or adapted for use in various types of engines and other propulsion devices or systems. For example, FIGS. 39 A-F schematically illustrate a propulsion device or components thereof according to one embodiment of the invention. As shown, propulsion device 3900 includes two rotary mechanisms 3902 and propeller component 3904. Rotary mechanisms 3902 include a plurality of rotary units 400, as described herein. Rotary units 400 are operably coupled to one another via shaft 3906, which includes gear component 3908. Shaft 3906 operably connects to motor 3910 and rotary mechanism cap 3912. Gear component 3908 operably engages third gear components 412 of gear structure 410 of a rotary unit 400 such that when motor 3910 effects the rotation of gear component 3908, gear component 3908 effects the counter rotation of neighboring pairs of rotary units 400. Gear components 424 of rotary units 400 operably engage corresponding gear components of propeller units 3914 to effect the counter rotation of neighboring pairs of propeller units 3914 of propeller component 3904, and thereby propulsion. Rotary mechanism cap 3912 aligns and maintains the position of rotary units 400 relative to one another. Although two rotary mechanisms 3902 are depicted in this propulsion device embodiment, fewer or more that two rotary mechanisms are optionally used.

Propeller component 3904 of propulsion device 3900 includes a plurality of propeller units 3914, which in this embodiment each include a plurality of propellers 3916. Many different type of propellers are optionally used or adapted for use in the engines or propulsion devices of the invention. In some embodiments, for example, individual propeller components 3904 may have propellers 3916 that differ in size from the propellers of other propeller components in a given propulsion device 3900. Propeller units 3914 are operably coupled together in propeller component 3904 via propeller component shaft 3918 and propeller component cap 3920. As also shown, certain propeller units 3914 include rotational alignment components 3922, which are positioned and rotate in corresponding rotational positioning components 4007 of propulsion component housing 4000, e.g., to prevent propeller units 3914 from contacting propulsion component housing 4000 during operation. See, e.g., FIGS. 40 D and E.

Figures 41A, 41B:
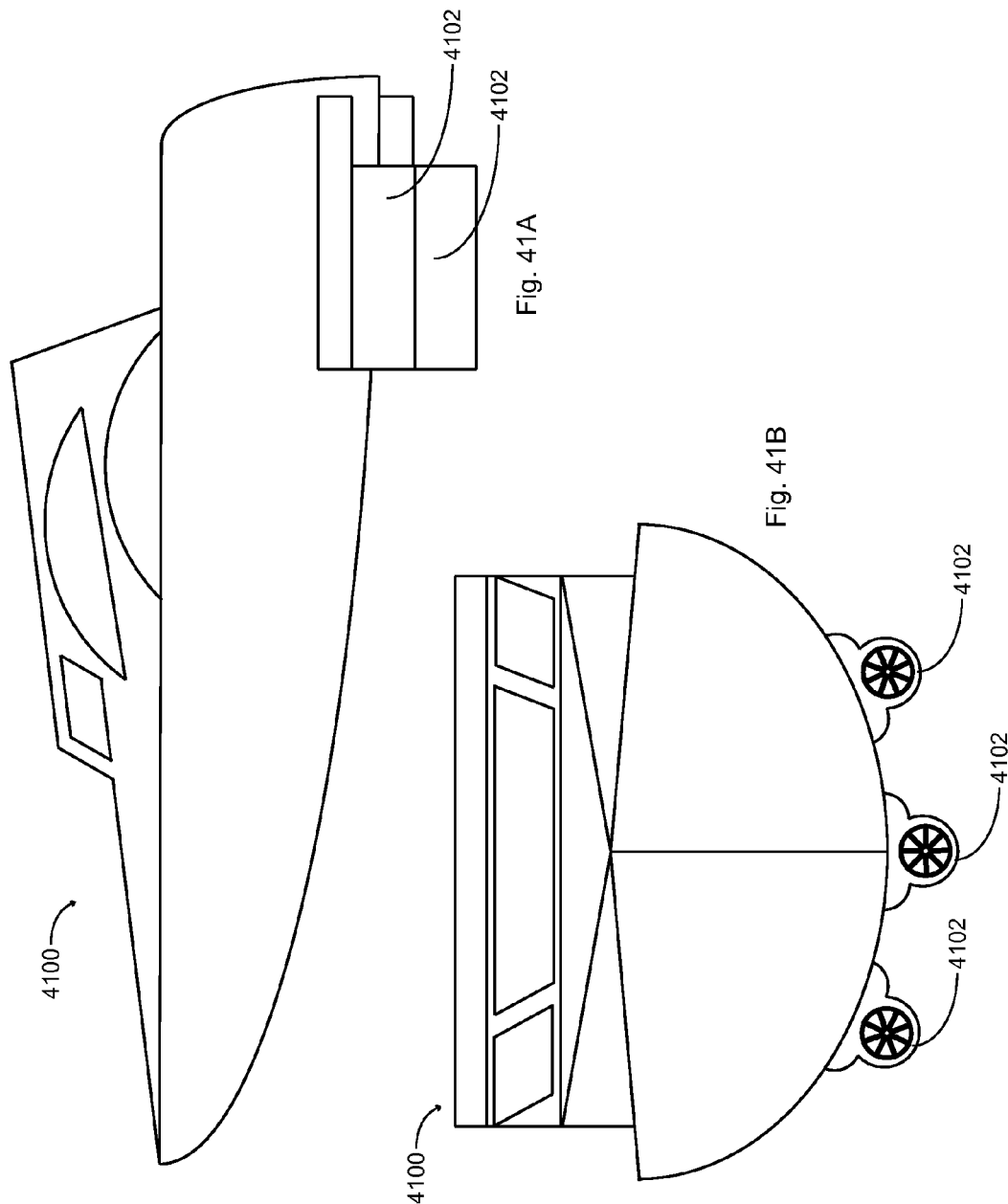
FIG. 41A schematically shows a boat that includes propulsion devices from a side view according to one embodiment of the invention.
FIG. 41B schematically illustrates the boat of FIG. 41A from a front side view.

The engine and propulsion devices have many different uses. For example, they are optionally used or adapted for use with watercraft (e.g., boats, submarines, surfboards, diving or scuba propulsion aides, and the like) or aircraft. To illustrate, FIGS. 41 A and B schematically depict boat 4100, which includes several housed propulsion devices 4102. To further illustrate, FIGS. 42 A and B schematically depict aircraft 4200, which includes housed propulsion devices 4202.

Device components (e.g., rotary units, rotary mechanisms, drive mechanism components, gear components, shafts, rotational components, device housings, doors, support structures, etc.) are optionally formed by various fabrication techniques or combinations of such techniques including, e.g., cast molding, stamping, machining, embossing, extrusion, engraving, injection molding, etching (e.g., electrochemical etching, etc.), or other techniques. These and other suitable fabrication techniques are generally known in the art and described in, e.g., Molinari et al. (Eds.), Metal Cutting and High Speed Machining, Kluwer Academic Publishers (2002), Altintas, Manufacturing Automation: Metal Cutting Mechanics, Machine Tool Vibrations, and CNC Design, Cambridge University Press (2000), Stephenson et al., Metal Cutting Theory and Practice, Marcel Dekker (1997), Fundamentals of Injection Molding, W.J.T. Associates (2000), Whelan, Injection Molding of Thermoplastics Materials, Vol. 2, Chapman & Hall (1991), Rosato, Injection Molding Handbook, 3.sup.rd Ed., Kluwer Academic Publishers (2000), Fisher, Extrusion of Plastics, Halsted Press (1976), and Chung, Extrusion of Polymers: Theory and Practice, Hanser-Gardner Publications (2000), which are each incorporated by reference. Exemplary materials optionally used to fabricate device components include, e.g., metal, glass, wood, polymethylmethacrylate, polyethylene, polydimethylsiloxane, polyetheretherketone, polytetrafluoroethylene, polystyrene, polyvinylchloride, polypropylene, polysulfone, polymethylpentene, and polycarbonate, among many others. In certain embodiments, following fabrication, device components are optionally further processed, e.g., by painting, coating surfaces with a hydrophilic coating, a hydrophobic coating, or the like.

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above can be used in various combinations. All publications, patents, patent applications, and/or other documents cited in this application are incorporated by reference in their entirety for all purposes to the same extent as if each individual publication, patent, patent application, and/or other document were individually indicated to be incorporated by reference for all purposes.

What is claimed is:

1. A rotary mechanism, comprising:
   at least first, second, and third rotational components, wherein at least one of the rotational components comprises at least one implement;
   at least first and second counter-rotational mechanisms, wherein the first counter rotational mechanism operably engages at least the first and second rotational components, and wherein the second counter-rotational mechanism operably engages at least the second and third rotational components; and,
   at least one drive mechanism component or a portion thereof operably engaged with one or more of the rotational components and/or with one or more of the counter-rotational mechanisms, which drive mechanism component or portion thereof is configured at least to effect rotation of the rotational components and the counter-rotational mechanisms such that the first and third rotational components rotate in a first direction and the second rotational component rotates in a second direction.

2. The rotary mechanism of claim 1, comprising more than three rotational components.

3. The rotary mechanism of claim 1, wherein the second rotational component is disposed between the first and third rotational components.

4. The rotary mechanism of claim 1, wherein at least one of the rotational components comprises one or more gear components that are configured to operably engage one or more implements rotatably coupled to one or more other rotational components.

5. The rotary mechanism of claim 1, wherein the implement is configured to effect the movement of one or more other components when the implement operably engages the other components.

6. The rotary mechanism of claim 1, wherein the implement comprises one or more of: a blade, a razor, a prong, a peg, a claw, a tine, a chain, a stake, a column, a pillar, an arch, a bracket, a gear component, a bristle, a plume, an abrasive component, an elastomeric component, a nail filing component, a nail buffing component, a hair cutting component, a massaging component, or a post.

7. The rotary mechanism of claim 1, wherein at least a portion of the implement comprises at least one cross-sectional shape selected from the group consisting of: a circle, an oval, a square, a rectangle, a trapezoid, an irregular n-sided polygon, and a regular n-sided polygon.

8. The rotary mechanism of claim 1, wherein the drive mechanism component or portion thereof is configured to effect rotation of the rotational components and the counter-rotational mechanisms such that the first and third rotational components rotate in a second direction and the second rotational component rotates in a first direction.

9. The rotary mechanism of claim 1, wherein the implement is rotatably coupled to the rotation component.

10. The rotary mechanism of claim 9, wherein the implement is configured to operably engage one or more gear components of one or more other rotational components.

11. The rotary mechanism of claim 1, wherein at least the first counter-rotational mechanism comprises at least a first gear component disposed on the first rotational component, at least a second gear component disposed on the second rotational component, and at least a third gear component that operably engages the first and second gear components such that when the first gear component rotates in the first direction, the second and third gear components rotate in the second direction and when the first gear component rotates in the second direction, the second and third gear components rotate in the first direction.

12. The rotary mechanism of claim 11, comprising a retaining mechanism that retains the third gear component operably engaged with the first and second gear components.

13. The rotary mechanism of claim 11, wherein the second gear component substantially defines a gear receiving area that is configured to receive at least a portion of the third gear component.

14. The rotary mechanism of claim 13, comprising at least one gear structure that comprises at least one support component, wherein the third gear component is rotatably coupled to the support component.

15. The rotary mechanism of claim 14, wherein the gear structure is at least partially disposed in the gear receiving area.

16. The rotary mechanism of claim 14, wherein the gear structure is rotatably coupled to at least one of the first and second rotational components.

17. The rotary mechanism of claim 14, wherein at least one of the first and second rotational components comprises at least one substantially or partially circular indentation and the gear structure comprises at least one projection configured to at least partially fit and move within the substantially or partially circular indentation to retain the gear structure relative to first and/or second rotational components.

18. The rotary mechanism of claim 14, wherein the gear structure comprises at least one substantially or partially circular indentation and at least one of the first and second rotational components comprises at least one projection configured to at least partially fit and move within the substantially or partially circular indentation to retain the gear structure relative to first and/or second rotational components.

19. A device comprising the rotary mechanism of claim 1.

20. The device of claim 19, wherein the device is selected from the group consisting of: a held-held device, a rototiller, a hair cutting device, a massaging device, nail grooming device, a propulsion device, a woodworking device, a lathe, a woodchipping device, a machining device, a dermabrasion device, a medical device, a dental device, a cleaning device, an engine, snowblower, a nozzle, a food preparation device, a grinder, a pencil sharpener, a lawn mower, a vacuum cleaner, a hair dryer, a plumbing device, a weapon, a surfboard, a scuba device, a component thereof, and a combination thereof.

21. A vehicle comprising the rotary mechanism of claim 1.

22. The vehicle of claim 21, wherein the vehicle is selected from the group consisting of: a farming vehicle, a mining vehicle, a construction vehicle, a submarine, an aircraft, a marine vehicle, a boat, a personal watercraft, and a military vehicle.

* * * * *

UNITED STATES PATENT AND TRADEMARK OFFICE
CERTIFICATE OF CORRECTION

| | | |
|---|---|---|
| PATENT NO. | : 8,152,679 B2 | Page 1 of 1 |
| APPLICATION NO. | : 12/577326 | |
| DATED | : April 10, 2012 | |
| INVENTOR(S) | : Christopher C. Sappenfield | |

It is certified that error appears in the above-identified patent and that said Letters Patent is hereby corrected as shown below:

In the Specifications:

Column 3, line 17, in relevant part, incorrectly recites the phrase:

a held-held device when in fact the phrase should read:

a hand-held device.

In the Claims:

Column 42, line 43 of claim 20, in relevant part, incorrectly recites the phrase:

a held-held device when in fact the phrase should read:

a hand-held device.

Signed and Sealed this
Thirtieth Day of April, 2013

Teresa Stanek Rea
*Acting Director of the United States Patent and Trademark Office*